US008173704B2

(12) United States Patent
Bartel et al.

(10) Patent No.: US 8,173,704 B2
(45) Date of Patent: May 8, 2012

(54) DIFLUOROPHENOL DERIVATIVES AND THEIR USE

(75) Inventors: Stephan Bartel, Kürten (DE); Michael Hahn, Langenfeld (DE); Wahed Ahmed Moradi, Monheim (DE); Eva-Maria Becker, Wuppertal (DE); Thomas Rölle, Leverkusen (DE); Johannes-Peter Stasch, Solingen (DE); Karl-Heinz Schlemmer, Wuppertal (DE); Frank Wunder, Wuppertal (DE); Andreas Knorr, Erkrath (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 363 days.

(21) Appl. No.: 12/083,509

(22) PCT Filed: Oct. 9, 2006

(86) PCT No.: PCT/EP2006/009726
§ 371 (c)(1),
(2), (4) Date: Jul. 6, 2009

(87) PCT Pub. No.: WO2007/045369
PCT Pub. Date: Apr. 26, 2007

(65) Prior Publication Data
US 2009/0291993 A1 Nov. 26, 2009

(30) Foreign Application Priority Data

Oct. 21, 2005 (DE) .......................... 10 2005 050 497

(51) Int. Cl.
*A61K 31/19* (2006.01)
*A61K 31/195* (2006.01)
*C07C 59/00* (2006.01)
*C07C 65/03* (2006.01)
*C07C 321/00* (2006.01)

(52) U.S. Cl. .......... 514/564; 514/568; 560/17; 562/471; 562/472

(58) Field of Classification Search .................. 514/564, 514/568; 562/471, 472; 560/17
See application file for complete search history.

(56) References Cited

U.S. PATENT DOCUMENTS

| 6,180,656 | B1 | 1/2001 | Furstner et al. |
| 6,387,940 | B1 | 5/2002 | Straub et al. |
| 6,410,740 | B1 | 6/2002 | Straub et al. |
| 6,414,009 | B1 | 7/2002 | Straub et al. |
| 6,451,805 | B1 | 9/2002 | Straub et al. |
| 6,462,068 | B1 | 10/2002 | Straub et al. |
| 6,864,287 | B1 | 3/2005 | Alonso-Alija et al. |
| 7,087,644 | B1 * | 8/2006 | Alonso-Alija et al. ....... 514/564 |
| 7,998,988 | B2 | 8/2011 | Bartel et al. |
| 2004/0082658 | A1 | 4/2004 | Haerter et al. |
| 2004/0082798 | A1 | 4/2004 | Alonso-Alija et al. |
| 2004/0176446 | A1 | 9/2004 | Alonso-Alija et al. |
| 2007/0179139 | A1 | 8/2007 | Alonso-Alija et al. |
| 2008/0058314 | A1 | 3/2008 | Alonso-Alija et al. |

FOREIGN PATENT DOCUMENTS

| EP | 0341551 A1 | 11/1989 |
| WO | WO-98/16223 A1 | 4/1998 |
| WO | WO-98/16507 A2 | 4/1998 |
| WO | WO-98/23619 A1 | 6/1998 |
| WO | WO-01/19355 A2 | 3/2001 |
| WO | WO-01/19776 A2 | 3/2001 |
| WO | WO-01/19778 A1 | 3/2001 |
| WO | WO-01/19780 | 3/2001 |
| WO | WO-01/19780 A2 | 3/2001 |
| WO | WO-02/070462 A1 | 9/2002 |
| WO | WO-02/070510 A2 | 9/2002 |

OTHER PUBLICATIONS

FN Ko et al.: "YC-1, A Novel Activator of Platelet Guanylate Cyclase," Blood, 84, 1994, pp. 4226-4233.
A. Mulsch et al.: "Effect of YC-1, an NO-independent, superoxide-Sensitive Stimulator of Soluble Guanylyl Cyclase, on Smooth Muscle Responsiveness to Nitrovasodilators," British Journal of Pharmacology, 120, 1997, pp. 681-689.
D. B. Glass et al.: "Stimulation of Human Platelet Guanylate Cyclase by Fatty Acids," The Journal of Biological Chemistry, vol. 252, No. 4, Feb. 25, 1977, pp. 1279-1285.
D. J. Pettibone et al.: "A Structurally Novel Stimulator of Guanylate Cyclase with Long-Lasting Hypotensive Activity in the Dog," European Journal of Pharmacology, 116, 1985, pp. 307-312.
S-M Yu et al.: "Vasorelaxant Effect of Isoliquiritigenin, a Novel Soluble Guanylate Cyclase Activator, in Rat Aorta," British Journal of Pharmacology, 114, 1995, pp. 1587-1594.
R. Gerzer et al.: "Soluble Guanylate Cyclase Purified from Bovine Lung Contains Heme and Copper," FEBS Letters, vol. 132, No. 1, Sep. 1981, pp. 71-74.
M. Hoenicka et al.: "Purified Soluble Guanylyl Cyclase Expressed in a Baculovirus/Sf9 System: Stimulation by YC-1, Nitirc Oxide, and Carbon Monoxide," J. Mol. Med, 77, 1999, pp. 14-23.
L. J. Ignarro: "Regulation of Cytosolic Guanylyl Cyclase by Porphyrins and Metalloporphyrins," Advances in Pharmacology, vol. 26, 1994, pp. 35-65.
A. Mulsch et al.: "Potentiation of Vascular Responses to Non-Donors by An No-Independent Activator of Soluble Guanylyl Cyclase," Naunyn Schmiedebergs Arch. Pharmacol. 355, R47.
U.S. Appl. No. 12/083,761, filed May 19, 2009.
U.S. Appl. No. 12/085,543, filed Feb. 17, 2009.
U.S. Appl. No. 12/083,814, filed in Oct. 19, 2009.
U.S. Appl. No. 12/529,342, filed Mar. 25, 2010.
Demko, et al., "Preparation of 5-substituted 1H-tetrazoles from nitriles in water," J. Org. Chem. 2001, 66: 7945-7950.
Patani et al., "Bioisterism: A rational Approach in Drug Design," Chem. Rev., 1996, 96: 3147-3176.

* cited by examiner

*Primary Examiner* — Susannah Chung
(74) *Attorney, Agent, or Firm* — Karen B. King

(57) ABSTRACT

The present application relates to novel difluorophenol derivatives, processes for their preparation, their use for the treatment and/or prophylaxis of diseases, and their use for producing medicaments for the treatment and/or prophylaxis of diseases, especially for the treatment and/or prevention of cardiovascular disorders.

6 Claims, No Drawings

DIFLUOROPHENOL DERIVATIVES AND THEIR USE

RELATED APPLICATIONS/PATENTS AND INCORPORATION BY REFERENCE

This application is a National Stage Application filed under 35 U.S.C. §371 based on International Application No. PCT/EP2006/009726, filed Oct. 9, 2006, which claims priority to German Patent Application Number 102005050497.3, filed Oct. 21, 2005, the entire contents each of which are incorporated herein by reference. The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel difluorophenol derivatives, processes for their preparation, their use for the treatment and/or prophylaxis of diseases, and their use for producing medicaments for the treatment and/or prophylaxis of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., *Blood* 84 (1994), 4226; Mülsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223, WO 98/16507 and WO 98/23619).

The above-described stimulators of soluble guanylate cyclase stimulate the enzyme either directly via the heme group (carbon monoxide, nitric oxide or diphenyliodonium hexafluorophosphate) by interacting with the iron center of the heme group and a change in conformation which results therefrom and leads to an increase in the enzymic activity [Gerzer et al., *FEBS Lett.* 132 (1981), 71] or via a heme-dependent mechanism which is independent of NO but leads to a potentiation of the stimulating effect of NO or CO [e.g. YC-1, Hoenicka et al., *J. Mol. Med.* 77 (1999) 14; or the pyrazole derivatives described in WO 98/16223, WO 98/16507 and WO 98/23619].

It has not been possible to confirm the stimulating effect, asserted in the literature, of isoliquiritigenin and of fatty acids such as, for example, of arachidonic acid, prostaglandin endoperoxides and fatty acid hydroperoxides on soluble guanylate cyclase [cf., for example, Hoenicka et al., *J. Mol. Med.* 77 (1999), 14].

If the heme group is removed from soluble guanylate cyclase, the enzyme still shows a detectable basal catalytic activity, i.e. cGMP is still produced. The remaining basal catalytic activity of the heme-free enzyme cannot be stimulated by any of the aforementioned known stimulators.

Stimulation of heme-free soluble guanylate cyclase by protoporphyrin IX has been described [Ignarro et al., *Adv. Pharmacol.* 26 (1994), 35]. However, protoporphyrin IX can be regarded as a mimic of the NO-heme adduct, which is why addition of protoporphyrin IX to soluble guanylate cyclase ought to lead to production of a structure of the enzyme corresponding to the heme-containing soluble guanylate cyclase which is stimulated by NO. This is also verified by the fact that the stimulating effect of protoporphyrin IX is increased by the NO-independent but heme-dependent stimulator YC-1 described above [Mülsch et al., *Naunyn Schmiedebergs Arch. Pharmacol.* 355, R47].

In contrast to the above-described stimulators of soluble guanylate cyclase, the compounds of the present invention are able to activate both the heme-containing and the heme-free form of soluble guanylate cyclase. Thus, with these novel activators, the enzyme is stimulated via a heme-independent pathway, which is also verified by the facts that the novel activators firstly show no synergistic effect with NO on the heme-containing enzyme, and secondly the effect of these novel activators cannot be blocked by the heme-dependent inhibitor of soluble guanylate cyclase 1H-1,2,4-oxadiazole-(4,3-a)-quinoxalin-1-one (ODQ).

EP 0 341 551-A1 discloses alkenoic acid derivatives as leucotriene antagonists for the treatment of disorders of the circulatory and respiratory systems. WO 01/19355, WO 01/19776, WO 01/19778, WO 01/19780, WO 02/070462 and WO 02/070510 describe dicarboxylic acid and amino dicarboxylic acid derivatives as stimulators of soluble guanylate cyclase for the treatment of cardiovascular disorders. However, it has emerged that these compounds have disadvantages in relation to their pharmacokinetic properties, such as, in particular, a low bioavailability and/or an only short duration of action after oral administration.

It was therefore an object of the present invention to provide novel compounds which act as activators of soluble guanylate cyclase but do not have the aforementioned disadvantages of the prior art compounds.

The present invention relates to compounds of the general formula (I)

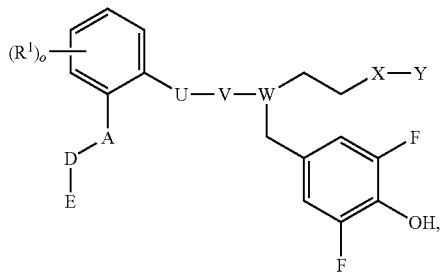

in which
U, V and W together form a group of the formula *-CH=CH—CH<, *-CH$_2$—CH$_2$—CH< or *-CH$_2$—CH$_2$—N<, in which * means the point of linkage to the phenyl ring,
A is O or CH$_2$,
D is a bond or is (C$_1$-C$_7$)-alkanediyl, (C$_2$-C$_7$)-alkenediyl or (C$_2$-C$_7$)-alkynediyl, each of which may be substituted one or more times by fluorine,
E is hydrogen, trifluoromethyl or a group of the formula

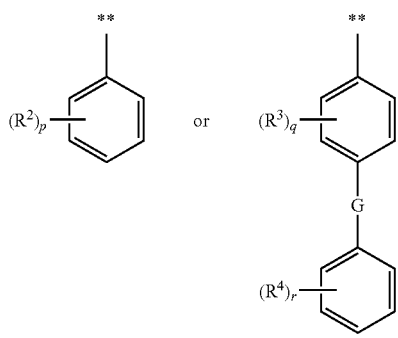

in which ** means the point of linkage to the group D and
G is a bond, CH$_2$, —CH$_2$—CH$_2$— or —CH=CH—,
X is —CH$_2$—CH$_2$— or a group of the formula

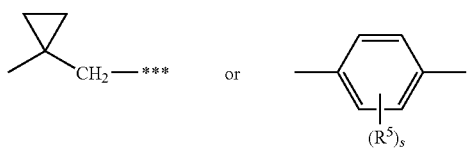

in which *** means the point of linkage to the group Y,
Y is carboxyl or a group of the formula

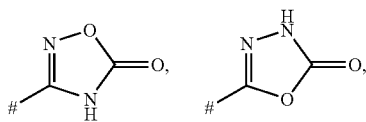

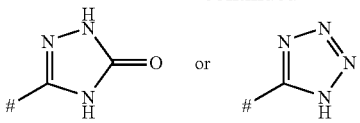

in which # means the respective point of linkage,
R$^1$, R$^2$, R$^3$, R$^4$ and R$^5$ are independently of one another substituents selected from the series halogen, (C$_1$-C$_6$)-alkyl, trifluoromethyl, (C$_1$-C$_6$)-alkoxy, trifluoromethoxy, cyano and nitro,
and
o, p, q, r and s are independently of one another each the number 0, 1, 2, 3 or 4,
where in the case where R$^1$, R$^2$, R$^3$, R$^4$ or R$^5$ occur more than once, their meanings may in each case be identical or different,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_6)$-Alkyl and $(C_1-C_4)$-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, iso-butyl, sec-butyl, tert-butyl, 1-ethylpropyl, n-pentyl and n-hexyl.

$(C_1-C_7)$-Alkanediyl is in the context of the invention a straight-chain or branched divalent alkyl radical having 1 to 7 carbon atoms. A straight-chain alkanediyl radical having 1 to 6 carbon atoms is preferred. Examples which may be preferably mentioned are: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

$(C_2-C_7)$-Alkenediyl is in the context of the invention a straight-chain or branched divalent alkenyl radical having 2 to 7 carbon atoms and up to 3 double bonds. A straight-chain alkenediyl radical having 2 to 6 carbon atoms and up to 2 double bonds is preferred. Examples which may be preferably mentioned are: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

$(C_2-C_7)$-Alkynediyl is in the context of the invention a straight-chain or branched divalent alkynyl radical having 2 to 7 carbon atoms and up to 3 triple bonds. A straight-chain alkynediyl radical having 2 to 6 carbon atoms and up to 2 triple bonds is preferred. Examples which may be preferably mentioned are: ethyne-1,2-diyl, propyne-1,3-diyl, but-1-yne-1,4-diyl, but-1-yne-1,3-diyl, but-2-yne-1,4-diyl, pent-2-yne-1,5-diyl, pent-2-yne-1,4-diyl and hex-3-yne-1,6-diyl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

$(C_1-C_4)$-Alkoxycarbonyl is in the context of the invention a straight-chain or branched alkoxy radical having 1 to 4 carbon atoms, which is linked via a carbonyl group. Examples which may be preferably mentioned are methoxycarbonyl, ethoxycarbonyl, n-propoxycarbonyl, isopropoxycarbonyl and tert-butoxycarbonyl.

Halogen in the context of the invention includes fluorine, chlorine, bromine and iodine. Chlorine or fluorine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

If a radical in the compounds according to the invention can be substituted more than once by fluorine, then in the context of the present invention this includes a perfluoro substitution.

Preference is given in the context of the present invention to compounds of the formula (I) in which U, V and W together form a group of the formula *-CH=CH—CH< or *-CH$_2$—CH$_2$—N< in which * means the point of linkage to the phenyl ring, A is O, D is $(C_1-C_7)$-alkanediyl which may be substituted one or more times by fluorine, E is hydrogen, trifluoromethyl or is a group of the formula

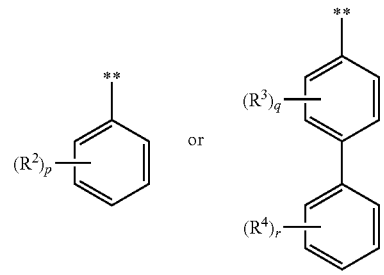

in which ** means the point of linkage to the group D,

X is —CH$_2$—CH$_2$— or a group of the formula

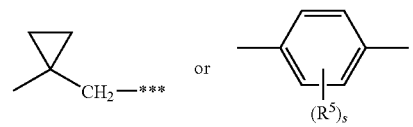

in which *** means the point of linkage to the group Y,

Y is carboxyl or a group of the formula

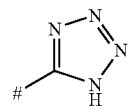

in which # means the point of linkage, $R^1$, $R^2$, $R^3$ and $R^4$ are independently of one another a substituent selected from the series fluorine, chlorine, bromine, $(C_1-C_4)$-alkyl, trifluoromethyl, $(C_1-C_4)$-alkoxy and trifluoromethoxy, o, p, q and r are independently of one another each the number 0, 1 or 2, where in the case where $R^1$, $R^2$, $R^3$ or $R^4$ occur more than once, their meanings may in each case be identical or different, $R^5$ is fluorine, and s is the number 0 or 1, and the salts, solvates and solvates of the salts thereof.

Particular preference is given in the context of the present invention to compounds of the formula (I-A)

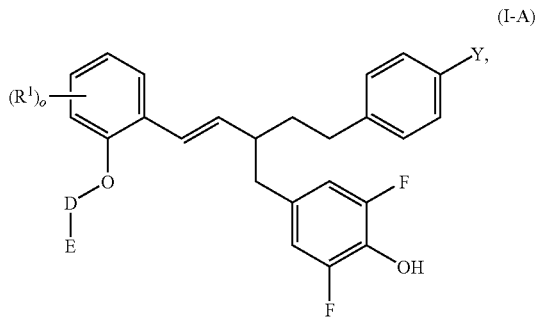
(I-A)

in which
D is ($C_1$-$C_7$)-alkanediyl which may be substituted one or more times by fluorine,
E is hydrogen, trifluoromethyl or is a group of the formula

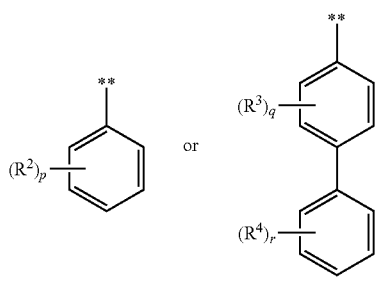

in which ** means the point of linkage to the group D,
Y is carboxyl or a group of the formula

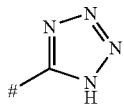

in which # means the point of linkage to the phenyl ring,
$R^1$, $R^2$, $R^3$ and $R^4$ are independently of one another a substituent selected from the series fluorine, chlorine, bromine, methyl, tert-butyl, trifluoromethyl and methoxy,
and
o, p, q and r are independently of one another each the number 0, 1 or 2,
where in the case that $R^1$, $R^2$, $R^3$ or $R^4$ occur more than once, their meanings may in each case be identical or different,
and the salts, solvates and solvates of the salts thereof.

Particular preference is given in the context of the present invention also to compounds of the formula (I-B)

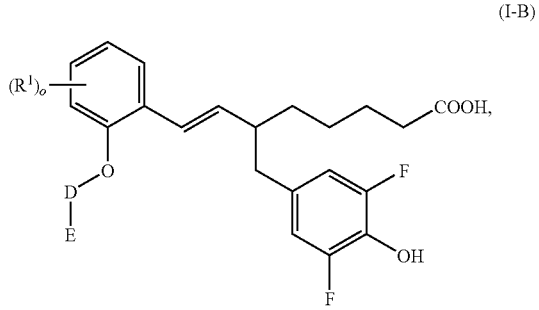
(I-B)

in which
D is ($C_1$-$C_7$)-alkanediyl which may be substituted one or more times by fluorine, E is hydrogen, trifluoromethyl or is a group of the formula

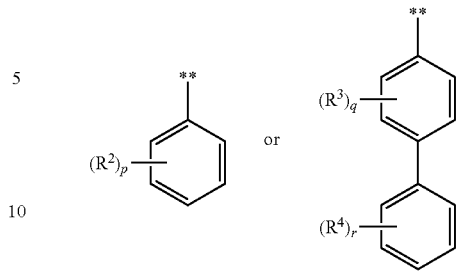

in which ** means the point of linkage to the group D,
$R^1$, $R^2$, $R^3$ and $R^4$ are independently of one another a substituent selected from the series fluorine, chlorine, bromine, methyl, tert-butyl, trifluoromethyl and methoxy,
and
o, p, q and r are independently of one another each the number 0, 1 or 2,
where in the case that $R^1$, $R^2$, $R^3$ or $R^4$ occur more than once, their meanings may in each case be identical or different,
and the salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I) in which U, V, and W together form a group of the formula *-CH=CH-CH<, in which * means the point of linkage to the phenyl ring, and Y is carboxyl, characterized in that compounds of the formula (II)

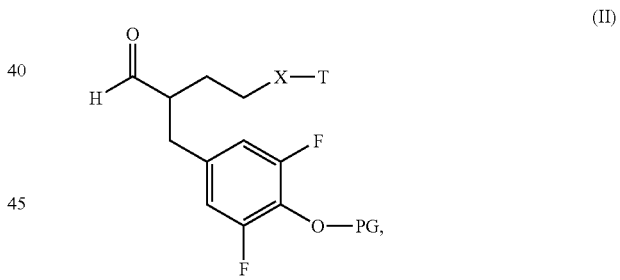
(II)

in which X has the meaning indicated above, and
PG is a hydroxy protective group, in particular a silyl group such as, for example, trimethylsilyl, triisopropylsilyl, tert-butyldimethylsilyl or tert-butyldiphenylsilyl,
and
T is cyano or ($C_1$-$C_4$)-alkoxycarbonyl,
are either
[A-1] reacted in an inert solvent in the presence of a base with a compound of the formula (III-A)

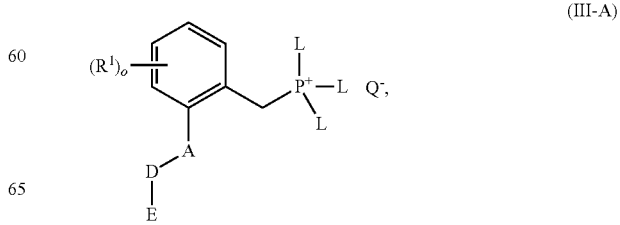
(III-A)

in which A, D, E, R¹ and o each have the meanings indicated above, and
L is phenyl or o-, m- or p-tolyl
and
Q is halide or tosylate,
to give compounds of the formula (IV-A)

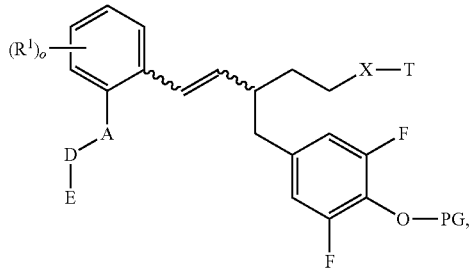

(IV-A)

in which A, D, E, X, R¹, o, PG and T each have the meanings indicated above,
or
[A-2] reacted in an inert solvent in the presence of a base with a compound of the formula (III-B)

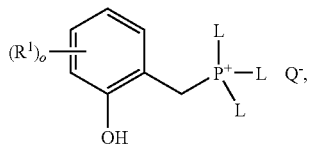

(III-B)

in which R¹, o, L and Q each have the meanings indicated above,
initially to give compounds of the formula (IV-B)

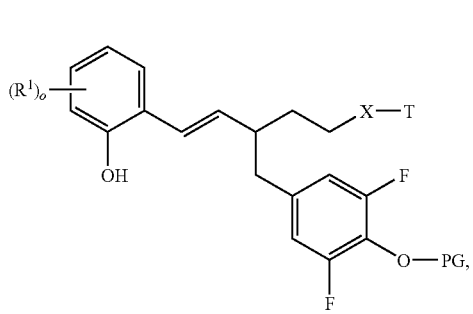

(IV-B)

in which X, R¹, o, PG and T each have the meanings indicated above,
and these are then alkylated in an inert solvent in the presence of a base with a compound of the formula (V)

E-D*-Z¹  (V), in which E has the meaning indicated above,
D* has the meaning of D indicated above, but is not a bond, and
Z¹ is a leaving group, such as, for example, halogen, tosylate or mesylate, to give compounds of the formula (IV-C)

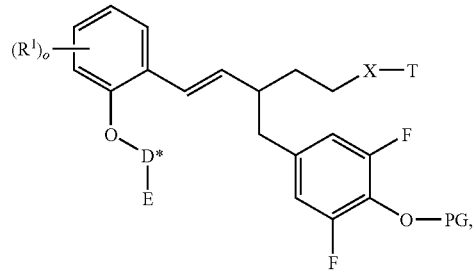

(IV-C)

in which D*, E, X, R¹, o, PG and T each have the meanings indicated above,
the resulting compounds of the formula (IV-A) or (IV-C) are then converted by eliminating the protective group PG into compounds of the formula (VI)

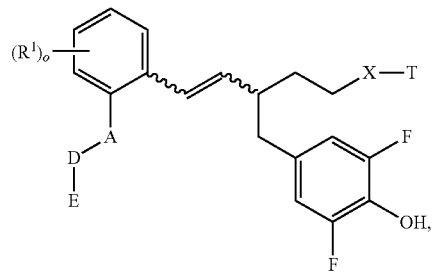

(VI)

in which A, D, E, X, R¹, o and T each have the meanings indicated above,
and these are reacted by hydrolysis of the ester or nitrile group T to give carboxylic acids of the formula (I-C)

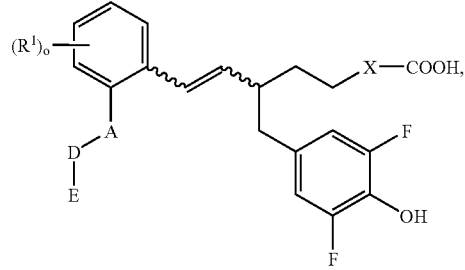

(I-C)

in which A, D, E, X, R¹ and o each have the meanings indicated above,
and the compounds of the formula (I-C) are separated where appropriate by methods known to the skilled person into their enantiomers and/or diastereomers, and/or where appropriate converted with the appropriate (i) solvents and/or (ii) bases or acids into the solvates, salts and/or solvates of the salts thereof.

Inert solvents for process steps (II)+(III-A)→(IV-A) and (II)+(III-B)→(IV-B) are, for example, ethers such as diethyl ether, tetrahydrofuran, glycol dimethyl ether or diethylene glycol dimethyl ether, or hydrocarbons such as benzene, toluene, xylene, pentane, hexane, heptane, cyclohexane or petroleum fractions, or mixtures of these solvents. Tetrahydrofuran in a mixture with hexane is preferably used.

Suitable bases for these process steps are the bases customary for a Wittig reaction. These include in particular strong bases such as n-, sec- or tert-butyllithium, lithium diisopropylamide (LDA) or lithium, sodium or potassium bis(trimethylsilyl)amide. n-Butyllithium is preferred.

The reactions (II)+(III-A)→(IV-A) and (II)+(III-B)→(IV-B) are generally carried out in a temperature range from −78° C. to +20° C., preferably at −20° C. to +10° C.:

Examples of inert solvents for process step (IV-B)+(V)→(IV-C) are ethers such as diethyl ether, dioxane, tetrahydrofuran, glycol dimethyl ether or diethylene glycol dimethyl ether, or other solvents such as acetonitrile, dimethylformamide, dimethyl sulfoxide, N,N'-dimethylpropyleneurea (DMPU) or N-methylpyrrolidone (NMP). It is likewise possible to employ mixtures of the solvents mentioned. Acetonitrile is preferably used.

Suitable bases for this process step are in particular potassium carbonate, sodium or potassium hydride, lithium diisopropylamide or n-butyllithium. Potassium carbonate is preferably used.

The reaction (IV-B)+(V)→(IV-C) is generally carried out in a temperature range from +20° C. to +120° C., preferably at +50° C. to +100° C.

The hydroxy protective group PG used is preferably a silyl group such as, for example, trimethylsilyl, triisopropylsilyl, tert-butyldimethylsilyl or tert-butyldiphenylsilyl. Triisopropylsilyl is particularly preferred. The silyl group is preferably eliminated in process step (IV-A) or (IV-C) →(VI) with the aid of tetra-n-butylammonium fluoride (TBAF) or hydrogen fluoride. The reaction is generally carried out in tetrahydrofuran as solvent in a temperature range from 0° C. to +40° C.

Hydrolysis of the ester or nitrile group T in process step (VI)→(I-C) takes place by conventional methods, by treating the esters and nitriles respectively in inert solvents with acids or bases, and with the latter converting the initially produced salts into the free carboxyic acids by treatment with acid. The ester cleavage in the case of tert-butyl esters preferably takes place with acids.

Inert solvents suitable for these reactions are water or the organic solvents usual for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichlormethane, dimethylformamide or dimethyl sulfoxide. It is likewise possible to employ mixtures of the solvents mentioned. In the case of a basic ester hydrolysis, preferably mixtures of water with dioxane, tetrahydrofuran, methanol and/or ethanol are employed, and in the case of nitrile hydrolysis preferably water or n-propanol is employed. In the case of reaction with trifluoroacetic acid, preferably dichloromethane is used, and in the case of reaction with hydrogen chloride, preferably tetrahydrofuran, diethyl ether, dioxane or water is used.

Suitable bases are the usual inorganic bases. These preferably include alkali metal or alkaline earth metal hydroxides such as, for example, sodium, lithium, potassium or barium hydroxide, or alkali metal or alkaline earth metal carbonates such as sodium, potassium or calcium carbonate. Sodium, potassium or lithium hydroxide are particularly preferred.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, where appropriate with addition of water. Hydrogen chloride or trifluoroacetic acid are preferred in the case of the tert-butyl esters, and hydrochloric acid in the case of the methyl esters.

The ester cleavage generally takes place in a temperature range from 0° C. to +100° C., preferably at +20° C. to +60° C. The nitrile hydrolysis is generally carried out in a temperature range from +50° C. to +150° C., preferably at +90° C. to +110° C.

The process sequence (IV-A) or (IV-C)→(I-C) can where appropriate also be carried out as a one-pot reaction, in which the elimination of the protective group PG and the hydrolysis of the group T take place simultaneously. Suitable for this purpose are in particular strong acids or bases such as hydrogen chloride or trifluoroacetic acid, or sodium or potassium hydroxide.

The reactions mentioned can be carried out under atmospheric, elevated or reduced pressure (e.g. from 0.5 to 5 bar). They are generally carried out in each case under atmospheric pressure.

The aldehydes of the formula (II) can be prepared in analogy to processes known from the literature, for example by a sequential dialkylation of diallyl malonate with compounds of the formulae (VII) and (VIII)

in which X, PG and T each have the meanings indicated above, and
$Z^2$ and $Z^3$ are identical or different and are a leaving group such as, for example, halogen, mesylate or tosylate,
to give compounds of the formula (IX)

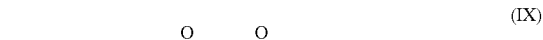

in which X, PG and T each have the meanings indicated above,
subsequent ester cleavage to give compounds of the formula (X)

in which X, PG and T each have the meanings indicated above,
and subsequent reduction of the carboxylic acid group (see also reaction schemes 3 and 6 below).

The compounds of the formulae (III-A) and (III-B) can be obtained by processes known from the literature by reacting compounds of the formula (XI-A) or (XI-B)

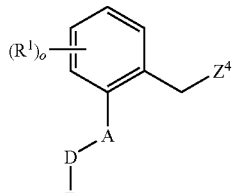
(XI-A)

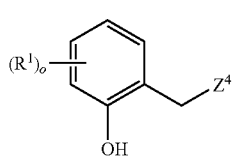
(XI-B)

in which A, D, E, $R^1$ and o each have the meanings indicated above, and
$Z^4$ is a leaving group such as, for example, halogen or tosylate, or is hydroxy,
with for example triphenylphosphine or (in the case of $Z^4$=OH) triphenylphosphine hydrobromide (see also reaction scheme 1 below).

The invention further relates to a process for preparing the compounds according to the invention of the formula (I) in which U, V and W together form a group of the formula *-CH$_2$—CH$_2$—N<, in which * means the point of linkage to the phenyl ring, and Y is carboxyl,
characterized in that compounds of the formula (XII)

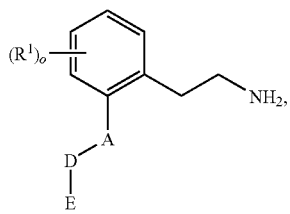
(XII)

in which A, D, E, $R^1$ and o each have the meanings indicated above,
are initially alkylated in an inert solvent in the presence of a base with a compound of the formula (VII)

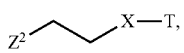
(VII)

in which X has the meaning indicated above, and
T is cyano or ($C_1$-$C_4$)-alkoxycarbonyl
and
$Z^2$ is a leaving group such as, for example, halogen, mesylate or tosylate, to give compounds of the formula (XIII)

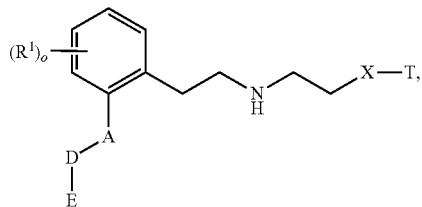
(XIII)

in which A, D, E, X, $R^1$, o and T each have the meanings indicated above,
subsequently reacted in an inert solvent in the presence of a base with a compound of the formula (VIII)

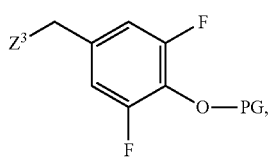
(VIII)

in which
PG is a hydroxy protective group, in particular a silyl group such as, for example, trimethylsilyl, triisopropylsilyl, tert-butyldimethylsilyl or tert-butyldiphenylsilyl,
and
$Z^3$ is a leaving group such as, for example, halogen, mesylate or tosylate,
to give compounds of the formula (XIV)

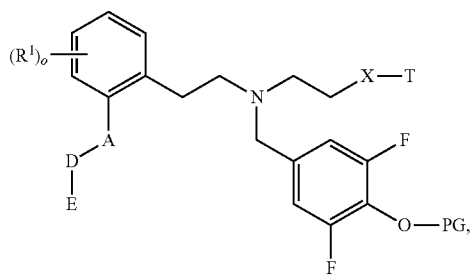
(XIV)

in which A, D, E, X, $R^1$, o, PG and T each have the meanings indicated above,
then converted by eliminating the protective group PG into compounds of the formula (XV)

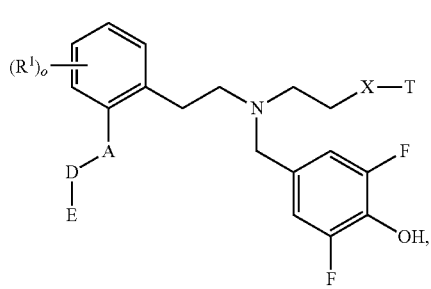
(XV)

in which A, D, E, X, $R^1$, o and T each have the meanings indicated above, and the latter are reacted by hydrolysis of the ester or nitrile group T to give carboxylic acids of the formula (I-D)

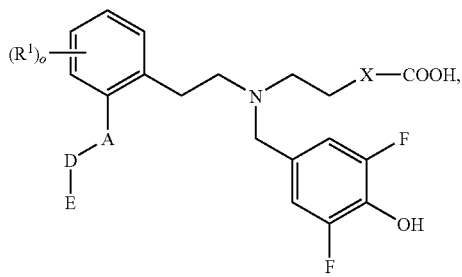
(I-D)

in which A, D, E, X, R¹ and o each have the meanings indicated above,
and the compounds of the formula (I-D) are converted where appropriate with the appropriate (i) solvents and/or (ii) bases or acids into the solvates, salts and/or solvates of the salts thereof.

In the process sequence (XII)→(I-D) described above it is possible if expedient for individual reaction steps also to be transposed in the sequence thereof. Thus, for example, the amine (XII) can be dialkylated initially with the compound (VIII) and then with the compound (VII) to give the compounds of the formula (XIV). It is likewise possible for the hydrolysis of group T and/or the elimination of the protective group PG to take place at earlier times during the process sequence (XII)→(I-D) (cf. also reaction scheme 10 below). Such variations are familiar to the skilled worker and are encompassed by the process according to the invention.

Inert solvents for process steps (XII)+(VII)→(XIII) and (XIII)+(VIII)→(XIV) are for example ethers such as diethyl ether, tert-butyl methyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloroethane, trichloroethylene or chlorobenzene, or other solvents such as acetone, acetonitrile, pyridine, dimethyl sulfoxide, dimethylformamide, N,N'-dimethylpropyleneurea (DMPU) or N-methylpyrrolidone (NMP). It is likewise possible to use mixtures of the solvents mentioned. Dimethylformamide and acetone are preferred.

Bases suitable for these process steps are the usual inorganic or organic bases. These preferably include alkali metal or alkaline earth metal carbonates such as lithium, sodium, potassium, calcium or cesium carbonate, alkali metal hydrides such as sodium hydride, amides such as lithium diisopropylamide or lithium or potassium bis(trimethylsilyl) amide, or organic amines such as triethylamine, N-methylmorpholine, N-methylpiperidine, N,N-diisopropylethylamine or pyridine. Sodium or potassium carbonate and triethylamine are particularly preferred.

The reactions (XII)+(VII)→(XIII) and (XIII)+(VIII)→(XIV) can advantageously be carried out where appropriate in the presence of an alkylation catalyst such as lithium, sodium or potassium iodide.

Process steps (XII)+(VII)→(XIII) and (XIII)+(VIII)→(XIV) generally take place in a temperature range from +20° C. to +100° C., preferably at +50° C. to +80° C.

The hydroxy protective group PG preferably used is a silyl group such as, for example, trimethylsilyl, triisopropylsilyl, tert-butyldimethylsilyl or tert-butyldiphenylsilyl. Triisopropylsilyl is particularly preferred. The silyl group is preferably eliminated in process step (XIV)→(XV) with the aid of tetra-n-butylammonium fluoride (TBAF) or hydrogen fluoride.

The reaction is generally carried out in tetrahydrofuran as solvent in a temperature range from 0° C. to +40° C.

The hydrolysis of the ester or nitrile group T in process step (XV)→(I-D) takes place by conventional methods by treating the esters or nitriles in inert solvents with acids or bases, and in the latter case converting the initially formed salts into the free carboxylic acids by treatment with acid. In the case of the tert-butyl esters, the ester cleavage preferably takes place with acids.

Inert solvents suitable for these reactions are water or the organic solvents usual for an ester cleavage. These preferably include alcohols such as methanol, ethanol, n-propanol, iso-propanol, n-butanol or tert-butanol, or ethers such as diethyl ether, tetrahydrofuran, dioxane or glycol dimethyl ether, or other solvents such as acetone, dichloromethane, dimethylformamide or dimethyl sulfoxide. It is likewise possible to employ mixtures of the solvents mentioned. In the case of a basic ester hydrolysis, preferably mixtures of water with dioxane, tetrahydrofuran, methanol and/or ethanol are used, and in the case of nitrile hydrolysis preferably water or n-propanol is employed. Dichloromethane is preferably used in the case of reaction with trifluoroacetic acid, and tetrahydrofuran, diethyl ether, dioxane or water is preferably used in the case of reaction with hydrogen chloride.

Suitable bases are the usual inorganic bases. These preferably include alkali metal or alkaline earth metal hydroxides such as, for example, sodium, lithium, potassium or barium hydroxide, or alkali metal or alkaline earth metal carbonates such as sodium, potassium or calcium carbonate. Sodium, potassium or lithium hydroxide are particularly preferred.

Suitable acids for the ester cleavage are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, where appropriate with the addition of water. Preference is given to hydrogen chloride or trifluoroacetic acid in the case of the tert-butyl esters and to hydrochloric acid in the case of the methyl or ethyl esters.

The ester cleavage generally takes place in a temperature range from 0° C. to +100° C., preferably at +20° C. to +60° C. The nitrile hydrolysis is generally carried out in a temperature range from +50° C. to +150° C., preferably at +90° C. to +110° C.

The process sequence (XIV)→(XV)→(I-D) can where appropriate also be carried out as a one-pot reaction, in which the elimination of the protective group PG and the hydrolysis of the group T take place simultaneously. Suitable for this purpose are in particular strong acids or bases such as hydrogen chloride or trifluoroacetic acid, or sodium or potassium hydroxide.

The reactions mentioned can be carried out under atmospheric, elevated or reduced pressure (e.g. from 0.5 to 5 bar). They are generally carried out in each case under atmospheric pressure.

The compounds according to the invention of the formula (I) in which Y is a group of the formula

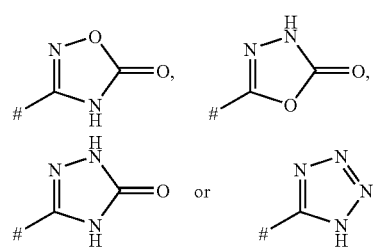

in which # means the respective point of linkage, can be prepared by

[B] converting compounds of the formula (XVI)

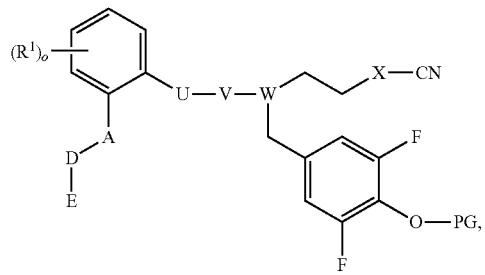
(XVI)

in which A, D, E, U, V, W, X, R¹, o and PG each have the meanings indicated above,
initially in an inert solvent with hydroxylamine into compounds of the formula (XVII)

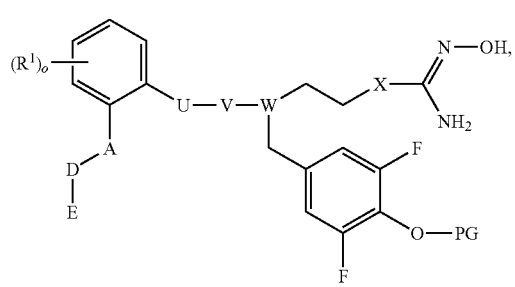
(XVII)

in which A, D, E, U, V, W, X, R¹, o and PG each have the meanings indicated above,
subsequently reacting in an inert solvent in the presence of a base with a chloroformic ester of the formula (XVIII)

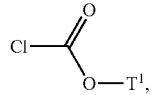
(XVIII)

in which
T¹ is $(C_1\text{-}C_{10})$-alkyl,
and where appropriate by subsequent heating in an inert solvent to give compounds of the formula (XIX)

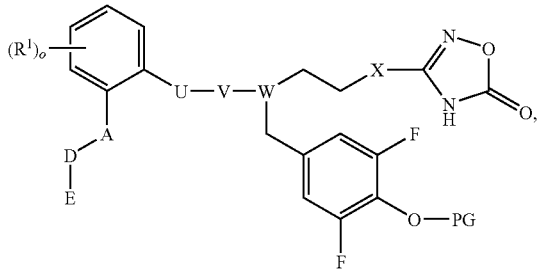
(XIX)

in which A, D, E, U, V, W, X, R¹, o and PG each have the meanings indicated above, and then converting by elimination of the protective group PG into compounds of the formula (I-E)

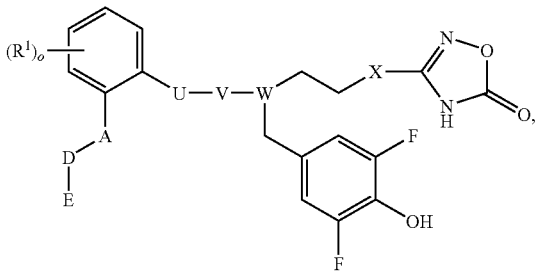
(I-E)

in which A, D, E, U, V, W, X, R¹ and o each have the meanings indicated above,

[C] converting compounds of the formula (XX)

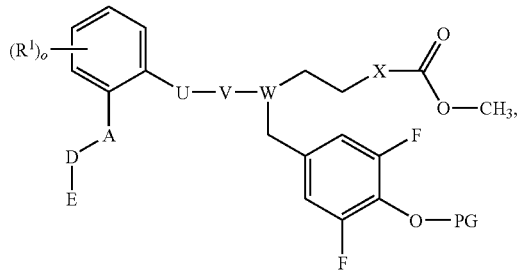
(XX)

in which A, D, E, U, V, W, X, R¹, o and PG each have the meanings indicated above,
initially in an inert solvent with hydrazine into compounds of the formula (XXI)

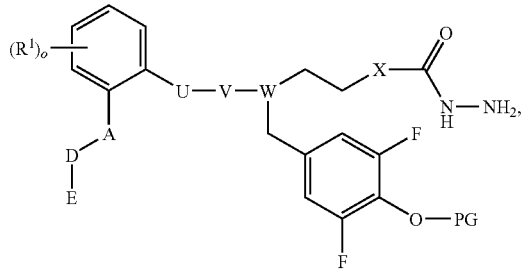
(XXI)

in which A, D, E, U, V, W, X, R¹, o and PG each have the meanings indicated above,
subsequently reacting in an inert solvent with phosgene or a phosgene derivative such as, for example, di- or triphosgene to give compounds of the formula (XXII)

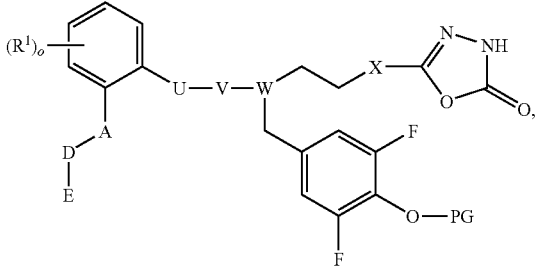
(XXII)

in which A, D, E, U, V, W, X, R¹, o and PG each have the meanings indicated above, and then converting by elimination of the protective group PG into compounds of the formula (I-F)

(I-F)

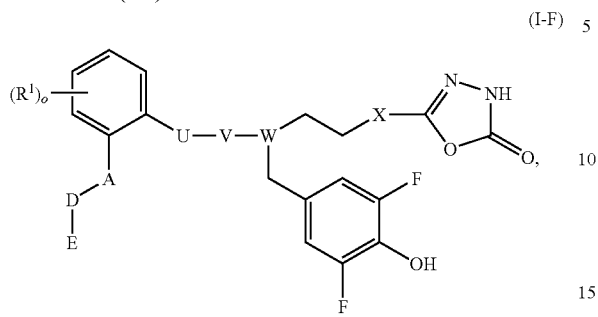

in which A, D, E, U, V, W, X, R¹ and o each have the meanings indicated above,

[D] converting compounds of the formula (XXI)

(XXIII)

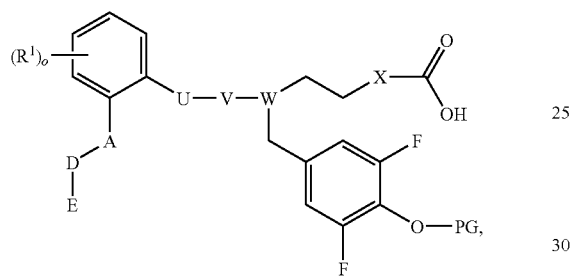

in which A, D, E, U, V, W, X, R¹, o and PG each have the meanings indicated above, initially in an inert solvent with oxalyl chloride, thionyl chloride or phosphoryl chloride into the corresponding carbonyl chlorides of the formula (XXIV)

(XXIV)

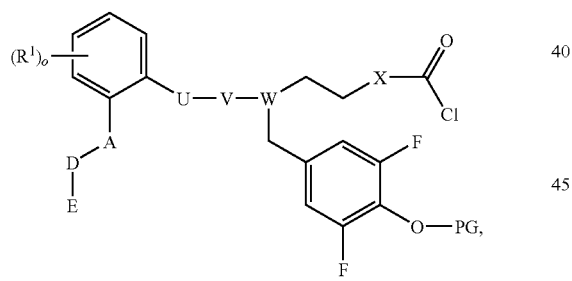

in which A, D, E, U, V, W, X, R¹, o and PG each have the meanings indicated above, then reacting the latter in an inert solvent with semicarbazide to give compounds of the formula (XXV)

(XXV)

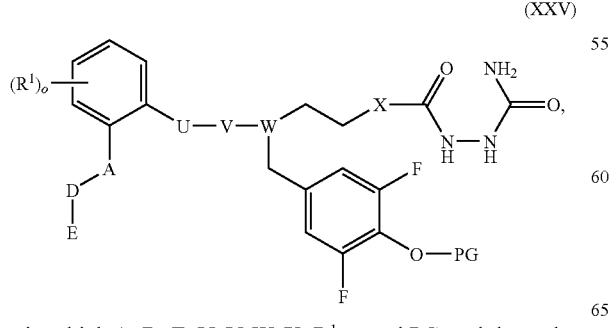

in which A, D, E, U, V, W, X, R¹, o and PG each have the meanings indicated above, subsequently cyclizing in the presence of a base to compounds of the formula (XXVI)

(XXVI)

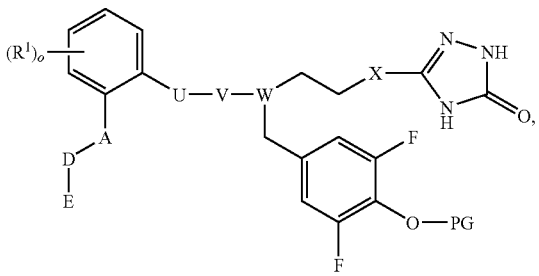

in which A, D, E, U, V, W, X, R¹, o and PG each have the meanings indicated above, and subsequently converting by elimination of the protective group PG into compounds of the formula (I-G)

(I-G)

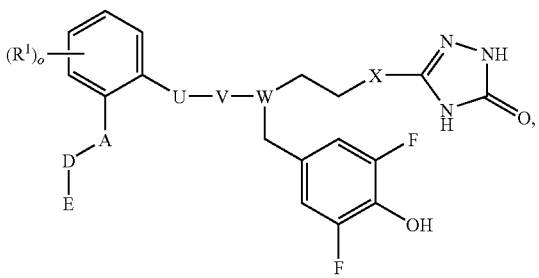

in which A, D, E, U, V, W, X, R¹ and o each have the meanings indicated above, or

[E] reacting compounds of the formula (XVI)

(XVI)

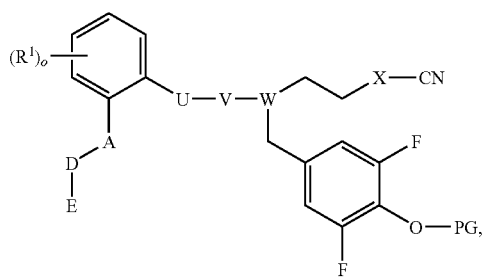

in which A, D, E, U, V, W, X, R¹, o and PG each have the meanings indicated above, in an inert solvent with an alkali metal azide in the presence of ammonium chloride or with trimethylsilyl azide where appropriate in the presence of a catalyst to give compounds of the formula (XXVII)

(XXVII)

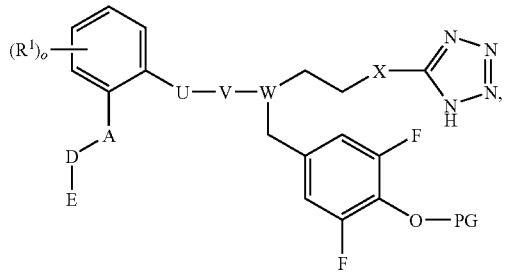

in which A, D, E, U, V, W, X, R¹, o and PG each have the meanings indicated above, and then converting by elimination of the protective group PG into compounds of the formula (I-H)

(I-H)

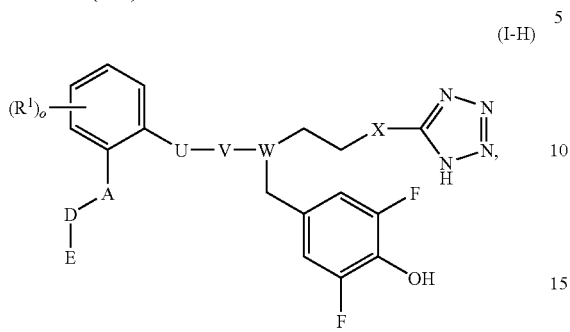

in which A, D, E, U, V, W, X, R¹ and o each have the meanings indicated above, and separating the respectively resulting compounds of the formulae (I-E), (I-F), (I-G) and (I-H) where appropriate by methods known to the skilled worker into their enantiomers and/or diastereomers, and/or where appropriate reacting with the appropriate (i) solvents and/or (ii) bases or acids to give the solvates, salts and/or solvates of the salts thereof.

The starting compounds (XVI) and (XX) used in process sequences [B], [C], [D], [E] correspond to the compounds of the formulae (IV-A), (IV-B), (IV-C) and (XIV) described above.

The compounds according to the invention of the formula (I) in which U, V and W together form a group of the formula *-CH₂—CH₂—CH<, in which * means the point of linkage to the phenyl ring, can be prepared by hydrogenation of the olefinic double bond at the stage of the compounds (IV-A), (IV-B), (IV-C), (VI) or (1-C) and further reaction in analogy to the processes described above.

The compounds of the formulae (V), (VII), (VIII), (XI-A), (XI-B), (XII) and (XVIII) are commercially available, disclosed in the literature or can be prepared by processes disclosed in the literature (see also reaction schemes 1, 2 and 10 below).

The preparation of the compounds of the invention can be illustrated by the following synthesis schemes:

Scheme 1

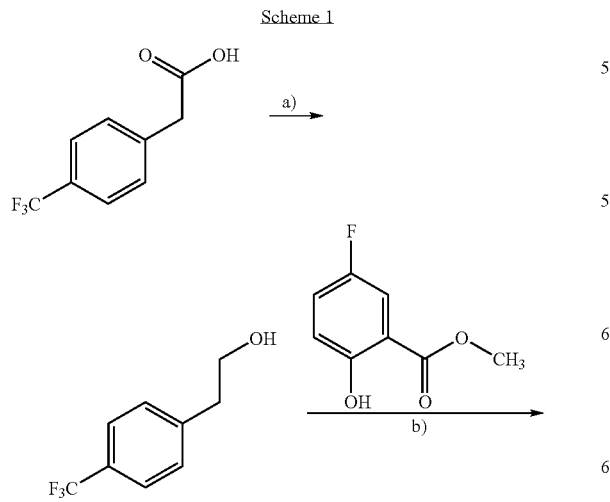

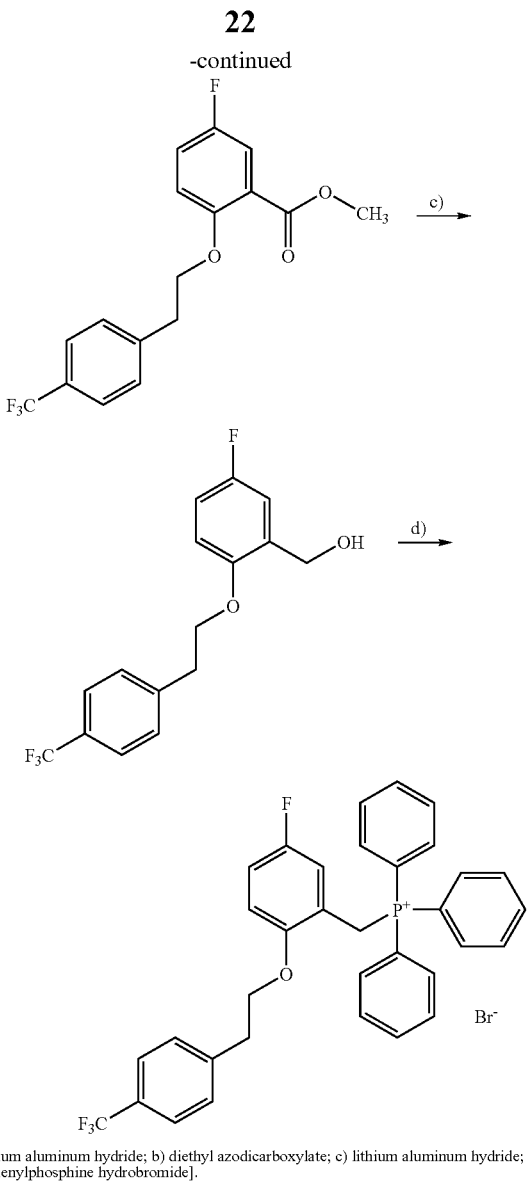

[a) lithium aluminum hydride; b) diethyl azodicarboxylate; c) lithium aluminum hydride; d) triphenylphosphine hydrobromide].

Scheme 2

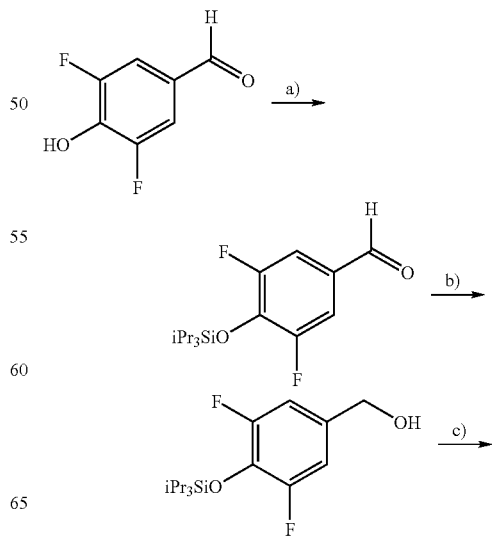

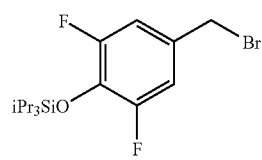

[a) triisopropylsilyl trifluoromethanesulfonate; b) sodium borohydride; c) tetrabromomethane, triphenylphosphine].

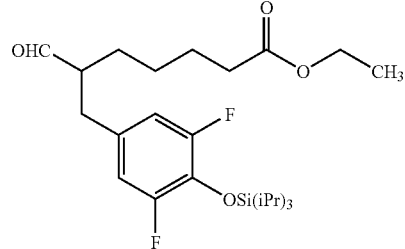

[a) sodium hydride; b) palladium (II) acetate, triphenylphosphine, triethylamine, formic acid; c) borane-THF complex; d) N-methylmorphine N-oxide, tetrapropylammonium perruthenate].

Scheme 3

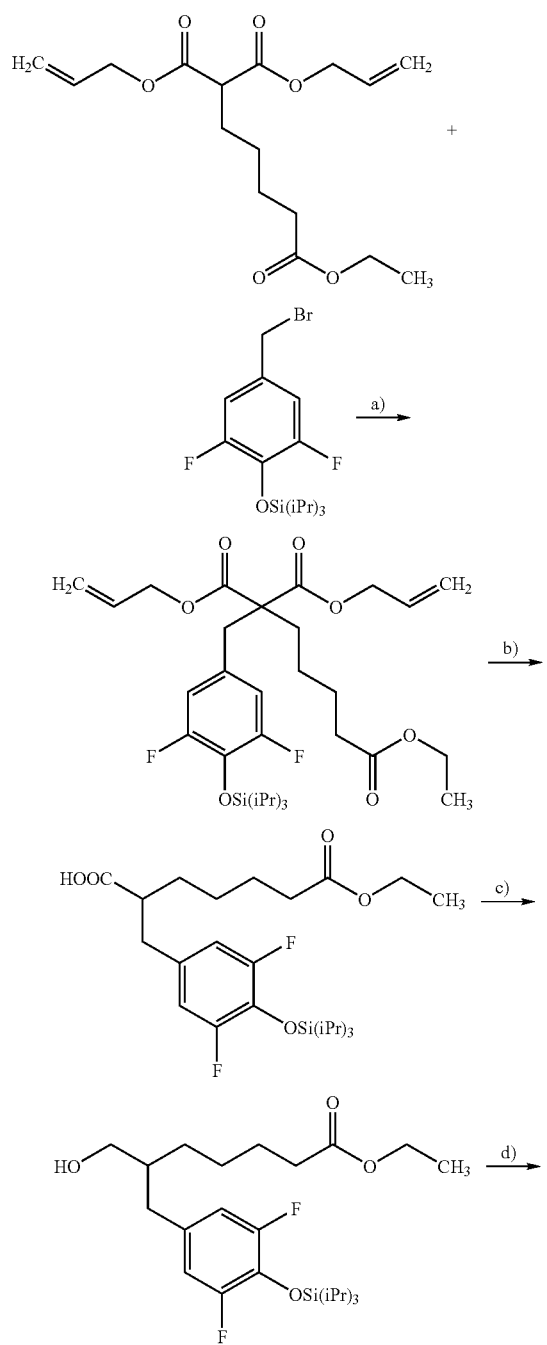

Scheme 4

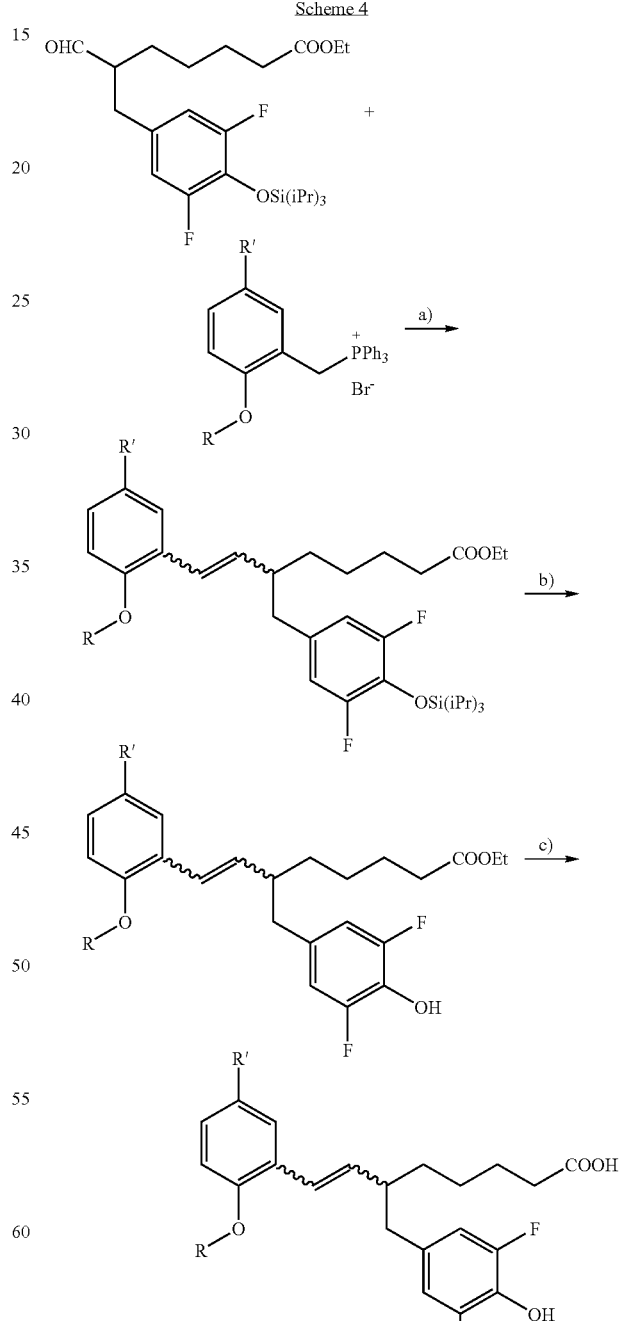

[a) n-butyllithium; b) tetra-n-butylammonium fluoride; c) sodium hydroxide solution].

Scheme 5
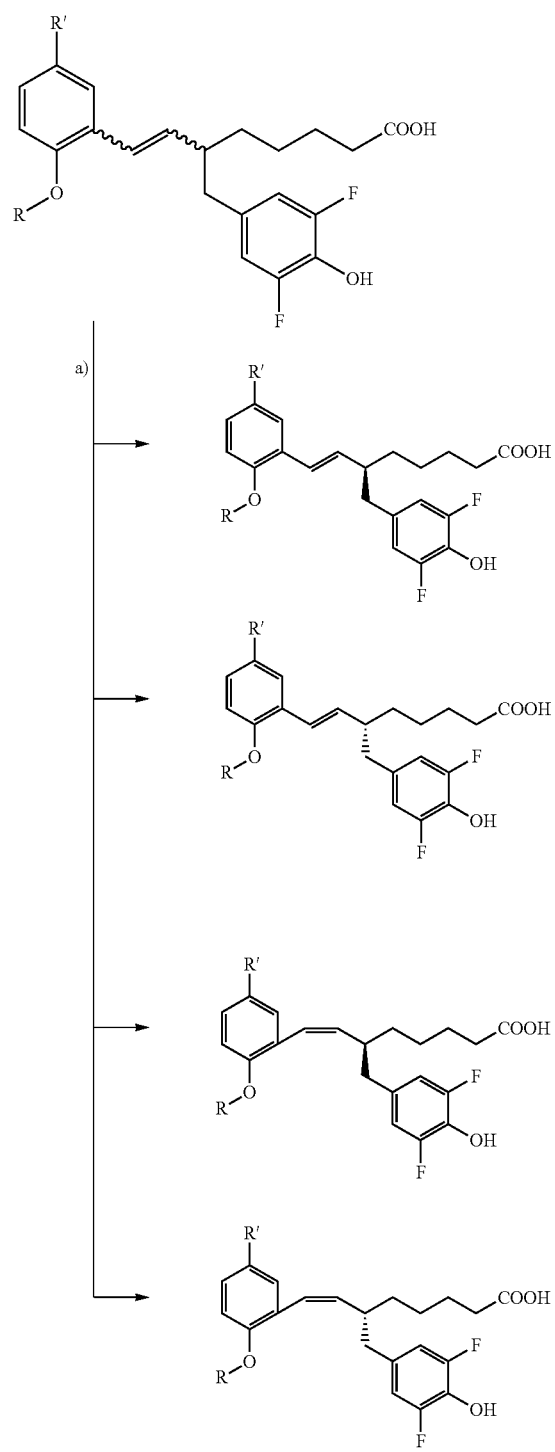
[a) preparative HPLC on chiral phase].
Scheme 6
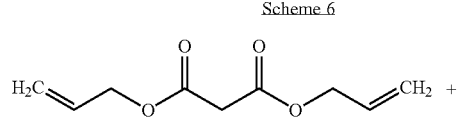
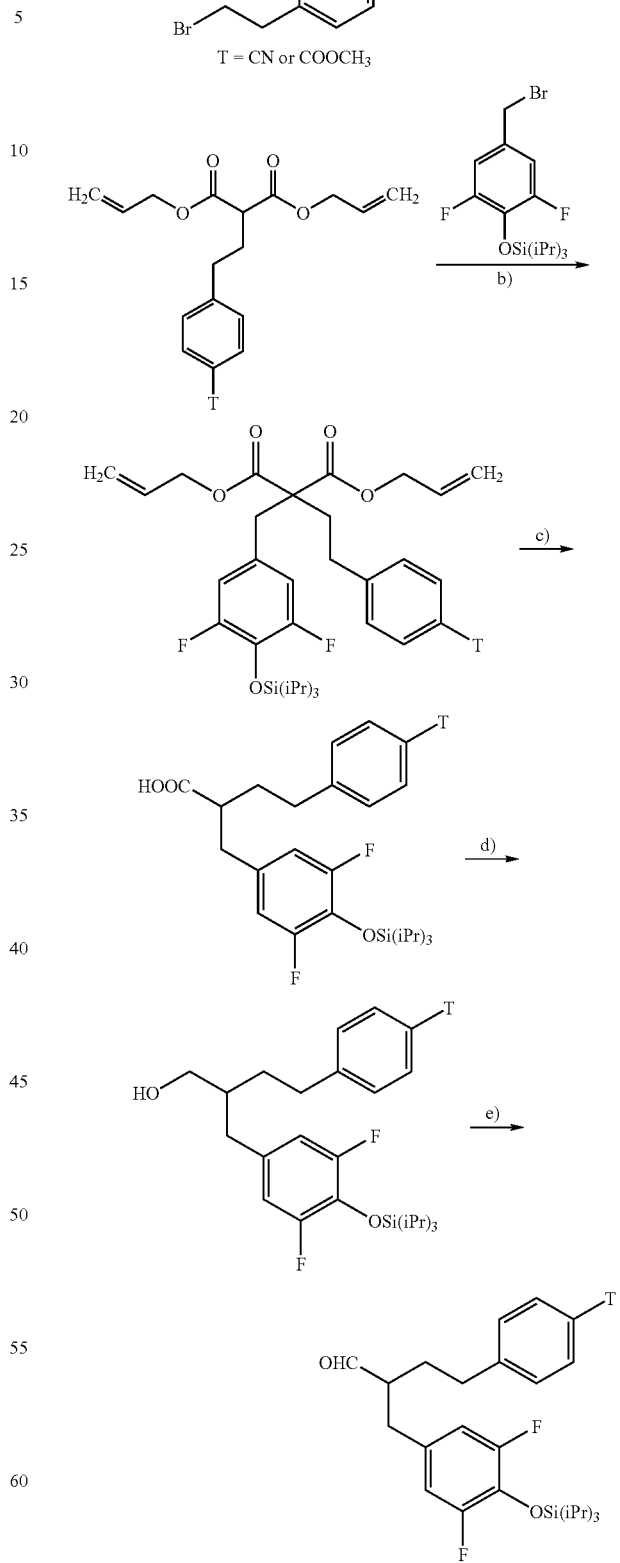
[a) sodium hydride; b) sodium hydride; c) palladium (II) acetate, triphenylphosphine, triethylamine, formic acid; d) borane-THF complex; e) pyridinium chlorochromate].

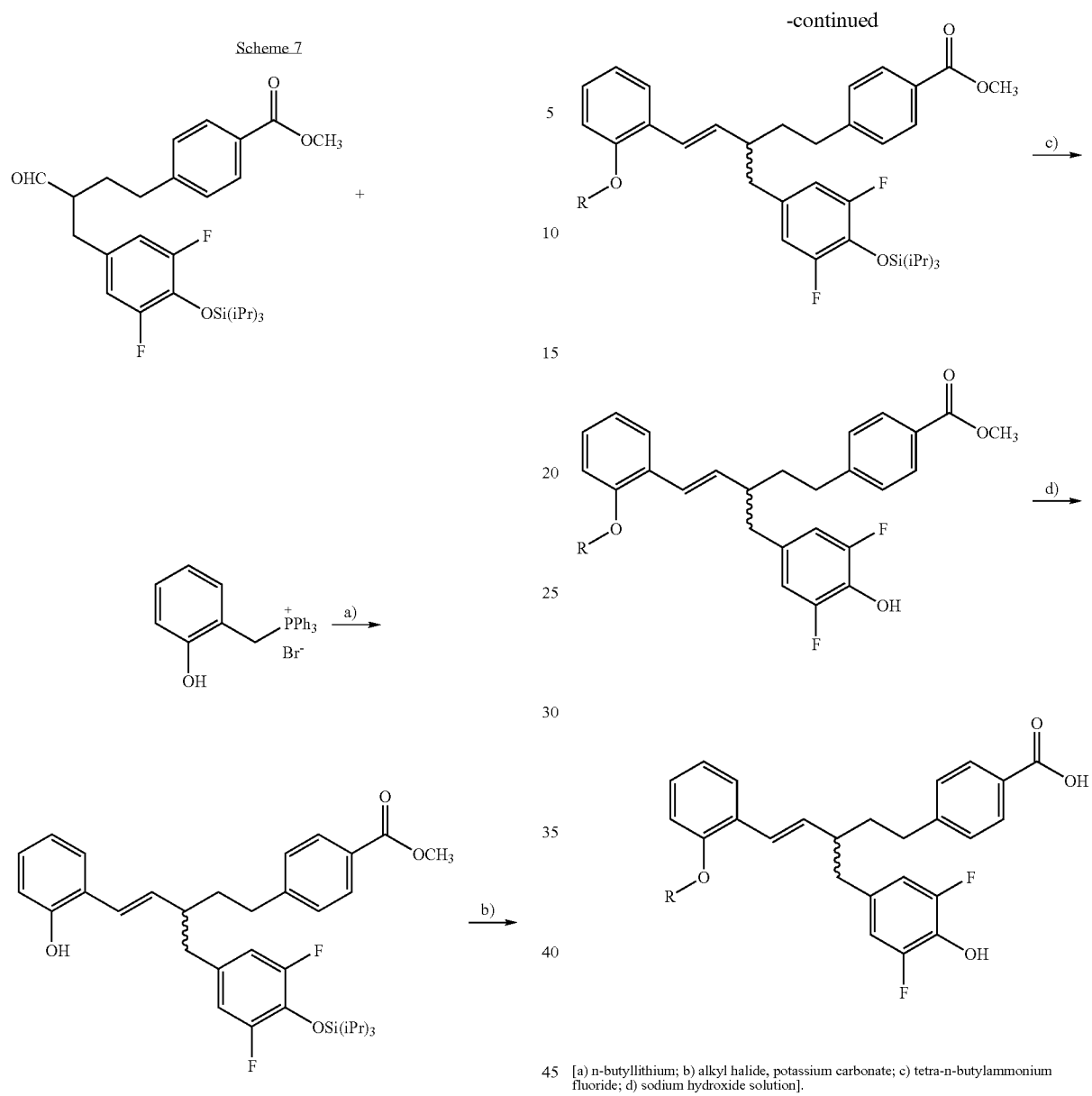
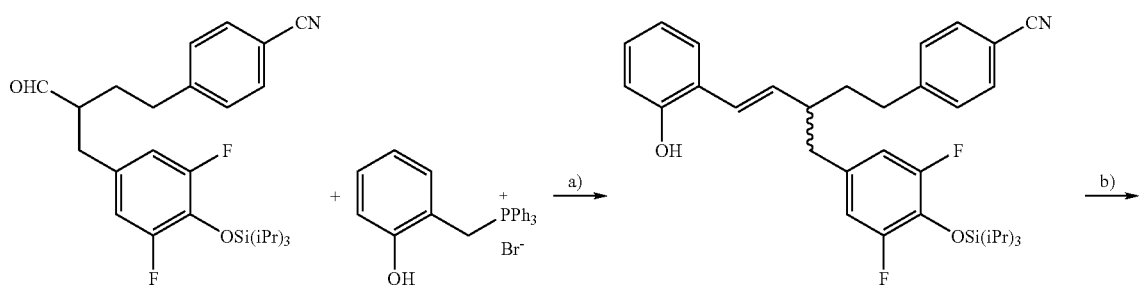
[a) n-butyllithium; b) alkyl halide, potassium carbonate; c) tetra-n-butylammonium fluoride; d) sodium hydroxide solution].

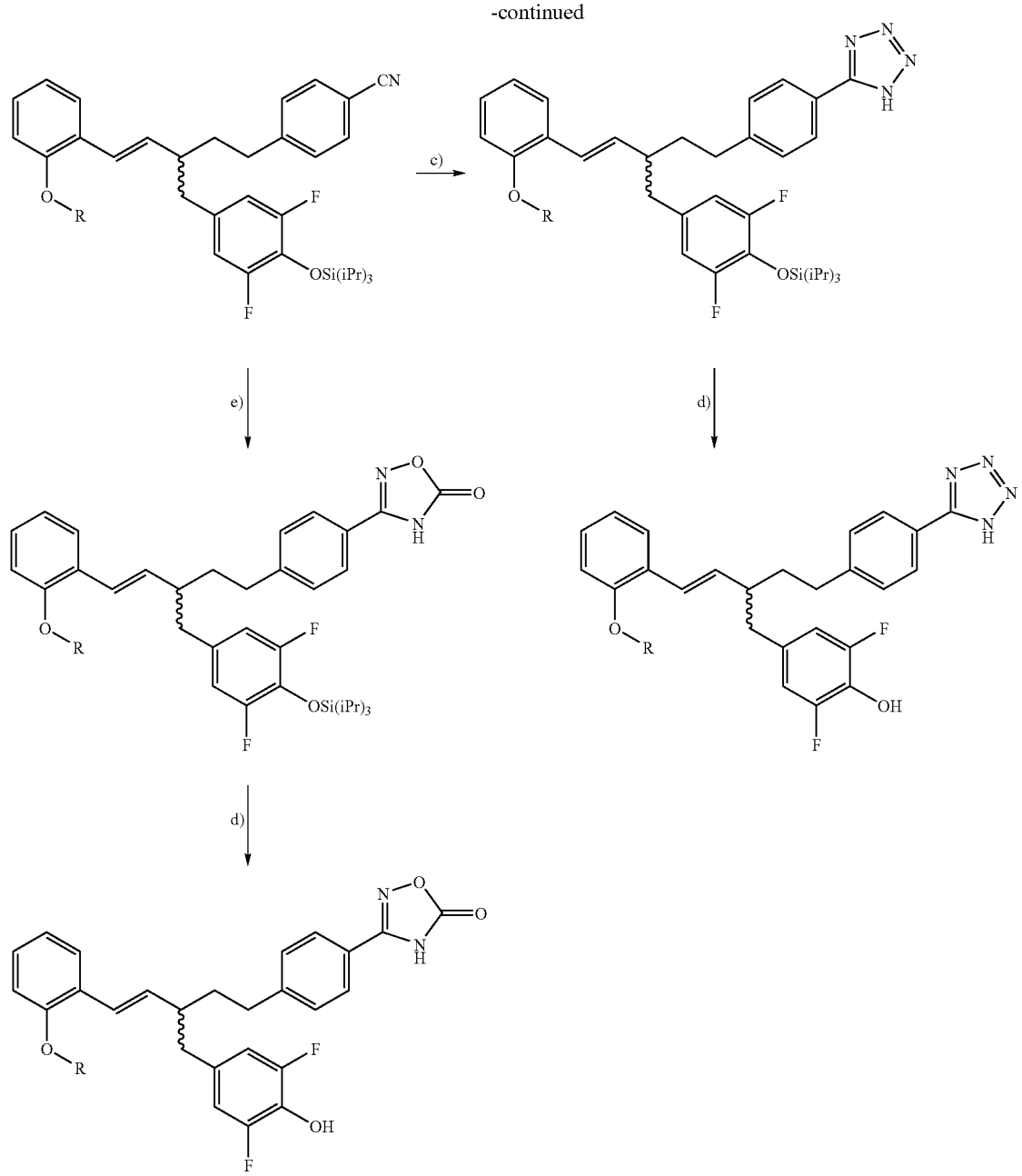
[a) n-butyllithium; b) alkyl halide, potassium carbonate; c) trimethylsilyl azide, di-n-butyltin oxide; d) tetra-n-butylammonium fluoride; e) 1. hydroxylamine hydrochloride, 2. 2-ethylhexyl chloroformate].
Scheme 9

31

-continued

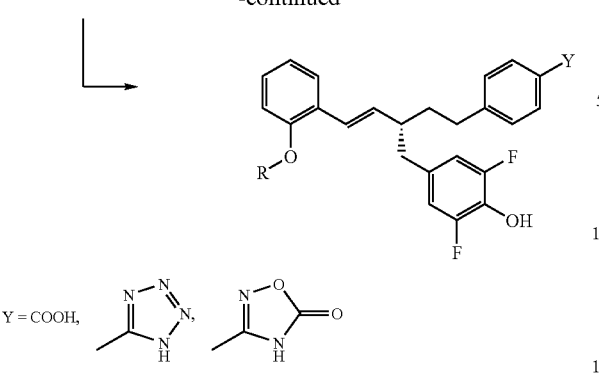

Y = COOH, [tetrazole], [oxadiazolone]

[a) preparative HPLC on chiral phase].

Scheme 10

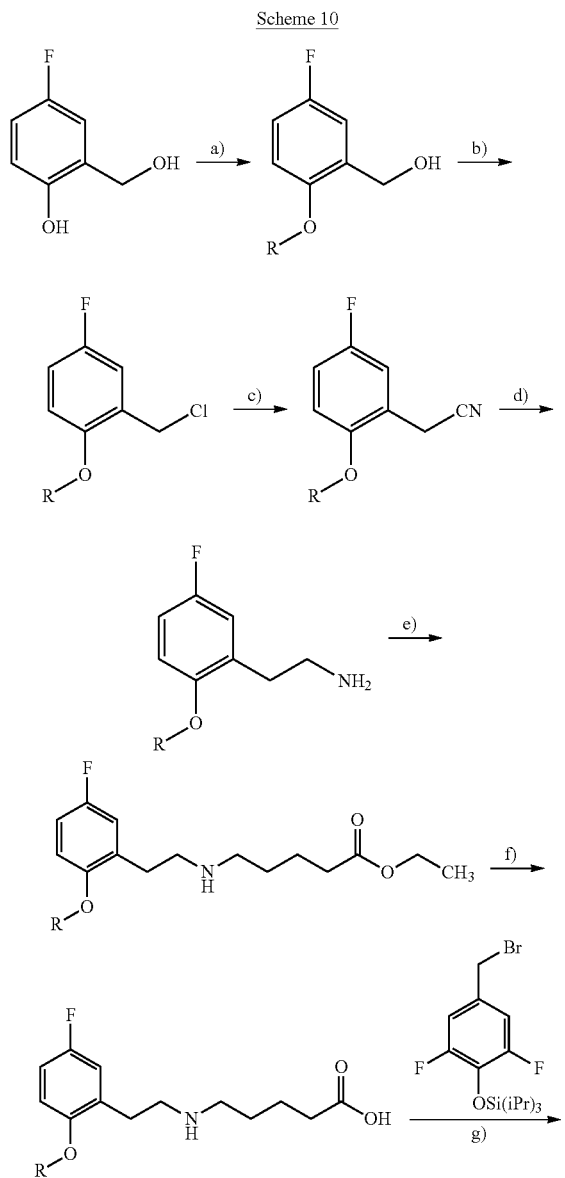

32

-continued

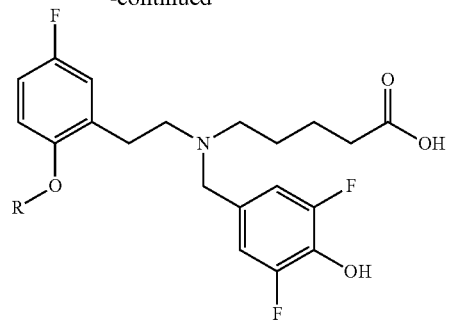

[a) alkyl halide, potassium carbonate; b) thionyl chloride; c) sodium cyanide; d) aluminum trichloride, lithium aluminum hydride; e) ethyl bromovalerate, triethylamine; f) hydrochloric acid; g) potassium carbonate].

[Abbreviations: Et=ethyl; iPr=isopropyl; Ph=phenyl; THF=tetrahydrofuran].

The compounds according to the invention have valuable pharmacological properties and can be used for the prevention and treatment of disorders in humans and animals.

The compounds of the present invention exhibit, as particular and surprising feature, advantageous pharmacokinetic properties such as, for example, an increased bioavailability and/or a prolonged duration of action after oral administration.

The compounds according to the invention lead to vasorelaxation, to an inhibition of platelet aggregation and to a reduction in blood pressure, and to an increase in coronary blood flow. These effects are mediated by direct activation of soluble guanylate cyclase and an intracellular increase in cGMP.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemias such as myocardial infarction, stroke, transistoric and ischemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, CREST syndrome, erythematosis, onychomycosis and rheumatic disorders.

The compounds according to the invention are furthermore suitable for the treatment of respiratory distress syndromes and chronic obstructive airway disorders (COPD), of acute and chronic renal failure and for promoting wound healing.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Examples of suitable combination active ingredients which may be preferably mentioned are:
  organic nitrates and NO donors such as, for example, sodium nitroprusside, nitroglycerin, isosorbide mononitrate, isosorbide dinitrate, molsidomine or SIN-1, and inhaled NO;
  compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
  NO-independent but heme-dependent stimulators of guanylate cyclase, such as, in particular, the compounds described in WO 00/06568, WO 00/06569, WO 02/42301 and WO 03/095451;
  agents having antithrombotic activity, for example and preferably from the group of platelet aggregation inhibitors, of anticoagulants or of profibrinolytic substances;
  active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
  active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, BAY 59-7939, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein(a) antagonists.

In a preferred embodiment of the invention, the compounds according to the invention are administered in combination with a CETP inhibitor such as, for example and preferably, torcetrapib (CP-529 414), JJT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, Cholesta-Gel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilisates or sterile powders.

Suitable for the other administration routes are, for example, pharmaceutical forms for inhalation (inter alia powder inhalers, nebulizers), nasal drops, solutions or sprays;

tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations abs. Absolute
aq. Aqueous
CI Chemical ionization (in MS)
DCI Direct chemical ionization (in MS)
DEAD Diethyl azodicarboxylate
DMF Dimethylformamide
DMSO Dimethyl sulfoxide
ee Enantiomeric excess
EI Electron impact ionization (in MS)
eq. Equivalent(s)
ESI Electrospray ionization (in MS)
Ex. Example
GC Gas chromatography
h Hour(s)
HPLC High pressure, high performance liquid chromatography
LC/MS Coupled liquid chromatography-mass spectroscopy
Min Minute(s)
MS Mass spectroscopy
NMR Nuclear magnetic resonance spectroscopy
$R_f$ Retention index (in TLC)
RT Room temperature
$R_t$ Retention time (in HPLC)
THF Tetrahydrofuran
TLC Thin-layer chromatography
UV Ultraviolet spectroscopy
v/v Volume to volume ratio (of a solution)

LC/MS Methods:

Method 1 (LC-MS)

MS instrument type: Micromass ZQ; HPLC instrument type: HP 1100 series, UV DAD; column: Phenomenex Synergi 2µ Hydro-RP Mercury 20 mm×4 mm; eluent A: 1 l of water+0.5 ml of 50% formic acid, eluent B: 1l l of acetonitrile+0.5 ml of 50% formic acid; gradient: 0.0 min 90% A→2.5 min 30% A→3.0 min 5% A→4.5 min 5% A; flow rate: 0.0 min 1 ml/min →2.5 min/3.0 min/4.5 min 2 ml/min; oven: 50° C.; UV detection: 210 nm.

Method 2 (LC-MS)

MS instrument type: Micromass ZQ; HPLC instrument type: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A →2.5 min 30% A→3.0 min 5% A→4.5 min 5% A; flow rate: 0.0 min 1 ml/min →2.5 min/3.0 min/4.5 min 2 ml/min; oven: 50° C.; W detection: 210 nm.

Method 3 (LC-MS)

Instrument: Micromass Quattro LCZ with HPLC Agilent Series 1100; column: Phenomenex Synergi 2I1 Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 4 (LC-MS)

MS instrument type: Micromass ZQ; HPLC instrument type: Waters Alliance 2795; column: Merck Chromolith SpeedROD RP-18e 50 mm×4.6 mm; eluent A: water+500 µl of 50% formic acid/l, eluent B: acetonitrile+500 µl of 50% formic acid/l; gradient: 0.0 min 10% B→3.0 min 95% B→4.0 min 95% B; oven: 35° C.; flow rate: 0.0 min 1.0 ml/min →3.0 min 3.0 ml/min →4.0 min 3.0 ml/min; UV detection: 210 nm.

Method 5 (LC-MS)

MS instrument type: Micromass ZQ; HPLC instrument type: Waters Alliance 2790; column: Symmetry C 18, 50 mm×2.1 mm, 3.5 µm; eluent B: acetonitrile+0.05% formic acid, eluent A: water+0.05% formic acid; gradient: 0.0 min 10% B→3.5 min 90% B→5.5 min 90% B; oven: 50° C.; flow rate: 0.8 ml/min; UV detection: 210 nm.

GC/MS Methods:

Method 1 (GC-MS)

Instrument: Micromass GCT, GC6890; column: Restek RTX-35MS, 30 m×250 µm×0.25 µm; constant helium flow: 0.88 ml/min; oven: 60° C.; inlet: 250° C.; gradient: 60° C. (hold for 0.30 min), 50° C./min→120° C., 16° C./min→250° C., 30° C./min→300° C. (hold for 1.7 min).

Method 2 (GC-MS)

Instrument: Micromass GCT, GC6890; column: Restek RTX-35MS, 30 m×250 µm×0.25 µm; constant helium flow: 0.88 ml/min; oven: 60° C.; inlet: 250° C.; gradient: 60° C. (hold for 0.30 min), 50° C./min →120° C., 16° C./min →250° C., 30° C./min →300° C. (hold for 8.7 min).

HPLC Methods:

Method 1 (HPLC)

Instrument: HP 1100 with DAD detection; column: Kromasil 100 RP-18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→9 min 90% B→9.2 min 2% B→10 min 2% B; flow rate: 0.75 ml/min; column temperature: 30° C.; UV detection: 210 nm.

Method 2 (HPLC)

Instrument: HP 1100 with DAD detection; column: Kromasil 100 RP -18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 3 (HPLC)

Instrument: HP 1100 with DAD detection; column: Kromasil 100 RP-18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→15 min 90% B→15.2 min 2% B→16 min 2% B; flow rate: 0.75 ml/min; column temperature: 30° C.; UV detection: 210 nm.

Method 4 (HPLC)

Instrument: HP 1100 with DAD detection; column: Kromasil 100 RP-18, 60 mm×2.1 mm, 3.5 µm; eluent A: 5 ml of HClO$_4$ (70%)/l of water, eluent B: acetonitrile; gradient: 0 min 2% B→0.5 min 2% B→4.5 min 90% B→30.0 min 90% B→30.2 min 2% B→32 min 2% B; flow rate: 0.75 ml/min; column temperature: 30° C.; UV detection: 210 nm.

Starting Compounds and Intermediates

Example 1A 2-(4-Trifluoromethylphenyl)ethanol

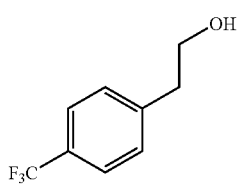

3.0 g (14.7 mmol) of 4-trifluoromethylphenylacetic acid are introduced into 30 ml of abs. THF at 0° C., then a 1 M solution of 557 mg (14.7 mmol) of lithium aluminum hydride in 14.7 ml of THF is added dropwise, and the solution is stirred at room temperature until reaction is complete. The mixture is added to ice, acidified with hydrochloric acid and extracted with ethyl acetate. The organic phase is concentrated, and the crude product is purified by chromatography on silica gel. 2 g (92% of theory) of the title compound are obtained.

$^1$H-NMR (400 MHz, CDCl$_3$, δ/ppm): 2.95 (t, 2H), 3.9 (t, 2H), 7.35 (d, 2H), 7.6 (t, 2H).

GC-MS (method 1): R$_t$ 4.61 min; m/z 190 (M$^+$).

Example 2A

Methyl 5-fluoro-2-[2-(4-trifluoromethylphenyl)ethoxy]benzoate

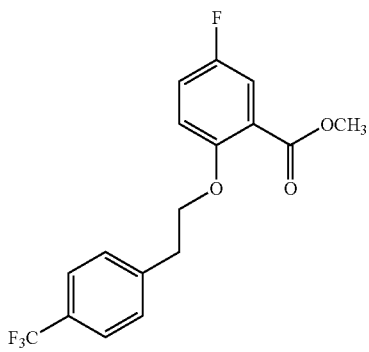

1.79 g (10.5 mmol) of methyl 5-fluorosalicylate, 20 g (10.5 mmol) of 2-(4-trifluoromethyl-phenyl)ethanol and 2.76 g (10.5 mmol) of triphenylphosphine are introduced into 50 ml of THF and, at 0° C., a solution of 1.83 g (10.5 mmol) of DEAD in 10 ml of THF is added dropwise. The mixture is stirred at RT overnight and the volatile components are then removed in vacuo. The resulting crude product is purified by chromatography on silica gel (mobile phase: cyclohexane/ethyl acetate 7:1). 2.09 g (58% of theory) of the title compound are obtained.

$^1$H-NMR (300 MHz, CDCl$_3$, δ/ppm): 3.2 (t, 2H), 3.85 (s, 3H), 4.25 (t, 2H), 6.85 (dd, 1H), 7.15 (m, 1H), 7.5 (m, 3H), 7.6 (d, 2H).

GC-MS (method 2): R$_t$ 10.54 min; m/z 342 (M$^+$).

Example 3A

5-Fluoro-2-[2-(4-trifluoromethylphenyl)ethoxy]benzyl alcohol

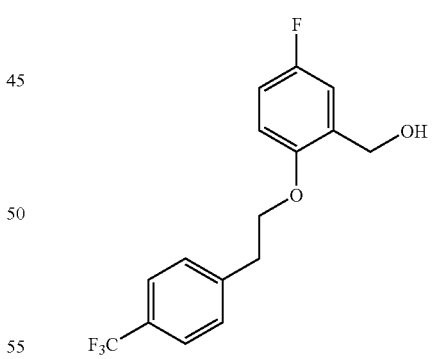

2.0 g (5.84 mmol) of methyl 5-fluoro-2-[2-(4-trifluoromethylphenyl)ethoxy]benzoate are introduced into 25 ml of THF, then at 0° C., 4.38 ml (4.38 mmol) of a 1 M solution of lithium aluminum hydride in THF are added dropwise, and the mixture is stirred at RT until reaction is complete. The mixture is added to ice-water, acidified with hydrochloric acid and extracted with ethyl acetate. All the volatile components are removed in vacuo, and the crude product is purified by chromatography on silica gel (mobile phase: cyclohexane/ethyl acetate 5:1). 1.7 g (82% of theory) of the title compound are obtained.

$^1$H-NMR (400 MHz, CDCl$_3$, δ/ppm): 3.2 (t, 2H); 4.25 (t, 2H); 4.6 (s, 2H); 6.75 (m, 1H); 6.9 (m, 1H); 7.05 (dd, 1H); 7.4 (d, 2H); 7.6 (d, 2H).

GC-MS (method 1): R$_t$ 10.71 min; m/z 314 (M$^+$).

Example 4A

{5-Fluoro-2-[2-(4-trifluoromethylphenyl)ethoxy]benzyl}triphenylphosphonium bromide

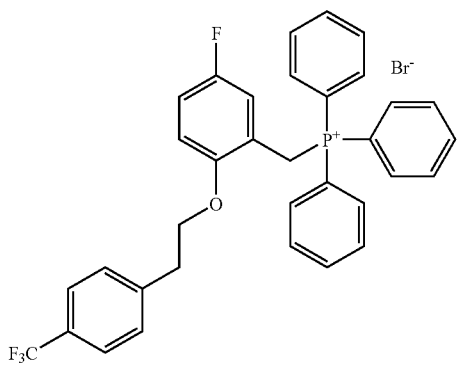

1.7 g (5.41 mmol) of 5-fluoro-2-[2-(4-trifluoromethylphenyl)ethoxy]benzyl alcohol and 1.76 g (5.14 mmol) of triphenylphosphine hydrobromide are heated under reflux in 20 ml of acetonitrile for three hours. A first product fraction is crystallized out. The mother liquor is concentrated, the residue is dissolved in dichloromethane, and a second fraction is crystallized with diethyl ether. A total of 2.71 g (76% of theory) of the title compound is obtained.

$^1$H-NMR (400 MHz, DMSO-d$_6$, δ/ppm): 2.75 (t, 2H); 3.75 (t, 2H); 4.85 (d, 2H); 6.8 (m, 1H); 6.9 (m, 1H); 7.15 (m, 1H); 7.45 (d, 2H); 7.6 (m, 8H); 7.7 (m, 6H); 7.9 (t, 3H).

LC-MS (method 2): R$_t$ 2.15 min; m/z 559 [M+H]$^+$.

Example 5A

Methyl 2-(2-chlorobenzyloxy)-5-fluorobenzoate

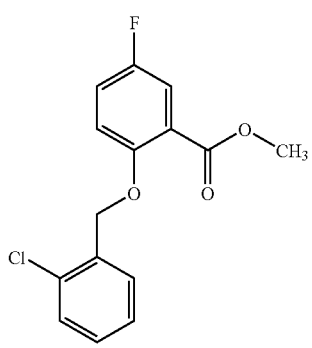

10.0 g (58 mmol) of methyl 5-fluoro-2-hydroxybenzoate [CAS 391-92-4], 13.3 g (64.5 mmol) of 2-chlorobenzyl bromide [CAS 611-17-6], 40.6 g (293 mmol) of potassium carbonate and 14.6 g (88 mmol) of potassium iodide are dissolved in 50 ml of acetone, and stirred under reflux for 12 h. The solvent is distilled out in vacuo, and the residue is taken up in ethyl acetate and washed twice each with 10% strength sodium hydroxide solution, 1 N hydrochloric acid and water. Drying over magnesium sulfate, filtration and washing with ethyl acetate are followed by concentration. The residue is stirred with petroleum ether, and the solid is filtered off with suction and dried on a clay dish. 10.0 g (33.9 mmol, 59% of theory) of the title compound are obtained.

$^1$H-NMR (400 MHz, DMSO-d$_6$, δ/ppm): 3.81 (s, 3H), 5.22 (s, 2H), 7.31 (dd, 1H), 7.36-7.46 (m, 3H), 7.51 (m$_c$, 2H), 7.72 (m$_c$, 1H).

LC-MS (method 2): R$_t$ 2.6 min; m/z 295 (M+H)$^+$.

Example 6A 2-(2-Chlorobenzyloxy)-5-fluorobenzoic acid

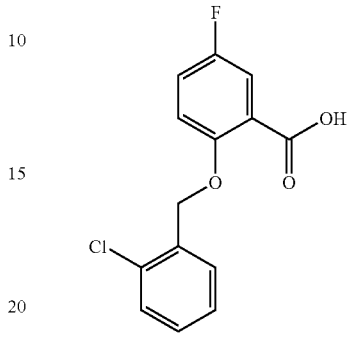

10.0 g (34 mmol) of methyl 2-(2-chlorobenzyloxy)-5-fluorobenzoate are dissolved in 80 ml of methanol and 40 ml of 40% strength sodium hydroxide solution and stirred at RT for 12 h. The solvent is distilled out in vacuo, water is added to the residue until it has all dissolved, and the solution is then extracted with ethyl acetate. The aqueous phase is acidified with hydrochloric acid and extracted three times with ethyl acetate. The mixture is dried over magnesium sulfate, filtered, washed with ethyl acetate and concentrated. The residue is mixed with petroleum ether, and the crystals which have separated out are filtered off with suction and dried on a clay dish. 6.00 g (21.3 mmol, 63% of theory) of the title compound are obtained.

$^1$H-NMR (400 MHz, DMSO-d$_6$, δ/ppm): 4.55 (d, 2H), 5.16 (s, 2H), 5.19 (t, 1H), 6.97-7.08 (m, 2H), 7.17 (dd, 1H), 7.42-7.37 (m, 2H), 7.51 (m$_c$, 1H), 7.61 (m$_c$, 1H).

HPLC (method 2): R$_t$ 4.6 min.

MS (DCI): 284 (M+NH$_4^+$).

Example 7A 2-(2-Chlorobenzyloxy)-5-fluorobenzyl alcohol

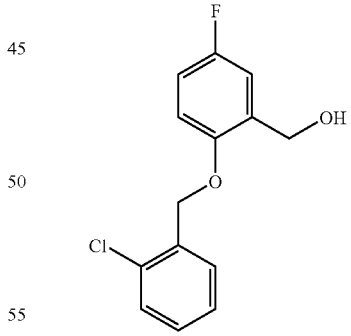

5.50 g (20 mmol) of 2-(2-chlorobenzyloxy)-5-fluorobenzoic acid are dissolved in 25 ml of THF, heated to reflux and then 20 ml of 1 M borane-dimethyl sulfide complex are added dropwise. The mixture is then cooled to room temperature and stirred at this temperature for 1 h. The solvent is distilled out in vacuo, and water is added to the residue. Acidification is then carried out cautiously (copious gas evolution) with 1 N hydrochloric acid. 1 N sodium hydroxide solution is then added to make slightly basic, and the aqueous phase is extracted three times with dichloromethane. The organic phases are dried over magnesium sulfate, filtered and washed with dichloromethane, and concentrated. Petroleum ether is added to the residue, and the crystals which have separated out are filtered off with suction and dried on a clay dish. 3.65 g (13.6 mmol, 68% of theory) of the title compound are obtained.

$^1$H-NMR (400 MHz, DMSO-d$_6$, δ/ppm): 4.55 (d, 2H), 5.16 (s, 2H), 5.19 (t, 1H), 6.97-7.08 (m, 2H), 7.17 (dd, 1H), 7.37-7.42 (m, 2H), 7.51 (m$_c$, 1H), 7.61 (m$_c$, 1H).

HPLC (method 2): R$_t$ 4.6 min.

MS (DCI): 284 (M+NH$_4^+$).

Example 8A

[2-(2-Chlorobenzyloxy)-5-fluorobenzyl]triphenylphosphonium bromide

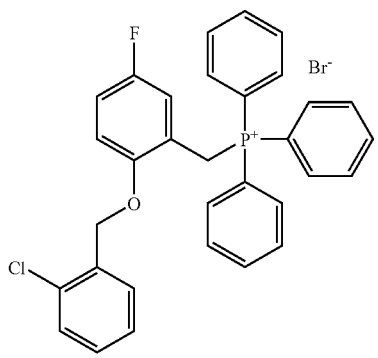

4.60 g (17 mmol) of 2-(2-chlorobenzyloxy)-5-fluorobenzyl alcohol are dissolved in 10 ml of acetonitrile, then 5.62 g (16 mmol) of triphenylphosphine hydrobromide are added, and the suspension is stirred under reflux for 12 h. A further 2.80 g (8 mmol) of triphenylphosphine hydrobromide are added, and the mixture is stirred under reflux for a further 3 h. The solvent is mostly distilled out in vacuo, the crystals which have separated out are stirred with petroleum ether, filtered off with suction and dried on a clay dish. 9.82 g (15.7 mmol, 92% of theory) of the title compound are obtained.

$^1$H-NMR (300 MHz, DMSO-d$_6$, δ/ppm): 4.66 (d, 2H), 4.99 (d, 2H), 6.90 (dt, 1H), 6.96 (dd, 1H), 7.15 (m, 1H), 7.30-7.42 (m, 3H), 7.46-7.70 (m, 13H), 7.86 (m$_c$, 3H).

HPLC (method 1): R$_t$ 5.0 min.

MS (ESI): 511 (M−Br$^+$).

Example 9A

Ethyl 4'-trifluoromethylbiphenyl-4-carboxylate

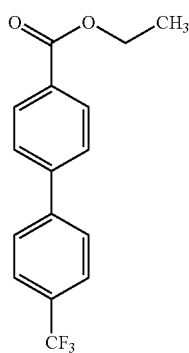

7.00 g (30.6 mmol) of ethyl 4-bromobenzoate are dissolved in 60 ml of 1,2-dimethoxyethane and, under argon, 6.96 g (36.7 mmol) of 4-trifluoromethylphenylboronic acid, 271 mg of bis(triphenyl-phosphine)palladium(II) chloride and 40.7 ml of a 2 M aqueous sodium carbonate solution are added. The reaction mixture is then stirred under reflux for 12 hours. The mixture is subsequently cooled, filtered through 1 g of Extrelute, washed with dichloromethane and the solvent is removed in vacuo. The resulting crude product is purified by flash chromatography on silica gel 60 (mobile phase: cyclohexane/dichloromethane 2:1). 6.31 g (21.4 mmol, 70% of theory) of the title compound are obtained.

$^1$H-NMR (300 MHz, CDCl$_3$, δ/ppm): 1.43 (t, 3H), 4.41 (q, 2H), 7.67 (d, 2H), 7.72 (s, 4H), 8.17 (d, 2H).

MS (EI): 294 (M$^+$).

Example 10A (4'-Trifluoromethylbiphenyl-4-yl)methanol

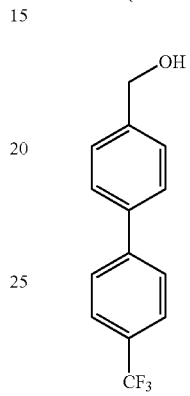

12.7 ml (12.7 mmol) of a 1 M lithium aluminum hydride solution in THF are slowly added to a solution of 6.24 g (21.2 mmol) of ethyl 4'-trifluoromethylbiphenyl-4-carboxylate in 60 ml of dry THF at 0° C. After the reaction is complete, the mixture is hydrolyzed with saturated ammonium chloride solution and taken up in ethyl acetate, and the organic phase is separated off and dried over sodium sulfate. After filtration, the solvent is removed in vacuo. The resulting crude product is purified by flash chromatography on silica gel 60 (mobile phase: cyclohexane/ethyl acetate 5:1). 5.10 g (20.2 mmol, 95% of theory) of the title compound are obtained.

$^1$H-NMR (300 MHz, DMSO-d$_6$, δ/ppm): 4.58 (d, 2H), 5.23 (t, 2H), 7.46 (d, 2H), 7.71 (d, 2H), 7.82 (d, 2H), 7.88 (d, 2H).

MS (EI): 252 (M$^+$).

Example 11A

4-Chloromethyl-4'-trifluoromethylbiphenyl

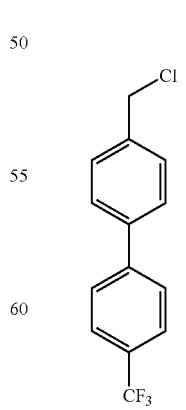

A solution of 5.00 g (19.8 mmol) of (4'-trifluoromethylbiphenyl-4-yl)methanol in 40 ml of chloroform is mixed with 2.89 ml (39.7 mmol) of thionyl chloride dissolved in 10 ml of chloroform, and the mixture is stirred at room temperature over 12 hours. After reaction is complete, the reaction mixture is concentrated to dryness, and the residue is taken up ethyl acetate and washed with saturated sodium carbonate solution. The organic phase is subsequently separated off, dried over sodium sulfate and concentrated after filtration. The resulting crude product is purified by flash chromatography on silica gel 60 (mobile phase: cyclohexane/ethyl acetate 9:1). 5.26 g (19.4 mmol, 98% of theory) of the title compound are obtained.

$^1$H-NMR (300 MHz, DMSO-d$_6$, δ/ppm): 4.83 (s, 2H), 7.58 (d, 2H), 7.78 (d, 2H), 7.91 (d, 2H), 7.82 (d, 2H).

MS (E1): 270 (M$^+$).

Example 12A

[5-Fluoro-2-(4'-trifluoromethylbiphenyl-4-yl-methoxy)phenyl]methanol

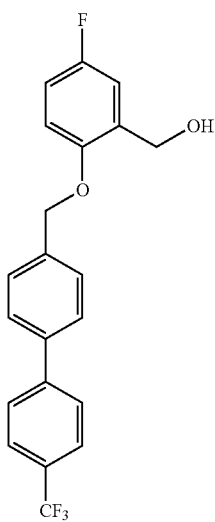

A solution of 4.59 g (36.9 mmol) of 5-fluoro-2-hydroxy-benzyl alcohol [CAS 2357-33-7] in 200 ml of dry acetonitrile is mixed with 10.0 g (36.9 mmol) of 4-chloromethyl-4'-trifluoromethylbiphenyl and 6.13 g (44.3 mmol) of anhydrous potassium carbonate and heated under reflux for 12 hours. The mixture is then concentrated to dryness. The residue is taken up in ethyl acetate, washed with water and saturated sodium chloride solution and dried over sodium sulfate. After concentration, the resulting crude product is purified by flash chromatography on silica gel 60 (mobile phase: cyclohexane/ethyl acetate 5:1). 11.8 g (32.9 mmol, 89% of theory) of the title compound are obtained.

$^1$H-NMR (300 MHz, DMSO d$_6$, δ/ppm): 4.57 (d, 2H), 5.18 (m$_c$, 3H), 6.97-7.08 (m, 2H), 7.18 (dd, 1H), 7.58 (d, 2H), 7.75-7.83 (m, 4H), 7.91 (d, 2H).

MS (DCI): 394 (M+NH$_4^+$).

HPLC (method 2): R$_t$ 5.3 min.

Example 13A

Triphenyl[5-fluoro-2-(4'-trifluoromethylbiphenyl-4-ylmethoxy)benzyl]phosphonium bromide

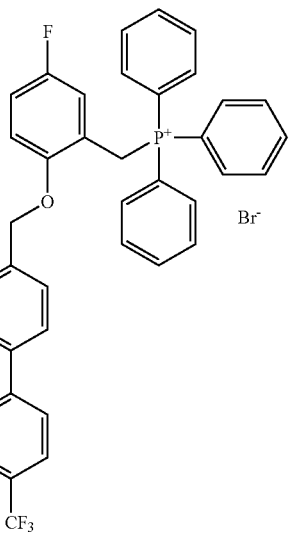

A solution of 3.00 g (7.97 mmol) of [2-(4'-trifluoromethylbiphenyl-4-ylmethoxy)phenyl]methanol in 20 ml of acetonitrile is mixed with 2.60 g (7.57 mmol) of triphenylphosphine hydrobromide and heated under reflux for 20 hours. The reaction solution is then concentrated to dryness, and the resulting oil is taken up and triturated in petroleum ether. The product crystallizes as a white solid during this. 2.31 g (3.29 mmol, 41% of theory) of the title compound are obtained.

$^1$H-NMR (300 MHz, DMSO-d$_6$, δ/ppm): 472 (s, 2H), 5.05-4.98 (d, 2H), 6.92-6.86 (m, 1H), 7.00-6.96 (m, 1H), 7.20-7.12 (m, 1H), 7.35-7.30 (m, 2H), 7.75-7.57 (m, 14H), 7.95-7.82 (m, 7H).

MS (ESI): 621 (M–Br)$^+$.

Example 14A 3,5-Difluoro-4-triisopropylsilanyloxybenzaldehyde

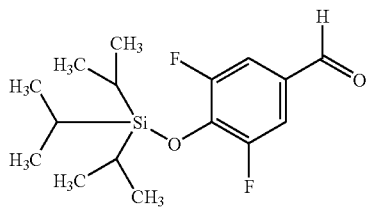

30.0 g (190 mmol) of 3,5-difluoro-4-hydroxybenzaldehyde [CAS 118276-06-5] are dissolved under argon in 600 ml of dichloromethane and, at 0° C., 44.7 g (417 mmol) of 2,6-lutidine are added. Then 87.2 g (284 mmol) of triisopropylsilyl trifluoromethanesulfonate are added dropwise, and the mixture is stirred at RT for 12 h. The solvent is distilled out in vacuo, and the residue is mixed with ammonium chloride solution and stirred for 5 min, and the organic phase is separated off. A further extraction with dichloromethane is carried out, and the organic phases are combined, washed with saturated sodium chloride solution, dried over magnesium sulfate, filtered and washed with dichloromethane, and the solvent is distilled off in vacuo. Chromatography on silica gel 60 (mobile phase: cyclohexane) results in 34.9 g (111 mmol, 58% of theory) of the title compound.

$^1$H-NMR (400 MHz, DMSO-d$_6$, δ/ppm): 1.06 (d, 18H), 1.29 (sept, 3H), 7.68-7.74 (m, 2H), 9.86 (s, 1H).

HPLC (method 3): R$_t$ 3.2 min.

MS (EI): 314 (M$^+$).

Example 15A 1,3-Difluoro-5-hydroxymethyl-2-triisopropylsilanyloxybenzene

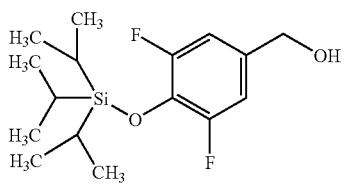

35.0 g (111 mmol) of 3,5-difluoro-4-triisopropylsilanyloxybenzaldehyde are introduced into 150 ml of water and 40 ml of methanol, cooled to 0° C. and, after addition of 8.42 g (222 mmol) of sodium borohydride in portions, stirred at RT overnight. The mixture is cautiously acidified with 1 N hydrochloric acid and extracted with ethyl acetate, and the combined organic phases are washed with saturated sodium chloride solution and dried over magnesium sulfate, and the solvent is distilled out in vacuo. Chromatography on silica gel 60 (mobile phase: cyclohexane/ethyl acetate 4:1) results in 29.5 g (93.2 mmol, 84% of theory) of the title compound.

$^1$H-NMR (400 MHz, DMSO-d$_6$, δ/ppm): 1.05 (d, 18H), 1.25 (sept, 3H); 4.42 (d, 2H), 5.31 (t, 1H), 6.97-7.04 (m, 2H).

HPLC (method 1): R$_t$ 5.9 min.

MS (DCI): 333 (M+NH$_4$$^+$).

Example 16A

5-Bromomethyl-1,3-difluoro-2-triisopropylsilanyloxybenzene

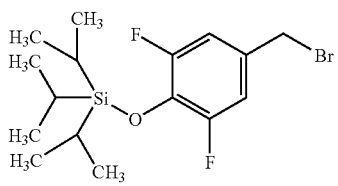

7.40 g (23.4 mmol) of 1,3-difluoro-5-hydroxymethyl-2-triisopropylsilanyloxybenzene are dissolved in 90 ml of dry dichloromethane by stirring at 0° C. under argon. 10.1 g (30.4 mmol) of tetrabromomethane and 7.97 g (30.4 mmol) of triphenylphosphine are successively added to this solution, and the mixture is then stirred under reflux under argon for 12 h. The reaction mixture is washed with water, the organic phase is separated off, dried over magnesium sulfate and filtered, and the solvent is distilled out in vacuo. The oily residue is taken up in diethyl ether and stirred at RT, then filtered, and the filtrate is concentrated. Chromatography of the residue on silica gel 60 (mobile phase: cyclohexane/ethyl acetate 9:1) results in 7.42 g (15.6 mmol, 84% of theory) of the title compound.

$^1$H-NMR (300 MHz, DMSO-d$_6$, δ/ppm): 1.05 (d, 18H), 1.25 (sept, 3H), 4.61 (s, 2H), 7.19-7.28 (m, 2H).

HPLC (method 1): R$_t$ 7.4 min.

Example 17A

1-Allyl 7-ethyl 2-allyloxycarbonyl-2-(3,5-difluoro-4-triisopropylsilanyloxybenzyl)heptanedioate

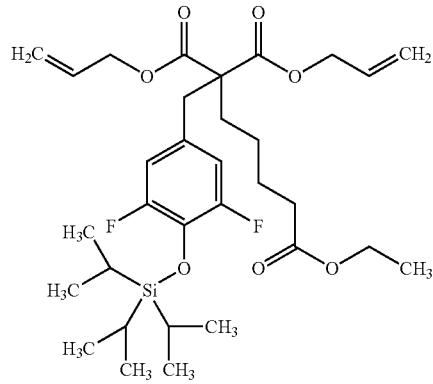

3.17 g (10.14 mmol) of 1-allyl 7-ethyl 2-allyloxycarbonylheptanedioate (Example 48A) are dissolved in 30 ml of DMF and, at 0° C., 0.45 g (11.15 mmol) of 60% sodium hydride is added in portions, and the mixture is stirred at RT for 30 minutes. After renewed cooling to 0° C., a solution of 5 g (13.18 mmol) of 3,5-difluoro-4-triisopropylsilanyloxybenzyl bromide in 20 ml of DMF is added dropwise, and the mixture is stirred while warming to room temperature overnight. The mixture is poured into ice, weakly acidified with hydrochloric acid and extracted with ethyl acetate. The combined organic phases are dried over sodium sulfate and concentrated. The resulting crude product is purified by chromatography on silica gel (mobile phase: cyclohexane, then cyclohexane/ethyl acetate 10:1). 4.57 g (73% of theory) of the title compound are obtained.

$^1$H-NMR (400 MHz, CDCl$_3$, δ/ppm): 1.1 (d, 18H), 1.25 (m, 8H), 1.65 (q, 2H), 1.8 (m, 2H), 2.3 (t, 2H), 3.1 (s, 2H), 4.15 (t, 2H), 4.6 (d, 4H), 5.25 (d, 2H), 5.35 (d, 2H), 5.85 (m, 2H), 6.6 (d, 2H).

LC-MS (method 1): R$_t$ 3.75 min; m/z 611 (M+H)$^+$.

Example 18A 2-(3,5-Difluoro-4-triisopropylsilanyloxybenzyl)heptanedioic acid 7-ethyl ester

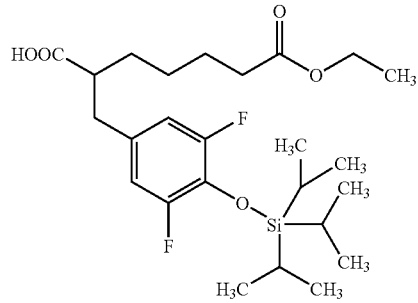

4.2 g (6.88 mmol) of 1-allyl 7-ethyl 2-allyloxycarbonyl-2-(3,5-difluoro-4-triisopropylsilanyloxy-benzyl)heptanedioate, 39 mg (0.17 mmol) of palladium(II)acetate and 135 mg (0.52 mmol) of triphenylphosphine are stirred in 30 ml of dioxane under argon. A solution of 2.3 g (22.69 mmol) of triethylamine and 0.79 g (17.19 mmol) of formic acid in 20 ml of dioxane is then added dropwise, and the mixture is heated at 100° C. overnight. The cooled mixture is concentrated and the crude product is chromatographed on silica gel (mobile phase: cyclohexane/ethyl acetate 10:1, 3:1). 2.07 g (52% of theory) of the title compound are obtained.

$^1$H-NMR (300 MHz, CDCl$_3$, δ/ppm): 1.1 (d, 18H), 1.25 (t, 3H), 1.3-1.7 (m, 8H), 2.3 (t, 2H), 2.65 (m, 2H), 2.9 (m, 1H), 4.15 (q, 2H), 6.7 (d, 2H).

LC-MS (method 3): R$_t$ 3.42 min; m/z 485 (M–H)$^-$.

Example 19A

Ethyl 6-(3,5-difluoro-4-triisopropylsilanyloxybenzyl)-7-hydroxyheptanoate

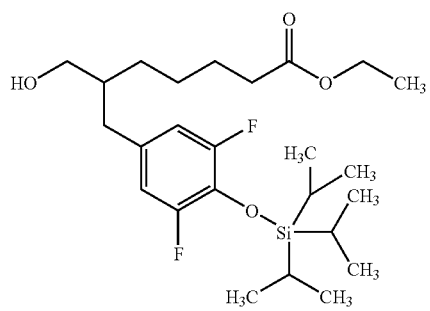

1.6 g (3.29 mmol) of 2-(3,5-difluoro-4-triisopropylsilanyloxybenzyl)heptanedioic acid 7-ethyl ester are dissolved in 30 ml of THF and cooled to –10° C. under argon. Then, 4.27 ml (4.27 mmol) of a 1 M borane-THF complex solution are added dropwise, and the mixture is stirred at 0° C. until reaction is complete. The mixture is hydrolyzed with water and extracted with ethyl acetate, and the combined organic phases are concentrated. The resulting crude product is purified by chromatography on silica gel (mobile phase: cyclohexane/ethyl acetate 7:1, 3:1). 1.18 g (76% of theory) of the title compound are obtained.

$^1$H-NMR (300 MHz, CDCl$_3$, δ/ppm): 1.1 (d, 18H), 1.25 (t, 3H), 1.3-1.8 (m, 10H), 2.3 (t, 2H), 2.55 (ddd, 2H), 3.5 (d, 2H), 4.15 (q, 2H), 6.7 (d, 2H).

LC-MS (method 3): R$_t$ 3.53 min; m/z 473 (M+H)$^+$.

Example 20A

Ethyl 7-(3,5-difluoro-4-triisopropylsilanyloxyphenyl)-6-formylheptanoate

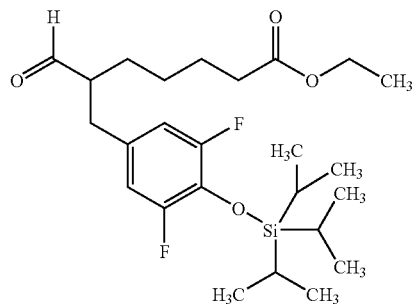

1.19 g (2.52 mmol) of ethyl 6-(3,5-difluoro-4-triisopropylsilanyloxybenzyl)-7-hydroxyheptanoate are stirred with 5 g of 4 Å molecular sieves and 442 mg (3.78 mmol) of N-methylmorpholine N-oxide in 50 ml of dichloromethane at room temperature for 10 minutes. 44 mg (0.13 mmol) of tetrapropylammonium perruthenate are added, and the mixture is stirred at room temperature until reaction is complete. The mixture is filtered and the filtrate is washed with water and saturated sodium chloride solution. The organic phase is dried over sodium sulfate and concentrated. The resulting crude product is purified by chromatography on silica gel (mobile phase: cyclohexane/ethyl acetate 3:1). 1.0 g (84% of theory) of the title compound is obtained.

$^1$H-NMR (400 MHz, CDCl$_3$, δ/ppm): 1.1 (d, 18H), 1.25 (t, 3H), 1.3-1.8 (m, 9H), 2.3 (t, 2H), 2.6 (dd, 2H), 2.9 (dd, 1H), 4.1 (q, 2H), 6.65 (d, 2H), 9.65 (d, 1H).

LC-MS (method 3): R$_t$ 3.63 min; m/z 488 (M+NH$_4$)$^+$.

Example 21A

Ethyl 6-(3,5-difluoro-4-triisopropylsilanyloxybenzyl)-8-[5-fluoro-2-(4'-trifluoromethylbiphenyl-4-ylmethoxy)phenyl]oct-7-enoate

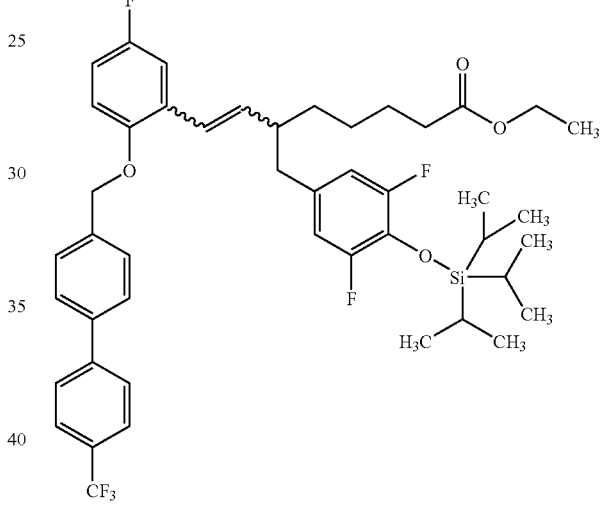

0.7 ml (1.12 mmol) of a 1.6 M solution of n-butyllithium in hexane is added dropwise to a suspension of 784 mg (1.06 mmol) of [5-fluoro-2-(4'-trifluoromethylbiphenyl-4-ylmethoxy)-benzyl]triphenylphosphonium bromide in 10 ml of THF at 0° C. and then stirred for 45 min. Subsequently, a solution of 500 mg (1.06 mmol) of ethyl 7-(3,5-difluoro-4-triisopropylsilanyloxy-phenyl)-6-formylheptanoate in 10 ml of THF is added dropwise at 0° C. and then stirred at this temperature for 2 h. The mixture is mixed with saturated ammonium chloride solution and extracted with ethyl acetate. The combined organic phases are dried over sodium sulfate and concentrated. The resulting crude product is purified by chromatography on silica gel (mobile phase: cyclohexane/ethyl acetate 7:1). 813 mg (84% of theory) of the title compound are obtained as an E/Z mixture (2:1).

$^1$H-NMR (400 MHz, CDCl$_3$, δ/ppm): 1.1 (m, 18H), 1.2 (m, 3H), 1.3-1.7 (m, 9H), 2.35 (m, 2H), 2.4-2.85 (m, 3H), 4.1 (q, 2H), 5.0 (s, 2H (Z)), 5.05 (s, 2H (E)), 5.45 (t, 1H (Z)), 5.95 (dd, 1H (E)), 6.5-6.7 (m, 3H), 6.85 (m, 2H), 7.05 (dd, 1H (E)), 7.5 (m, 2H), 7.65 (t, 2H), 7.7 (d, 4H).

HPLC (method 4): R$_t$ 18.4 and 18.9 min.

MS (ESI): m/z 830 (M+NH$_4$)$^+$.

Example 22A

Ethyl 6-(3,5-difluoro-4-triisopropylsilanyloxybenzyl)-8-[5-fluoro-2-(2-chlorobenzyloxy)phenyl]-oct-7-enoate

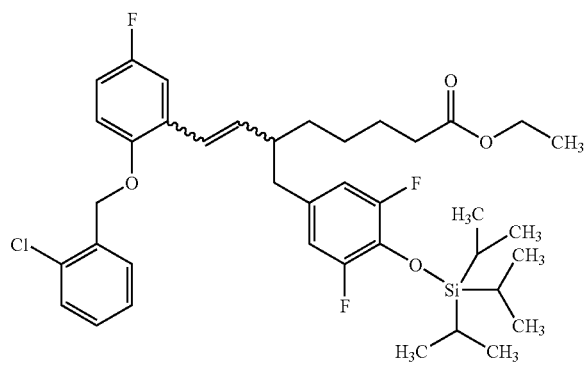

Reaction in analogy to Example 21A of [2-(2-chlorobenzyloxy)-5-fluorobenzyl]tri-phenylphosphonium bromide and ethyl 7-(3,5-difluoro-4-triisopropylsilanyloxyphenyl)-6-formylheptanoate results in the title compound with 70% of theory as E/Z mixture (2:1).

$^{1}$H-NMR (400 MHz, CDCl$_3$, δ/ppm): 1.1 (m, 18H), 1.25 (m, 3H), 1.3-1.7 (m, 9H), 2.15-2.3 (m, 2H), 2.4-2.85 (m, 3H), 4.1 (dq, 2H), 5.05 (s, 2H (Z)), 5.15 (s, 2H (E)), 5.45 (t, 1H (Z)), 5.95 (dd, 1H (E)), 6.5-6.7 (m, 3H), 6.8 (m, 2H), 7.05 (dd, 1H (E)), 7.3 (m, 2H), 7.4 (m, 1H), 7.45 (m, 1H).

LC-MS (method 2): R$_t$ 4.15 min; m/z 720 (M+NH$_4$)$^+$.

Example 23A

Ethyl E-6-(3,5-difluoro-4-triisopropylsilanyloxybenzyl)-8-[{5-fluoro-2-[2-(4-trifluoromethyl-phenyl)ethoxy]phenyl}oct-7-enoate

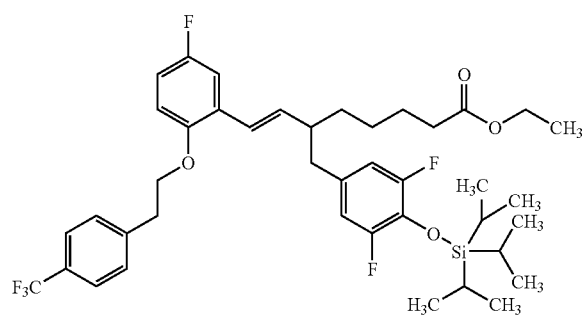

Reaction in analogy to Example 21A of {5-fluoro-2-[2-(4-trifluoromethylphenyl)ethoxy]benzyl}-triphenylphosphonium bromide and ethyl 7-(3,5-difluoro-4-triisopropylsilanyloxyphenyl)-6-formylheptanoate results in the title compound with 70% of theory.

$^{1}$H-NMR (300 MHz, CDCl$_3$, δ/ppm): 1.1 (m, 18H), 1.2 (m, 3H), 1.3-1.7 (m, 9H), 2.25 (m, 3H), 2.4-2.6 (m, 2H), 3.15 (m, 2H), 4.15 (m, 4H), 5.85 (dd, 1H), 6.35 (d, 1H), 6.65 (m, 2H), 6.7-6.9 (m, 2H), 7.0 (dd, 1H), 7.4 (m, 2H), 7.55 (m, 2H).

LC-MS (method 1): R$_t$ 4.34 min; m/z 593 (M−C$_9$H$_{21}$Si)$^-$.

Example 24A

Ethyl 6-(3,5-difluoro-4-hydroxybenzyl)-8-[5-fluoro-2-(4'-trifluoromethylbiphenyl-4-ylmethoxy)-phenyl]oct-7-enoate

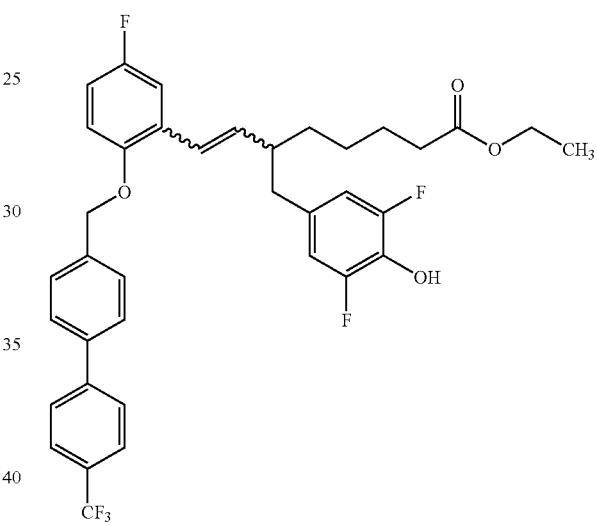

720 mg (0.89 mmol) of ethyl 6-(3,5-difluoro-4-triisopropylsilanyloxybenzyl)-8-[5-fluoro-2-(4'-trifluoromethylbiphenyl-4-ylmethoxy)phenyl]oct-7-enoate are introduced into 15 ml of THF at 0° C. under argon, 1.77 ml (1.77 mmol) of a 1 M solution of tetra-n-butylammonium fluoride in THF are added, and the mixture is stirred at room temperature until reaction is complete. All the volatile components are removed in vacuo. The resulting crude product is purified by chromatography on silica gel (mobile phase: cyclohexane/ethyl acetate 7:1). 400 mg (68% of theory) of the title compound are obtained as an E/Z mixture (2:1).

$^{1}$H-NMR (400 MHz, CDCl$_3$, δ/ppm): 1.25 (dt, 3H), 1.3-1.7 (m, 6H), 2.25 (m, 2H), 2.4-2.8 (m, 3H), 4.1 (dq, 2H), 5.0 (s, 2H (Z)), 5.05 (s, 2H (E)), 5.45 (t, 1H (Z)), 5.95 (dd, 1H (E)), 6.55-6.9 (m, 5H), 7.1 (dd, 1H (E)), 7.45 (m, 2H), 7.65 (t, 2H), 7.7 (d, 4H).

LC-MS (method 1): R$_t$ 3.42 min; m/z 674 (M+NH$_4$)$^+$.

The following compounds are obtained in an analogous manner:

| Example No. | Structure | Analytical data |
| --- | --- | --- |
| 25A | 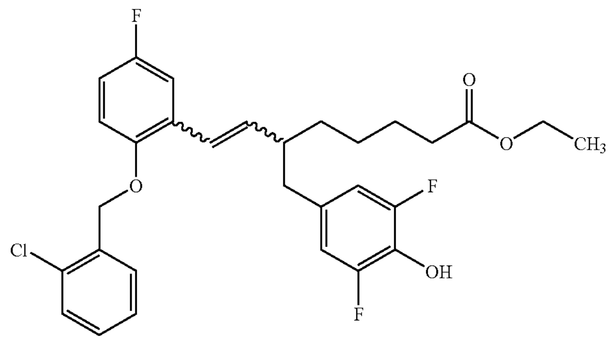 | $^1$H-NMR (300 MHz, CDCl$_3$, δ/ppm): 1.25 (m, 3H), 1.3-1.7 (m, 6H), 2.25 (m, 2H), 2.3-2.8 (m, 3H), 4.1 (q, 2H), 5.05 (s, 2H (Z)), 5.1 (s, 2H (E)), 5.45 (t, 1H (Z)), 5.95 (dd, 1H (E)), 6.55 (m, 2H), 6.7 (m, 2H), 6.85 (m, 2H), 7.05 (dd, 1H (E)), 7.3 (m, 2H), 7.45 (m, 2H). LC-MS (method 2): R$_t$ 3.12 min; m/z 564 (M + NH$_4$)$^+$. |
| 26A | 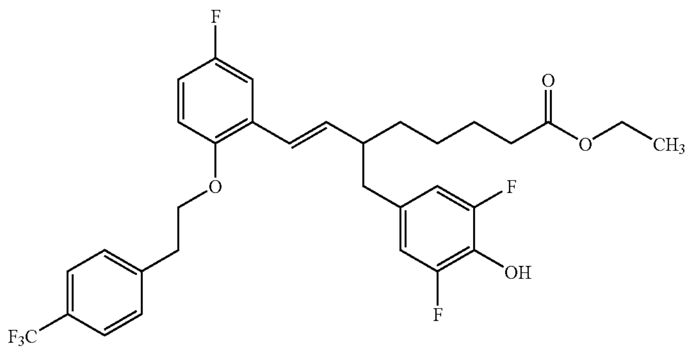 | $^1$H-NMR (300 MHz, CDCl$_3$, δ/ppm): 1.2 (m, 3H), 1.3-1.7 (m, 6H), 2.3 (m, 3H), 2.6 (m, 2H), 3.15 (m, 2H), 4.1 (m, 4H), 5.85 (dd, 1H), 6.35 (d, 1H), 6.6 (m, 2H), 6.7-6.9 (m, 2H), 7.05 (dd, 1H), 7.4 (m, 2H), 7.55 (m, 2H). LC-MS (method 2): R$_t$ = 3.11 min; m/z 595 (M + H)$^+$. |

Example 27A

Diallyl 2-[2-(4-methoxycarbonylphenyl)ethyl]malonate

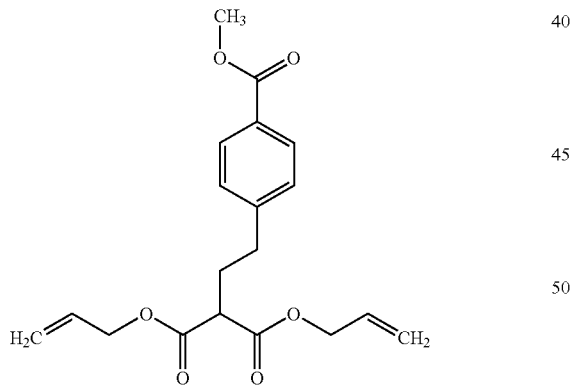

814 mg (20.36 mmol) of sodium hydride are added in portions (caution: evolution of hydrogen) to a solution of 5 g (27.15 mmol) of diallyl malonate in 25 ml of dioxane at 0° C. The mixture is warmed to room temperature and then stirred at 40° C. for 30 minutes. Subsequently, at 40° C., 3.3 g (13.57 mol) of methyl 4-(2-bromoethyl)benzoate, dissolved in 25 ml of dioxane, are slowly added dropwise, and the reaction solution is stirred at 110° C. overnight. After cooling to room temperature, the reaction mixture is added to 120 ml of saturated ammonium chloride solution. The mixture is extracted three times with ethyl acetate, and the combined organic phases are washed with saturated sodium chloride solution and dried over sodium sulfate. After filtration, the solvent is concentrated to dryness in vacuo. Excess diallyl malonate is then removed by high vacuum distillation (boiling point: 57° C.; 0.074 mbar). The distillation residue is purified by flash chromatography on silica gel (mobile phase: cyclohexane/ethyl acetate 9:1→1:1). 2.8 g (26% of theory) of a colorless solid are obtained.

$^1$H-NMR (400 MHz DMSO-d$_6$, δ/ppm): 7.90 (2H, d), 7.37 (2H, d), 5.98-5.81 (2H, m), 5.38-5.18 (4H, m), 4.68-4.54 (4H, m), 3.85 (3H, s), 3.59 (1H, t), 2.69 (2H, t), 2.17-2.04 (2H, m).
MS (DCI): 364 (M+NH$_4^+$).

Example 28A

Diallyl 2-(3,5-difluoro-4-triisopropylsilanyloxybenzyl)-2-[2-(4-methoxycarbonylphenyl)ethyl]-malonate

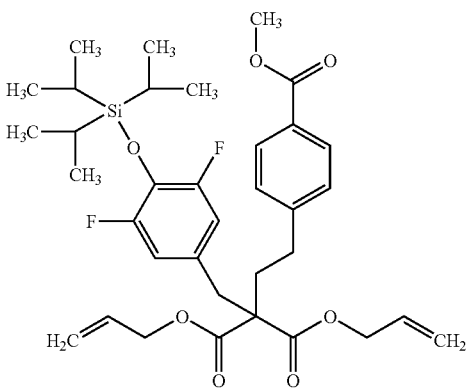

5.9 g (17.05 mmol) of diallyl 2-[2-(4-methoxycarbonylphenyl)ethyl]malonate are dissolved in 125 ml of dioxane and, at 0° C., 818 mg (20.46 mmol) of 60% sodium hydride are added in portions, and the mixture is stirred at room temperature for 30 min. After renewed cooling to 0° C., a solution of 9.7 g (25.57 mmol) of 3,54-difluoro-4-triisopropylsilanyloxybenzyl bromide in 125 ml of dioxane is added dropwise, and the mixture is stirred while warming to room temperature for 2 h. The reaction solution is then added to 250 ml of saturated ammonium chloride solution and extracted with ethyl acetate. The combined organic phases are dried over sodium sulfate and concentrated. The resulting crude product is purified by preparative HPLC. 7.2 g (65% of theory) of the title compound are obtained.

$^1$H-NMR (300 MHz, DMSO-$d_6$, δ/ppm): 7.88 (2H, d), 7.30 (2H, d), 6.91 (2H, d), 5.98-5.81 (2H, m), 5.39-5.20 (4H, m), 4.63 (4H, d), 3.83 (3H, s), 3.27 (2H, s), 2.71-2.58 (2H, m), 1.98-1.83 (2H, m), 1.30-1.12 (3H, m), 1.02 (18H, d).

MS (EI): 645 (M+H$^+$), 667 (M+Na$^+$).

Example 29A

Methyl 4-[3-carboxy-4-(3,5-difluoro-4-triisopropylsilanyloxyphenyl)butyl]benzoate

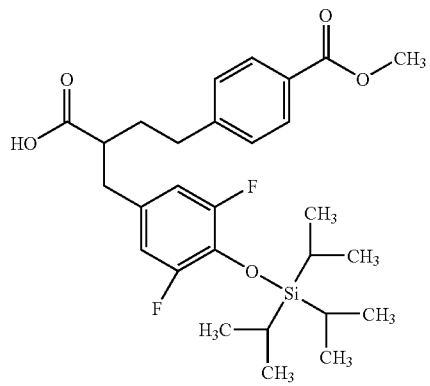

9.2 g (14.27 mmol) of diallyl 2-(3,5-difluoro-4-triisopropylsilanyloxybenzyl)-2-[2-(4-methoxycarbonylphenyl)ethyl]malonate, 64 mg (0.29 mmol) of palladium(II) acetate and 262 mg (1 mmol) of triphenylphosphine are stirred in 300 ml of dioxane under argon. Then a solution of 4.76 g (47.08 mmol) of triethylamine and 1.64 g (35.67 mmol) of formic acid in 200 ml of dioxane is added dropwise, and the mixture is heated at 100° C. for 2 h. The cooled mixture is concentrated and the crude product is chromatographed on silica gel (mobile phase: cyclohexane/ethyl acetate 10:1→4:1). 3.69 g (49% of theory) of the title compound are obtained.

$^1$H-NMR (300 MHz, CDCl$_3$, δ/ppm): 12.50-10.00 (1H, broad), 7.95 (2H, d), 7.20 (2H, d), 6.65 (2H, d), 3.91 (3H, s), 2.99-2.84 (1H, m), 2.83-2.49 (4H, m), 2.08-1.90 (1H, m), 1.89-1.71 (1H, m), 1.34-1.17 (3H, m), 1.09 (18H, m).

MS (EI): 519 (M-H$^-$).

Example 30A

Methyl 4-[3-(3,5-difluoro-4-triisopropylsilanyloxybenzyl)-4-hydroxybutyl]benzoate

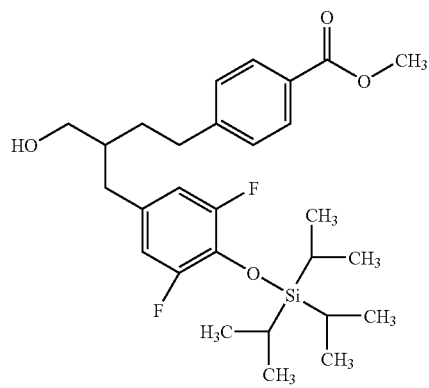

4.2 g (8.07 mmol) of methyl 4-[3-carboxy-4-(3,5-difluoro-4-triisopropylsilanyloxyphenyl)butyl]-benzoate are dissolved in 200 ml of THF and cooled to -10° C. under argon. Then 16.13 ml (16.13 mmol) of a 1 M borane-THF complex solution are added dropwise, and the mixture is stirred at 0° C. until reaction is complete. The mixture is hydrolyzed with saturated ammonium chloride solution and extracted with diethyl ether, and the combined organic phases are concentrated. The resulting crude product is purified by chromatography on silica gel (mobile phase: cyclohexane/ethyl acetate 20:1→10:1→4:1). 2.92 g (71% of theory) of the title compound are obtained.

$^1$H-NMR (400 MHz, DMSO-$d_6$, δ/ppm): 7.85 (2H, d), 7.28 (2H, d), 6.89 (2H, d), 4.54 (1H, t), 3.83 (3H, s), 2.75-2.54 (3H, m), 1.72-1.52 (3H, m), 1.50-1.37 (3H, m), 1.30-1.15 (3H, m), 1.04 (18H, d).

MS (DCI): 524 (M+NH$_4^+$).

Example 31A

Methyl 4-[3-(3,5-difluoro-4-triisopropylsilanyloxybenzyl)-4-oxobutyl]benzoate

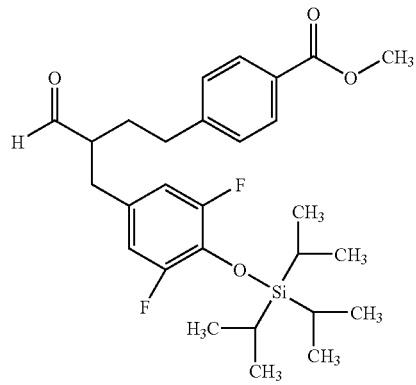

A solution of 2.9 g (5.72 μmmol) of methyl 4-[3-(3,5-difluoro-4-triisopropylsilanyloxybenzyl)-4-hydroxybutyl]benzoate in 50 ml of dichloromethane is mixed with 1.48 g (6.87 mmol) of pyridinium chlorochromate (PCC) and stirred at room temperature for 12 h. After conversion is complete, about 10 g of silica gel are added, and the solvent is removed to dryness in vacuo. The residue is purified by flash chromatography on silica gel (mobile phase: cyclohexane/ethyl acetate 10:1→4:1). 1.96 g (68% of theory) of a colorless solid are obtained.

$^1$H-NMR (300 MHz, DMSO-$d_6$, δ/ppm): 9.64 (1H, s), 7.86 (2H, d), 7.29 (2H, d), 6.98 (2H, d), 3.83 (3H, s), 3.32 (2H, d), 3.01-2.82 (1H, m), 2.76-2.54 (2H, m), 1.94-1.73 (1H, m), 1.72-1.56 (1H, m), 1.31-1.11 (3H, m), 1.04 (18H, d).

MS (DCI): 522 (M+NH$_4^+$).

Example 32A

Methyl E-4-[3-(3,5-difluoro-4-triisopropylsilanyloxybenzyl)-5-(2-hydroxyphenyl)pent-4-enyl]-benzoate

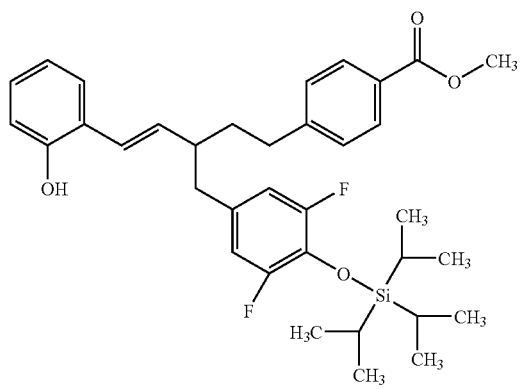

7.49 ml (11.98 mmol) of a 1.6 M solution of n-butyllithium in hexane are slowly added to a solution of 2.38 g (5.14 mmol) of (2-hydroxybenzyl)triphenylphosphonium bromide in 50 ml of THF at 0° C. Then, at this temperature, 2.16 g (4.28 mmol) of methyl 4-[3-(3,5-difluoro-4-triisopropylsilanyloxybenzyl)-4-oxobutyl]benzoate are slowly metered in. The reaction solution is stirred at 0° C. for 2 hours and then mixed with 100 ml of saturated ammonium chloride solution and extracted with diethyl ether. The combined organic phases are washed with saturated sodium chloride solution and dried over sodium sulfate. After filtration, the solvent is concentrated to dryness. The resulting crude product is purified by flash chromatography on silica gel (mobile phase: cyclohexane/ethyl acetate 10:1). 2.37 g (90% of theory) of a colorless solid are obtained.

$^1$H-NMR (400 MHz, DMSO-$d_6$, δ/ppm): 9.44 (1H, s), 7.85 (2H, d), 7.30 (2H, d), 7.01 (1H, t), 6.91 (2H, d), 6.79 (1H, d), 6.72 (1H, t), 6.45 (1H, d), 6.08-5.97 (1H, m), 3.84 (3H, s), 2.80-2.67 (2H, m), 2.66-2.54 (2H, m), 2.48-2.36 (1H, m), 1.80-1.67 (1H, m), 1.67-1.54 (1H, m), 1.29-1.11 (3H, m), 1.01 (18H, d).

MS (EI): 595 (M+H$^+$).

Example 33A

Methyl E-4-[5-[2-(4-tert-butylbenzyloxy)phenyl]-3-(3,5-difluoro-4-triisopropylsilanyloxybenzyl)-pent-4-enyl]benzoate

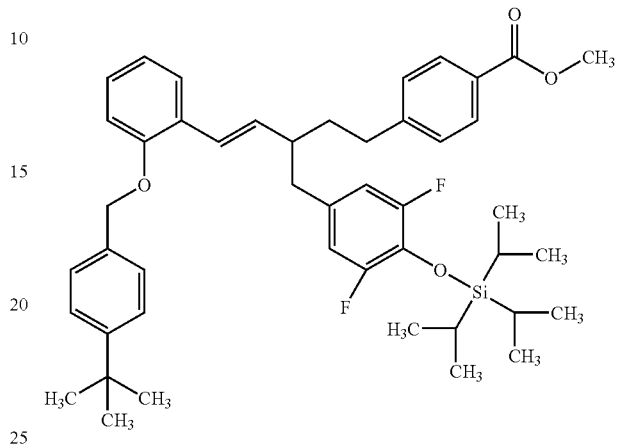

A solution of 1.3 g (2.19 mmol) of methyl E4-[3-(3,5-difluoro-4-triisopropylsilanyloxybenzyl)-5-(2-hydroxyphenyl)pent-4-enyl]benzoate in 20 ml of dry acetonitrile is mixed with 600 mg (2.62 mmol) of 4-tert-butylbenzyl bromide and 450 mg (3.28 mmol) of anhydrous potassium carbonate and heated under reflux for 12 hours. The mixture is then concentrated to dryness. The residue is taken up in ethyl acetate, washed with water and saturated sodium chloride solution, dried over sodium sulfate and concentrated. The resulting crude product is purified by preparative HPLC. 780 mg (48% of theory) of a colorless oil are obtained.

LC-MS (method 4): R$_t$ 4.23 min; m/z 759 (M+NH$_4^+$).

Example 34A

Methyl E4-[5-[2-(4-tert-butylbenzyloxy)phenyl]-3-(3,5-difluoro-4-hydroxybenzyl)pent-4-enyl]-benzoate

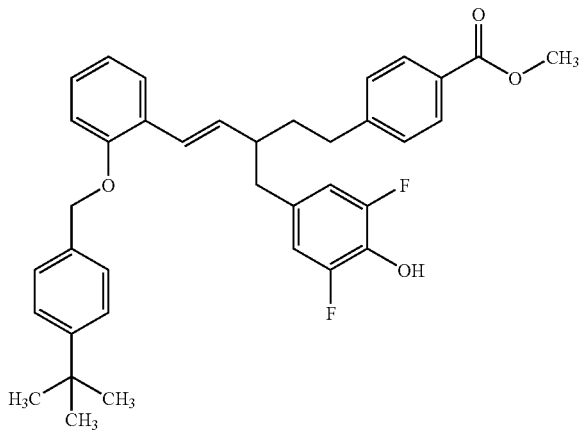

780 mg (1.05 mmol) of methyl E-4-[5-[2-(4-tert-butylbenzyloxy)phenyl]-3-(3,5-difluoro-4-triisopropylsilanyloxybenzyl)pent-4-enyl]benzoate are introduced into 20 ml of THF at room temperature under argon, 2.11 ml (2.11 mmol) of a 1 M solution of tetra-n-butylammonium fluoride in THF are added, and the mixture is stirred at room temperature until reaction is complete. All the volatile components are then removed in vacuo. The resulting crude product is purified by preparative HPLC. 229 mg (37% of theory) of the title compound are obtained.

$^1$H-NMR (400 MHz, DMSO-d$_6$, δ/ppm): 9.79 (1H, s), 7.83 (2H, d), 7.41 (1H, d), 7.39-7.24 (6H, m), 7.19 (1H, t), 7.06 (1H, d), 6.98-6.87 (1H, m), 6.81 (2H, d), 6.52 (1H, d), 6.14-6.02 (1H, m), 5.08 (2H, s), 3.82 (3H, s), 2.79-2.52 (4H, m), 2.47-2.35 (1H, m), 1.82-1.69 (1H, m), 1.68-1.54 (1H, m), 1.24 (9H, s).

MS (EI): 607 (M+Na$^+$).

Example 35A

Diallyl 2-[2-(4-cyanophenyl)ethyl]malonate

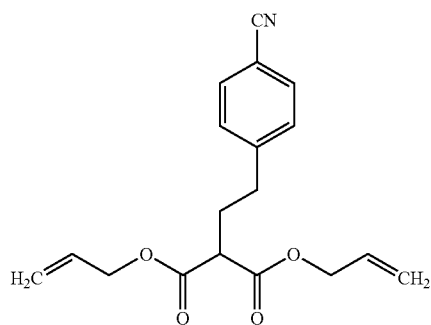

5.59 g (139.88 mmol) of 60% pure sodium hydride are added in portions (caution: evolution of hydrogen) to a solution of 34.35 g (186.51 mmol) of diallyl malonate in 300 ml of dioxane at 0° C. The mixture is warmed to room temperature and then stirred at 40° C. for 30 minutes. Subsequently, at 40° C., 19.59 g (93.25 mol) of 4-(2-bromoethyl)benzonitrile, dissolved in 200 ml of dioxane, are slowly added dropwise, and the reaction solution is then stirred at 110° C. overnight. After cooling to room temperature, the reaction mixture is added to 200 ml of saturated ammonium chloride solution. The mixture is then extracted three times with ethyl acetate, and the combined organic phases are washed with saturated sodium chloride solution and dried over sodium sulfate. After filtration, the solvent is concentrated to dryness in vacuo. Excess diallyl malonate is then removed by high vacuum distillation (boiling point: 57° C.; 0.074 mbar). The distillation residue is purified by flash chromatography on silica gel (mobile phase: cyclohexane/ethyl acetate 9:1→4:1). 14.18 g (24% of theory) of a colorless solid are obtained.

$^1$H-NMR (300 MHz, DMSO-d$_6$, δ/ppm): 7.77 (2H, d), 7.41 (2H, d), 5.98-5.80 (2H, m), 5.39-5.16 (4H, m), 4.70-4.51 (4H, m), 3.59 (1H, t), 2.70 (2H, t), 2.18-2.02 (2H, m).

MS (DCI): 331 (M+NH$_4^+$).

Example 36A

Diallyl 2-[2-(4-cyanophenyl)ethyl]-2-(3,5-difluoro-4-triisopropylsilanyloxybenzyl)malonate

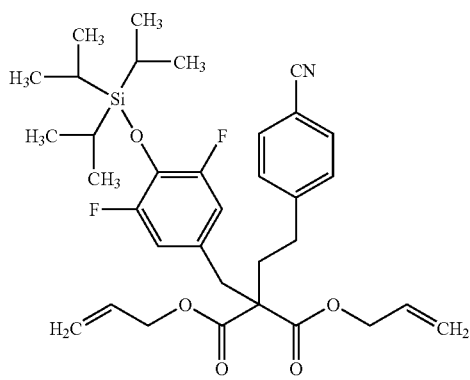

10 g (31.91 mmol) of diallyl 2-[2-(4-cyanophenyl)ethyl]malonate are dissolved in 250 ml of dioxane and, at 0° C., 1.4 g (35.1 mmol) of 60% sodium hydride are added in portions, and the mixture is stirred at room temperature for 30 min. After renewed cooling to 0° C., a solution of 14.53 g (38.30 mmol) of 3,5-difluoro-4-triisopropylsilanyloxybenzyl bromide in 250 ml of dioxane is added dropwise, and the mixture is stirred while warming to room temperature for 2 h. The reaction solution is then added to 500 ml of saturated ammonium chloride solution and extracted with ethyl acetate. The combined organic phases are dried over sodium sulfate and concentrated. The resulting crude product is purified by flash chromatography on silica gel (mobile phase: cyclohexane/ethyl acetate 10:1→4:1). 14.3 g (73% of theory) of the title compound are obtained.

$^1$H-NMR (400 MHz, DMSO-d$_6$, δ/ppm): 7.76 (2H, d), 7.37 (2H, d), 6.91 (2H, d), 5.98-5.82 (2H, m), 5.38-5.20 (4H, m), 4.68-4.56 (4H, m), 3.24 (2H, s), 2.74-2.61 (2H, m), 1.98-1.84 (2H, m), 1.29-1.13 (3H, m), 1.04 (18H, d).

MS (EI): 612 (M+H$^+$), 634 (M+Na$^+$).

Example 37A 4-(4-Cyanophenyl)-2-(3,5-difluoro-4-triisopropylsilanyloxybenzyl)butanoic acid

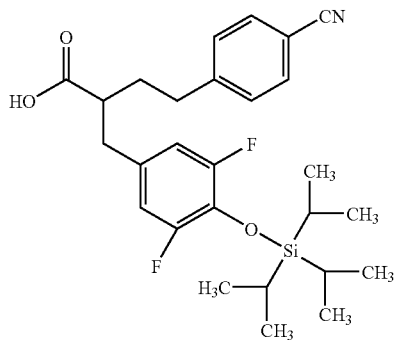

4720 mg (7.72 mmol) of diallyl 2-[2-(4-cyanophenyl)ethyl]-2-(3,5-difluoro-4-triisopropylsilanyloxybenzyl)malonate, 34.6 mg (0.15 mmol) of palladium(II) acetate and 141.6 mg (0.54 mmol) of triphenylphosphine are stirred in 180 ml of dioxane under argon. Then a solution of 2576 mg (25.60 mmol) of triethylamine and 887.7 mg (19.29 mmol) of formic acid in 90 ml of dioxane is added dropwise, and the mixture is heated at 100° C. for 2 h. The cooled mixture is concentrated and the crude product is chromatographed on silica gel (mobile phase: cyclohexane/ethyl acetate 9:1→2:1→1:1). 3682 mg (97.9% of theory) of the title compound are obtained $^1$H-NMR (400 MHz, DMSO-d$_6$, δ/ppm): 12.39-12.28 (1H, broad), 7.72 (2H, d), 7.35 (2H, d), 6.92 (2H, d), 2.84-2.59 (5H, m), 1.85-1.72 (1H, m), 1.71-1.60 (1H, m), 1.28-1.15 (3H, m), 1.04 (18H, d).

LC-MS (method 1): R$_t$ 3.48 min; m/z 478 (M−H$^−$).

Example 38A

4-[3-(3,5-Difluoro-4-triisopropylsilanyloxybenzyl)-4-hydroxybutyl]benzonitrile

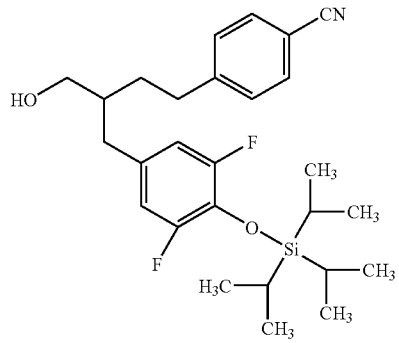

4879 mg (10 mmol) of 4-(4-cyanophenyl)-2-(3,5-difluoro-4-triisopropylsilanyloxybenzyl)butanoic acid are dissolved in 244 ml of THF and cooled to −10° C. under argon. Then 20.01 ml (20.01 mmol) of a 1 M borane-THF complex solution are added dropwise, and the mixture is stirred at 0° C. until reaction is complete. The mixture is hydrolyzed with saturated ammonium chloride solution and extracted with diethyl ether, and the combined organic phases are concentrated. The resulting crude product is purified by chromatography on silica gel (mobile phase: cyclohexane/ethyl acetate 9:1→4:1→2:1→1:1). 2705 mg (57% of theory) of the title compound are obtained.

$^1$H-NMR (400 MHz, DMSO-d$_6$, δ/ppm): 7.71 (2H, d), 7.34 (2H, d), 6.89 (2H, d), 4.54 (1H, t), 2.75-2.44 (6H, m), 1.72-1.51 (2H, m), 1.49-1.35 (1H, m), 1.30-1.15 (3H, m), 1.04 (18H, d).

LC-MS (method 2): R$_t$ 3.38 min; m/z 518 (M−H+HCO$_2$H)$^−$, 316 (M−SiC$_9$H$_{21}$).

Example 39A

4-[3-(3,5-Difluoro-4-triisopropylsilanyloxybenzyl)-4-oxobutyl]benzonitrile

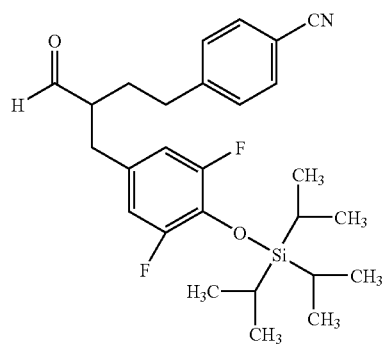

A solution of 750 mg (1.58 mmol) of 4-[3-(3,5-difluoro-4-triisopropylsilanyloxybenzyl)-4-hydroxybutyl]benzonitrile in 9 ml of dichloromethane is mixed with 409 mg (1.9 mmol) of pyridinium chlorochromate (PCC) and stirred at room temperature for 12 h. After conversion is complete, about 10 g of silica gel are added, and the solvent is removed in vacuo to dryness. The residue is purified by flash chromatography on silica gel (mobile phase: cyclohexane/ethyl acetate 10:1→5:1→2:1). 493 mg (64% of theory) of a colorless solid are obtained.

$^1$H-NMR (300 MHz, DMSO-d$_6$, δ/ppm): 9.63 (1H, s), 7.72 (2H, d), 7.35 (2H, d), 6.98 (2H, d), 2.99-2.84 (1H, m), 2.76-2.55 (4H, m), 1.91-1.78 (1H, m), 1.71-1.57 (1H, m), 1.29-1.15 (3H, m), 1.04 (18H, d).

LC-MS (method 2): R$_t$ 3.38 min; m/z 472 (M+H$^+$).

Example 40A

E4-[3-(3,5-Difluoro-4-triisopropylsilanyloxybenzyl)-5-(2-hydroxyphenyl)pent-4-enyl]benzonitrile

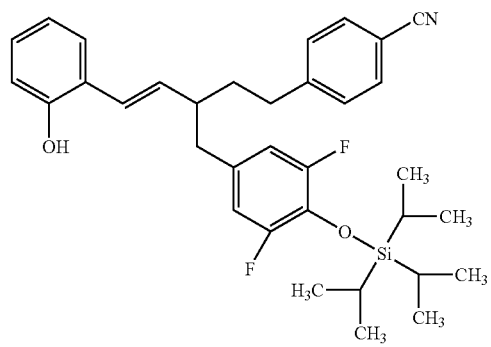

1.82 ml (2.91 mmol) of a 1.6 M solution of n-butyllithium in hexane are slowly added to a solution of 579 mg (1.25 mmol) of (2-hydroxybenzyl)triphenylphosphonium bromide in 11.5 ml of THF at 0° C. Then, at this temperature, 490 mg (1.04 mmol) of 4-[3-(3,5-difluoro-4-triisopropylsilanyloxybenzyl)-4-oxobutyl]benzonitrile are slowly metered in. The reaction solution is stirred at 0° C. for 2 h and then mixed with 100 ml of saturated ammonium chloride solution and extracted with diethyl ether. The combined organic phases are washed with saturated sodium chloride solution and dried over sodium sulfate. After filtration, the solvent is concentrated to dryness. The resulting crude product is purified by flash chromatography on silica gel (mobile phase: cyclohexane/ethyl acetate 10:1). 379.7 mg (54% of theory) of a colorless solid are obtained.

$^1$H-NMR (400 MHz, DMSO-$d_6$, δ/ppm): 9.42 (1H, s), 7.71 (2H, d), 7.35 (2H, d), 7.29 (2H, d), 7.05 (1H, m), 6.91 (2H, d), 6.79 (1H, d), 6.72 (1H, t), 6.44 (1H, d), 6.08-5.96 (1H, m), 2.79-2.65 (2H, m), 2.64-2.56 (2H, m), 2.47-2.36 (1H, m), 1.78-1.53 (2H, m), 1.29-1.10 (3H, m), 1.00 (18H, d).

MS (DCI): 579 (M+NH$_4^+$).

Example 41A

E-4-[5-[2-(4-tert-Butylbenzyloxy)phenyl]-3-(3,5-difluoro-4-triisopropylsilanyloxybenzyl)pent-4-enyl]benzonitrile

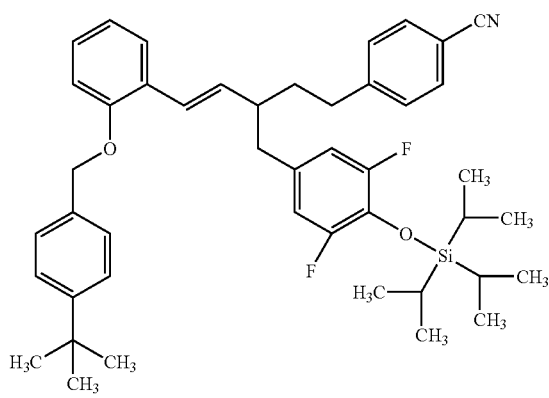

1.7 g (3 mmol) of 4-[(4E)-3-{3,5-difluoro-4-[(triisopropylsilyl)oxy]benzyl}-5-(2-hydroxyphenyl)pent-4-en-1-yl]benzonitrile in 35 ml of acetonitrile are mixed with 627 mg (4.5 mmol) of potassium carbonate and 1 g (4.5 mmol) of 4-tert-butylbenzyl bromide and stirred under reflux for 12 hours. The solvent is stripped off in vacuo, and the residue is taken up in ethyl acetate. The organic phase is washed once with sodium bicarbonate solution and once with sodium chloride solution, dried over sodium sulfate and concentrated. The crude product is purified by flash chromatography on silica gel (mobile phase: cyclohexane/ethyl acetate 10:1). 628 mg (85% purity, 0.76 mmol, 25% of theory) of the title compound are obtained.

HPLC (method 3): R$_t$=9.11 min

MS (ESIpos): m/z=708 (M+H)$^+$ $^1$H-NMR (400 MHz, DMSO-$d_6$, δ/ppm): 7.65 (d, 2H), 7.4-7.28 (m, 6H), 7.18 (t, 1H), 7.05 (d, 1H), 6.92-6.82 (m, 2H), 6.46 (d, 1H), 6.05 (dd, 1H), 5.1-5.0 (m, 2H), 2.77-2.5 (m, 4H), 2.46-2.31 (m, 1H), 1.8-1.55 (m, 2H), 1.25 (s, 9H), 1.22-1.1 (m, 3H), 0.98 (d, 18H).

Example 42A

E-5-{4-[5-[2-(4-tert-Butylbenzyloxy)phenyl]-3-(3,5-difluoro-4-triisopropylsilanyloxybenzyl)pent-4-enyl]phenyl}-1H-tetrazole

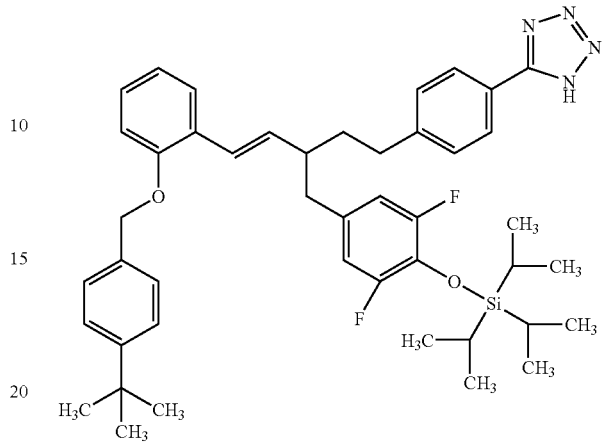

A solution of 625 mg (85% pure, 0.75 mmol) of E-4-[5-[2-(4-tert-butylbenzyloxy)phenyl]-3-(3,5-difluoro-4-triisopropylsilanyloxybenzyl)pent-4-enyl]benzonitrile in 12 ml of toluene is mixed with 1.76 ml (13.24 mmol) of trimethylsilyl azide and 329.6 mg (1.3 mmol) of di-n-butyltin oxide and stirred at 80° C. for 12 h. After conversion is complete, the mixture is extracted with sodium bicarbonate solution. The aqueous phase is back-extracted twice with ethyl acetate. The combined organic phases are washed with sodium chloride solution, dried over sodium sulfate and concentrated. The resulting residue is purified by flash chromatography on silica gel (mobile phase: cyclohexane/ethyl acetate 1:2→ethyl acetate). 447.3 mg (0.51 mmol, 86% purity, 58% of theory) of the title compound are obtained.

HPLC (method 3): R$_t$=7.97 min

MS (ESIpos): m/z=751 (M+H)$^+$ $^1$H-NMR (400 MHz, DMSO-$d_6$, δ/ppm): 7.92 (d, 2H), 7.42-7.26 (m, 7H), 7.18 (t, 1H), 7.05 (d, 1H), 6.93-6.84 (m, 3H), 6.5 (d, 1H), 6.08 (dd, 1H), 5.05 (s, 2H), 2.8-2.55 (m, 4H), 2.55-2.4 (m, 1H), 1.84-1.6 (m, 2H), 1.27-1.1 (m, 12H), 1.0 (d, 18H).

Example 43A

4-{[2-Chloromethyl)-4-fluorophenoxy]methyl}-4'-(trifluoromethyl)-1,1'-biphenyl

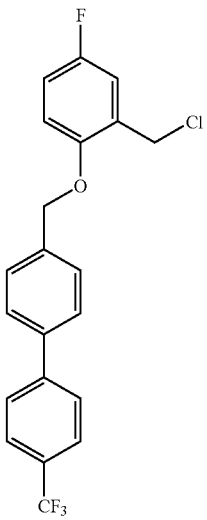

205 g (0.54 mol) of (5-fluoro-2-{[4'-trifluoromethyl-1,1'-biphenyl-4-yl]methoxy}phenyl]methanol are introduced into 1322 ml of dichloromethane at room temperature under argon, and a few drops of dimethylformamide are added. Then 122.5 ml (1.68 mol) of thionyl chloride are slowly added dropwise and the mixture is stirred at room temperature until reaction is complete. All the volatile components are removed in vacuo. The resulting residue is taken up in ethyl acetate and water while cooling. The organic phase is washed with saturated sodium carbonate solution and water and dried over sodium sulfate, and the solvent is removed in vacuo. 211 g (93% of theory) of the title compound are obtained.

$^1$H-NMR (300 MHz, CDCl$_3$, δ/ppm): 4.70 (2H, s), 5.20 (2H, s), 6.90 (2H, m), 7.10 (1H, m), 7.50 (2H, d), 7.60 (2H, d), 7.70 (4H, m).

Example 44A (5-Fluoro-2-{[4'-(trifluoromethyl)-1,1'-biphenyl-4-yl]methoxy}phenyl)acetonitrile

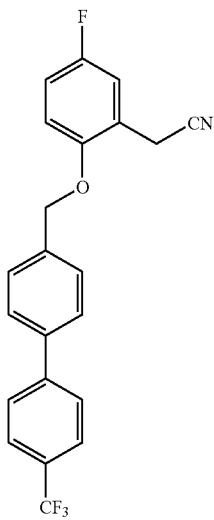

211 g (0.51 mol) of 4-{[2-chloromethyl)-4-fluorophenoxy]methyl}-4'-(trifluoromethyl)-1,1'-biphenyl are dissolved in 1.78 liters of dimethylformamide/water (5:1 v/v). Then, at room temperature, 149.1 g (3.04 mol) of sodium cyanide and a catalytic amount of potassium iodide are metered in. The reaction solution is stirred at 120° C. overnight. After reaction is complete (TLC check with cyclohexane/ethyl acetate 2:1), the reaction solution is cooled to room temperature and concentrated to about 60% of the solvent volume in vacuo. After addition of 5 liters of water, the reaction solution is extracted three times with 3 liters of ethyl acetate each time. The combined organic phases are dried over sodium sulfate, filtered and concentrated in vacuo. The resulting residue is chromatographed twice on 10 kg of silica gel (mobile phase: toluene). 145.7 g (69% of theory) of the title compound are obtained.

$^1$H-NMR (300 MHz, CDCl$_3$, δ/ppm): 3.70 (2H, s), 5.10 (2H, s), 6.90 (1H, m), 7.00 (1H, m), 7.15 (1H, m), 7.50 (2H, d), 7.60 (2H, d), 7.70 (4H, s).

Example 45A 2-(5-Fluoro-2-{[4'-(trifluoromethyl)-1,1'-biphenyl-4-yl]methoxy}phenyl)ethylamine

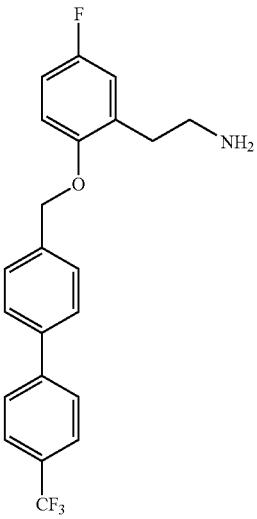

140.97 g (0.366 mol) of (5-fluoro-2-{[4'-(trifluoromethyl)-1,1'-biphenyl-4-yl]methoxy}phenyl)-acetonitrile are dissolved in 701 ml of anhydrous THF under argon and, after cooling to 0° C., 361.6 ml (0.362 mol) of a 1 M solution of lithium aluminum hydride in THF are added. Then 73.2 g (0.55 mol) of aluminum trichloride in 701 ml of THF are slowly added dropwise to the reaction solution. The reaction mixture is stirred at room temperature for 3.5 h. After reaction is complete, the solution is cooled to 0° C. and aqueous sodium hydroxide solution is slowly added. The aqueous phase is extracted three times with ethyl acetate, and the combined organic phases are dried over sodium sulfate, filtered and concentrated to dryness in vacuo. The crude product is purified by chromatography on 10 kg of silica gel (mobile phase: dichloromethane/methanol 6:4). 90.28 g (61% of theory) of the title compound are obtained.

$^1$H-NMR (300 MHz, CDCl$_3$, δ/ppm): 1.50 (2H, br. s), 3.00 (4H, m), 5.10 (2H, s), 6.90 (3H, m), 7.50 (2H, d), 7.60 (2H, d), 7.70 (4H, s).

Example 46A

Ethyl 5-{[2-(5-fluoro-2-{[4'-(trifluoromethyl)biphenyl-4-yl]methoxy}phenyl)ethyl]amino}-pentanoate

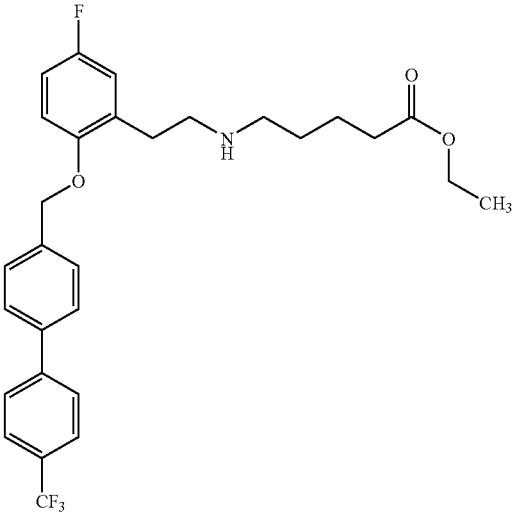

13.8 g (30 mmol) of 2-(5-fluoro-2-{[4'-(trifluoromethyl)biphenyl-4-yl]methoxy}phenyl)ethylamine hydrochloride [obtainable by taking up the compound of Example 45A in a 1 M solution of hydrogen chloride in dioxane, reconcentrating the solution and drying the resulting residue] are introduced into 200 ml of DMF, mixed with 32.4 ml (0.23 mol) of triethylamine and heated to 60-65° C. At this temperature, 9.48 g (0.05 mol) of ethyl 5-bromovalerate are added dropwise, and the mixture is stirred for 12 hours. After cooling, the mixture is added to water, adjusted to pH 5 with 1 M hydrochloric acid and extracted with ethyl acetate. The organic phase is dried over sodium sulfate and the solvent is removed in vacuo. The resulting residue is purified by chromatography on silica gel (mobile phase: dichloromethane/methanol 10:1). 4.5 g (8.9 mmol, 18% of theory) of the title compound are obtained.

LC-MS (method 5): $R_t$ 2.58 min; m/z 504 (M+H)$^+$.

Example 47A

5-{[2-(5-Fluoro-2-{[4'-(trifluoromethyl)biphenyl-4-yl]methoxy}phenyl)ethyl]amino}pentanoic acid

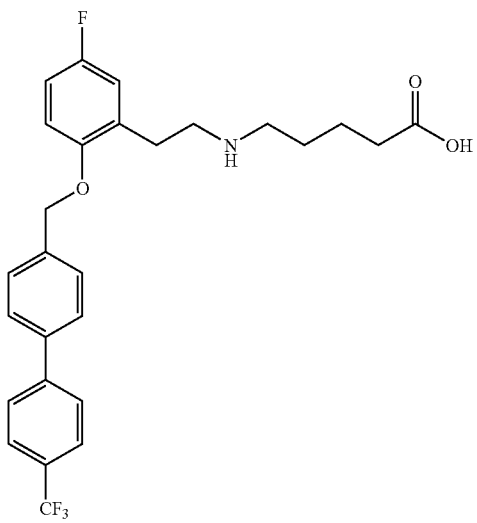

A solution of 4.5 g (6.93 mmol) of ethyl 5-{[2-(5-fluoro-2-{[4'-(trifluoromethyl)biphenyl-4-yl]-methoxy}phenyl)ethyl]amino}pentanoate in 90 ml of THF is mixed with 18 ml of half-concentrated hydrochloric acid and heated at 100° C. for 20 min. After cooling, the mixture is added to water and neutralized with saturated sodium bicarbonate solution. It is extracted with ethyl acetate, the organic phase is dried over sodium sulfate and the solvent is removed in vacuo. The residue is crystallized from ethyl acetate/diethyl ether (1:1). The resulting crystals are filtered off with suction and dried under high vacuum. 2.4 g (4.9 mmol, 71% of theory) of the title compound are obtained.

MS (ESIpos): m/z 490 (M+H)$^+$.

Example 48A

1-Allyl 7-ethyl 2-allyloxycarbonylheptanedioate

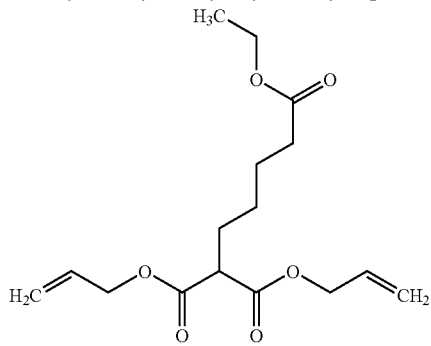

16.29 g (407.19 mmol) of sodium hydride are added in portions to a solution of 100 g (542.92 mmol) of diallyl malonate in 900 ml of dry dioxane at 5° C. After gas evolution ceases, the reaction mixture is warmed to 40° C. and stirred for 30 min. Then 56.76 g (271.46 mmol) of ethyl 5-bromovalerate in 100 ml of dry dioxane are added dropwise, and the mixture is stirred at 110° C. for 12 hours. After the reaction is complete, the mixture is cooled to room temperature and added to about 400 ml of ice-water. After neutralization of the reaction mixture with 1 N hydrochloric acid, the organic phase is separated off, and the aqueous phase is extracted three times with 250 ml of ethyl acetate each time. After the organic phases have been combined they are washed with saturated sodium chloride solution and dried over sodium sulfate. After filtration, the reaction solution is concentrated in vacuo. Subsequently excess diallyl malonate is removed by high vacuum distillation (boiling point: 57° C., 0.074 mbar). The distillation residue is purified by flash chromatography on silica gel (mobile phase: cyclohexane/ethyl acetate 2:1). 73.92 g (236.65 mmol, 44% of theory) of a colorless liquid are obtained.

$^1$H-NMR (400 MHz, DMSO-d$_6$, δ/ppm): 5.99-5.81 (2H, m), 5.38-5.16 (4H, m), 4.68-4.51 (4H, m), 4.04 (2H, q), 3.59 (1H, t), 2.28 (2H, t), 1.86-1.71 (2H, m), 1.61-1.45 (2H, m), 1.35-1.20 (2H, m), 1.17 (3H, t).

MS (DCI): m/z 330 (M+NH$_4^+$).

Exemplary Embodiments

Example 1

6-(3,5-Difluoro-4-hydroxybenzyl)-8-[5-fluoro-2-(4'-trifluoromethylbiphenyl-4-ylmethoxy)phenyl]oct-7-enoic acid

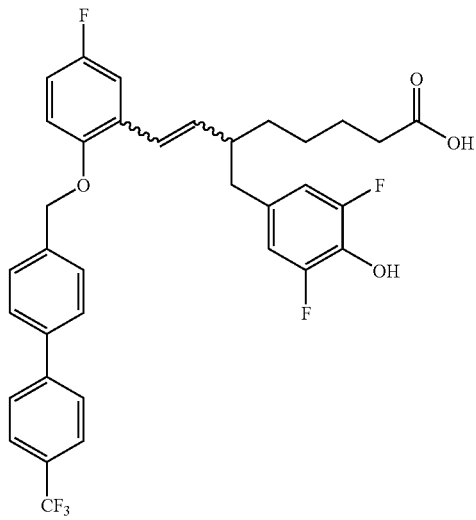

400 mg (0.61 mmol) of ethyl 6-(3,5-difluoro-4-hydroxybenzyl)-8-[5-fluoro-2-(4'-trifluoromethylbiphenyl-4-ylmethoxy)phenyl]oct-7-enoate are stirred overnight at 50° C. with 73 mg (1.83 mmol) of sodium hydroxide in a mixture of 20 ml of THF and 10 ml of water. The cooled mixture is acidified with dilute hydrochloric acid and extracted with ethyl acetate, and the combined organic phases are dried over sodium sulfate and concentrated. 333 mg (86% of theory) of the title compound are obtained as E/Z mixture (2:1).

$^1$H-NMR (400 MHz, CDCl$_3$, δ/ppm): 1.3-1.7 (m, 6H), 2.2-2.8 (m, 5H), 5.0 (s, 2H (Z)), 5.05 (s, 2H (E)), 5.45 (t, 1H (Z)), 5.95 (dd, 1H (E)), 6.55-6.9 (m, 5H), 7.1 (dd, 1H (E)), 7.45 (m, 2H), 7.65 (t, 2H), 7.7 (d, 4H).

LC-MS (method 3): R$_t$ 3.18 min; m/z 627 (M−H)$^−$.

The following compounds are obtained in an analogous manner:

Example 4

E-6-(3,5-Difluoro-4-hydroxybenzyl)-8-[5-fluoro-2-(4'-trifluoromethylbiphenyl-4-ylmethoxy)phenyl]oct-7-enoic acid (enantiomer 1)

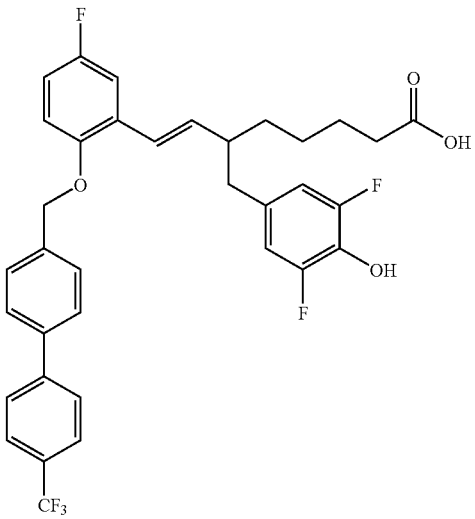

| Example No. | Structure | Analytical data |
|---|---|---|
| 2 | 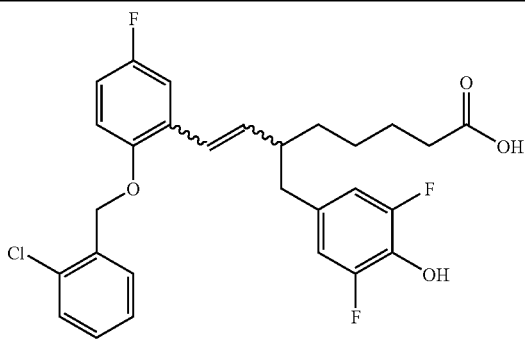 | $^1$H-NMR (300 MHz, CDCl$_3$, δ/ppm). 1.3-1.7 (m, 6H), 2.25 (m, 2H), 2.45 (m, 1H), 2.6 (m, 2H), 5.05 (s, 2H (Z)), 5.1 (s, 2H (E)), 5.45 (t, 1H (Z)), 5.95 (dd, 1H (E)), 6.55 (m, 2H), 6.7 (m, 2H), 6.85 (m, 2H), 7.1 (dd, 1H (E)), 7.3 (m, 2H), 7.4 (m, 2H). LC-MS (method 2): R$_t$ 2.70 min; m/z 536 (M + NH$_4$)$^+$. |
| 3 | 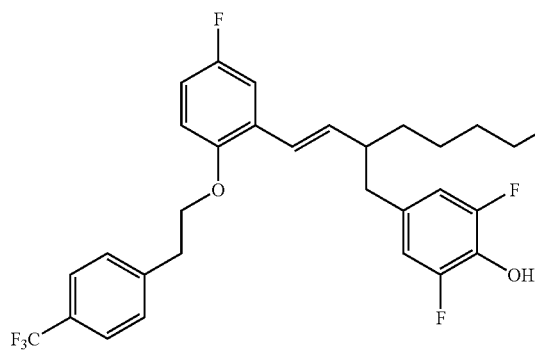 | $^1$H-NMR (400 MHz, CDCl$_3$, δ/ppm): 1.3-1.65 (m, 6H), 2.3 (m, 3H), 2.55 (m, 2H), 3.15 (m, 2H), 4.15 (t, 2H), 5.85 (dd, 1H), 6.35 (d, 1H), 6.7 (m, 2H), 6.75 (m, 1H), 6.85 (m, 1H), 7.05 (dd, 1H), 7.4 (m, 2H), 7.6 (m, 2H). LC-MS (method 1): R$_t$ 2.95 min; m/z 565 (M − H)$^−$. |

333 mg (0.53 mmol) of E/Z-6-(3,5-difluoro-4-hydroxybenzyl-8-[5-fluoro-2-(4'-trifluoromethylbiphenyl-4-ylmethoxy)phenyl]oct-7-enoic acid (Example 1) are fractionated further by preparative HPLC on a chiral phase. Respectively 60 mg and 46 mg of the two E isomers, each enantiopure, and respectively 42 mg and 38 mg of the two Z isomers are obtained as colorless solids (see Examples 4-7).

Enantiomer separation method:

Column: Daicel Chiralpak AD-H 250 mm×20 mm; eluent: isopropanol (with 1% water and 0.2% trifluoroacetic acid)/isohexane 30:70 (v/v); flow rate: 15 ml/min; UV detection: 220 nm; temperature: 24° C.

R$_t$ 8.79 min; purity 99%; >99% ee

Yield: 60 mg

¹H-NMR (400 MHz, CDCl₃, δ/ppm): 1.25-1.7 (m, 6H), 2.3 (t, 2H), 2.4 (m, 1H), 2.6 (ddd, 2H), 5.1 (s, 2H), 5.95 (dd, 1H), 6.6 (d, 1H), 6.7 (d, 2H), 6.85 (m, 2H), 7.1 (dd, 1H), 7.45 (d, 2H), 7.65 (d, 2H), 7.7 (s, 4H).

Example 5

E-6-(3,5-Difluoro-4-hydroxybenzyl)-8-[5-fluoro-2-(4'-trifluoromethylbiphenyl-4-ylmethoxy)phenyl]oct-7-enoic acid (enantiomer 2)

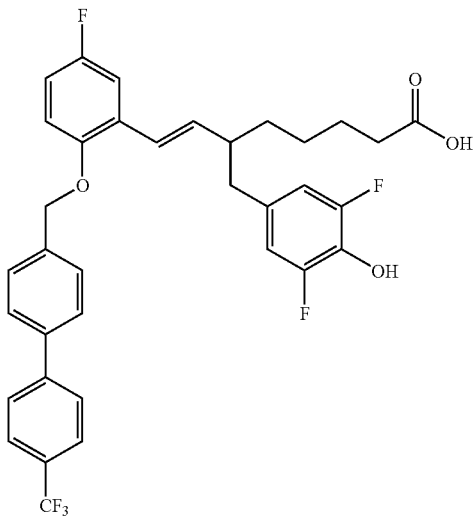

Enantiomer separation method: see Example 4.
R$_t$ 9.35 min; purity 99%; >98% ee
Yield: 46 mg
¹H-NMR (400 MHz, CDCl₃, δ/ppm): 1.25-1.7 (m, 6H), 2.3 (t, 2H), 2.4 (m, 1H), 2.6 (ddd, 2H), 5.1 (s, 2H), 5.95 (dd, 1H), 6.6 (d, 1H), 6.7 (d, 2H), 6.85 (m, 2H), 7.1 (dd, 1H), 7.45 (d, 2H), 7.65 (d, 2H), 7.7 (s, 4H).

Example 6

Z-6-(3,5-Difluoro-4-hydroxybenzyl)-8-[5-fluoro-2-(4'-trifluoromethylbiphenyl-4-ylmethoxy)phenyl]oct-7-enoic acid (enantiomer 1)

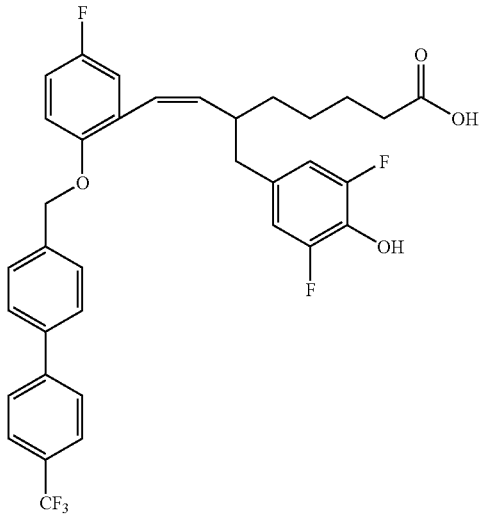

Enantiomer separation method: see Example 4.
R$_t$ 6.59 min; purity 100%; 100% ee
Yield: 42 mg
¹H-NMR (400 MHz, CDCl₃, δ/ppm): 1.3 (m, 2H), 1.45 (m, 2H), 1.55 (m, 2H), 2.25 (t, 2H), 2.45 (dd, 1H), 2.65 (dd, 1H), 2.75 (m, 1H), 5.0 (s, 2H), 5.45 (t, 1H), 6.55 (m, 2H), 6.6 (d, 2H), 6.8 (dd, 1H), 6.85 (ddd, 1H), 7.45 (d, 2H), 7.65 (d, 2H), 7.7 (s, 4H).

Example 7

Z-6-(3,5-Difluoro-4-hydroxybenzyl)-8-[5-fluoro-2-(4'-trifluoromethylbiphenyl-4-ylmethoxy)phenyl]oct-7-enoic acid (enantiomer 2)

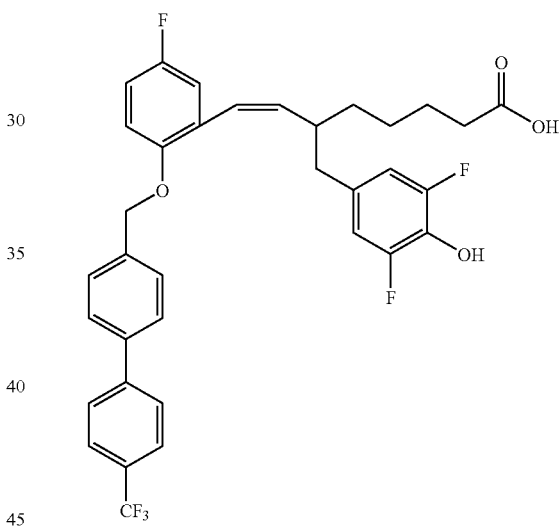

Enantiomer separation method: see Example 4.
R$_t$ 7.14 min; purity 99.6%; >99% ee
Yield: 38 mg
¹H-NMR (400 MHz, CDCl₃, δ/ppm): 1.3 (m, 2H), 1.45 (m, 2H), 1.55 (m, 2H), 2.25 (t, 2H), 2.45 (dd, 1H), 2.65 (dd, 1H), 2.75 (m, 1H), 5.0 (s, 2H), 5.45 (t, 1H), 6.55 (m, 2H), 6.6 (d, 2H), 6.8 (dd, 1H), 6.85 (ddd, 1H), 7.45 (d, 2H), 7.65 (d, 2H), 7.7 (s, 4H).

293 mg (0.56 mmol) of E/Z-8-[2-(2-chlorobenzyloxy)-5-fluorophenyl]-6-(3,5-difluoro-4-hydroxybenzyl)oct-7-enoic acid (Example 2) are further fractionated by preparative HPLC on a chiral phase. Respectively 50 mg and 34 mg of the two E isomers, each enantiopure, and respectively 56 mg and 26 mg of the two Z isomers are obtained as colorless solids (see Examples 8-11).

Example 8

E-8-[2-(2-Chlorobenzyloxy)-5-fluorophenyl]-6-(3,5-difluoro-4-hydroxybenzyl)oct-7-enoic acid (enantiomer 1)

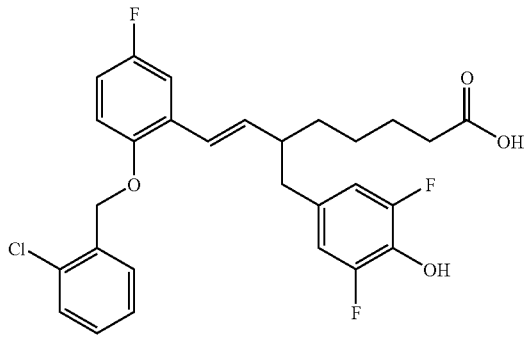

Enantiomer separation method:
Column: Daicel Chiralpak AD-H 250 mm×20 mm; eluent: isopropanol (with 1% water and 0.2% acetic acid)/isohexane 20:80 (v/v); flow rate: 15 ml/min; UV detection: 220 nm; temperature: 25° C.

$R_t$ 7.60 min; purity>99%; >99% ee

Yield: 50 mg $^1$H-NMR (400 MHz, CDCl$_3$, δ/ppm): 1.25-1.7 (m, 6H), 2.3 (t, 2H), 2.4 (m, 1H), 2.6 (m, 2H), 5.1 (s, 2H), 5.95 (dd, 1H), 6.6 (d, 1H), 6.7 (d, 2H), 6.85 (m, 2H), 7.1 (dd, 1H), 7.3 (m, 2H), 7.45 (m, 2H).

Example 9

E-8-[2-(2-Chlorobenzyloxy)-5-fluorophenyl]-6-(3,5-difluoro-4-hydroxybenzyl)oct-7-enoic acid (enantiomer 2)

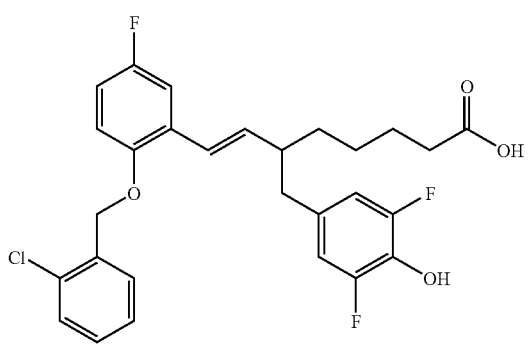

Enantiomer separation method: see Example 8.

$R_t$ 8.43 min; purity>99%; >98.5% ee

Yield: 34 mg $^1$H-NMR (400 MHz, CDCl$_3$, δ/ppm): 1.25-1.7 (m, 6H), 2.3 (t, 2H), 2.4 (m, 1H), 2.6 (m, 2H), 5.1 (s, 2H), 5.95 (dd, 1H), 6.6 (d, 1H), 6.7 (d, 2H), 6.85 (m, 2H), 7.1 (dd, 1H), 7.3 (m, 2H), 7.45 (m, 2H).

Example 10

Z-8-[2-(2-Chlorobenzyloxy)-5-fluorophenyl]-6-(3,5-difluoro-4-hydroxybenzyl)oct-7-enoic acid (enantiomer 1)

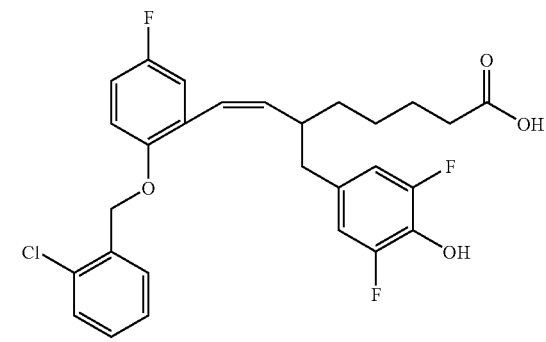

Enantiomer separation method: see Example 8.

$R_t$ 6.17 min; purity>99%; >99% ee

Yield: 56 mg $^1$H-NMR (400 MHz, CDCl$_3$, δ/ppm): 1.3 (m, 2H), 1.45 (m, 2H), 1.55 (m, 2H), 2.25 (t, 2H), 2.45 (dd, 1H), 2.65 (dd, 1H), 2.75 (m, 1H), 5.05 (s, 2H), 5.45 (t, 1H), 6.5 (m, 2H), 6.6 (d, 2H), 6.8 (m, 1H), 6.9 (m, 1H), 7.3 (m, 2H), 7.4 (dd, 1H), 7.5 (dd, 1H).

Example 11

Z-8-[2-(2-Chlorobenzyloxy)-5-fluorophenyl]-6-(3,5-difluoro-4-hydroxybenzyl)oct-7-enoic acid (enantiomer 2)

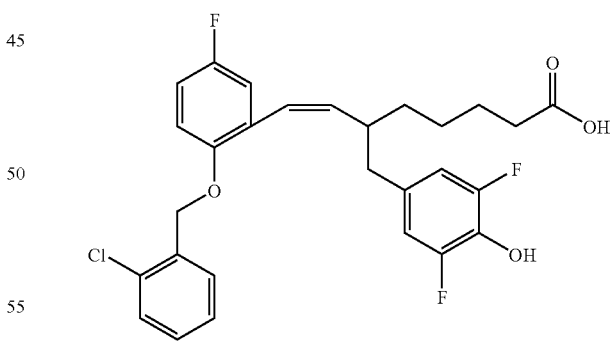

Enantiomer separation method: see Example 8.

$R_t$ 7.17 min; purity>99%; >99% ee

Yield: 26 mg $^1$H-NMR (400 MHz, CDCl$_3$, δ/ppm): 1.3 (m, 2H), 1.45 (m, 2H), 1.55 (m, 2H), 2.25 (t, 2H), 2.45 (dd, 1H), 2.65 (dd, 1H), 2.75 (m, 1H), 5.05 (s, 2H), 5.45 (t, 1H), 6.5 (m, 2H), 6.6 (d, 2H), 6.8 (m, 1H), 6.9 (m, 1H), 7.3 (m, 2H), 7.4 (dd, 1H), 7.5 (dd, 1H).

Example 12

E-4-[5-[2-(4-tert-Butylbenzyloxyphenyl]-3-(3,5-difluoro-4-hydroxybenzyl)pent-4-enyl]benzoic acid

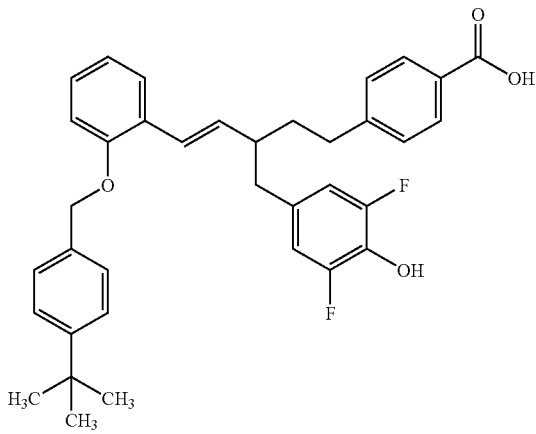

229 mg (0.39 mmol) of methyl E-4-[5-[2-(4-tert-butylbenzyloxy)phenyl]-3-(3,5-difluoro-4-hydroxybenzyl)pent-4-enyl]benzoate in 10 ml of methanol are stirred overnight at room temperature with 2 ml of 45% strength sodium hydroxide solution. After the reaction is complete, the mixture is acidified with dilute hydrochloric acid and extracted with ethyl acetate. The combined organic phases are dried over sodium sulfate and concentrated. The resulting crude product is purified by preparative HPLC. 154 mg (67% of theory) of the title compound are obtained.

LC-MS (method 2): $R_t$ 3.08 min; m/z 569 (M–H)⁻.

154 mg (0.27 mmol) of E-4-[5-[2-(4-tert-butylbenzyloxy)phenyl]-3-(3,5-difluoro-4-hydroxybenzyl)pent-4-enyl]benzoic acid are fractionated further by preparative HPLC on a chiral phase. Respectively 55 mg and 51 mg of the two E isomers, each enantiopure, are obtained as colorless solids (see Examples 13 and 14).

Example 13

E4-[5-[2-(4-tert-Butylbenzyloxy)phenyl]-3-(3,5-difluoro-4-hydroxybenzyl)pent-4-enyl]benzoic acid (enantiomer 1)

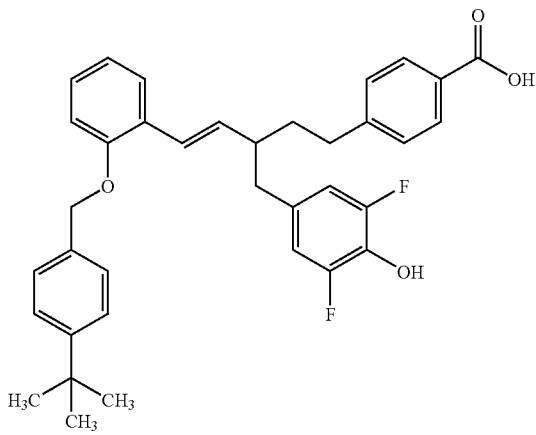

Enantiomer separation method:
Column: Daicel Chiralpak AD-H 250 mm×20 mm; eluent: isopropanol (with 1% water and 0.2% trifluoroacetic acid)/isohexane 30:70 (v/v); flow rate: 15 ml/min; UV detection: 220 nm; temperature: 24° C.

$R_t$ 5.79 min; purity 99.5%; >99% ee
Yield: 55 mg

¹H-NMR (400 MHz, DMSO-d₆, δ/ppm): 12.82-12.71 (1H, broad), 9.81 (1H, s), 7.82 (2H, d), 7.42 (1H, d), 7.39-7.29 (4H, m), 7.25 (2H, d), 7.19 (1H, t), 7.06 (1H, d), 6.90 (1H, t), 6.82 (2H, d), 6.53 (1H, d), 6.13-6.03 (1H, m), 5.07 (2H, s), 2.77-2.63 (3H, m), 2.62-2.35 (2H, m), 1.80-1.68 (1H, m), 1.67-1.52 (1H, m), 1.24 (9H, s).

MS (EI): 569 (M–H)⁻.

Example 14

E-4-[5-[2-(4-tert-Butylbenzyloxy)phenyl]-3-(3,5-difluoro-4-hydroxybenzyl)pent-4-enyl]benzoic acid (enantiomer 2)

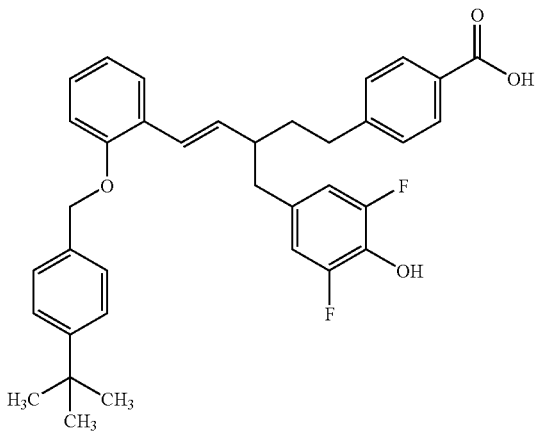

Enantiomer separation method: see Example 13.
$R_t$ 6.33 min; purity 99%; >99% ee
Yield: 51 mg
MS (EI): 569 (M–H)⁻.

Example 15

E-4-(4-[2-(4-tert-Butylbenzyloxy)phenyl]-2-{2-[4-(1H-tetrazol-5-yl)phenyl]ethyl}but-3-enyl)-2,6-difluorophenol

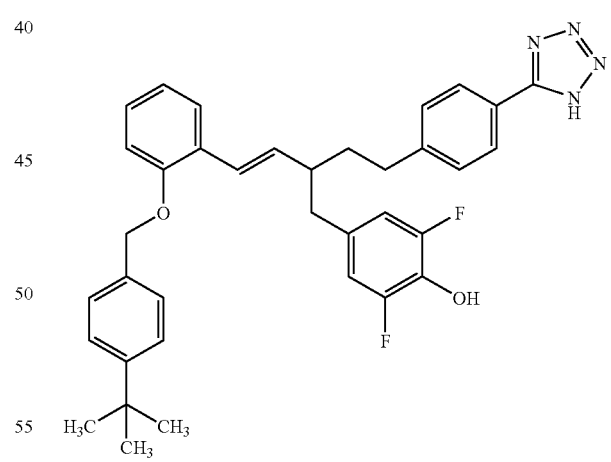

442 mg (0.51 mmol, 86%-pure) of E-5-{4-[5-[2-(4-tert-butylbenzyloxy)phenyl]-3-(3,5-difluoro-4-triisopropylsilanyloxybenzyl)pent-4-enyl]phenyl}-1H-tetrazole are charged in 12 mol of THF, cooled to 0° C., mixed with 1.18 ml (1.18 mmol) of a 1 M solution of tetra-n-butylammonium fluoride in THF with exclusion of oxygen and stirred at room temperature for 2 hours. The mixture is then added to ammonium chloride solution and extracted with ethyl acetate. The organic phase is dried over sodium sulfate and concentrated. 297 mg (0.5 mmol, 98% of theory) of the title compound are obtained.

LC-MS (method 1): $R_t$=3.3 min
MS (ESIpos): m/z=595 (M+H)$^+$.

297 mg (0.5 mmol) of 4-((3E) {2-[(4-tert-butylbenzyl)oxy]phenyl}-2-{2-[4-(1H-tetrazol-5-yl)phenyl]ethyl}but-3-en-1-yl)-2,6-difluorophenol are further fractionated by preparative HPLC on a chiral phase. Respectively 140 mg and 52 mg of the two E isomers, each enantiopure, are obtained (see Examples 16 and 17).

Example 16

E-4-(4-[2-(4-tert-Butylbenzyloxy)phenyl]-2-{2-[4-(1H-tetrazol-5-yl)phenyl]ethyl}but-3-enyl)-2,6-difluorophenol (enantiomer 1)

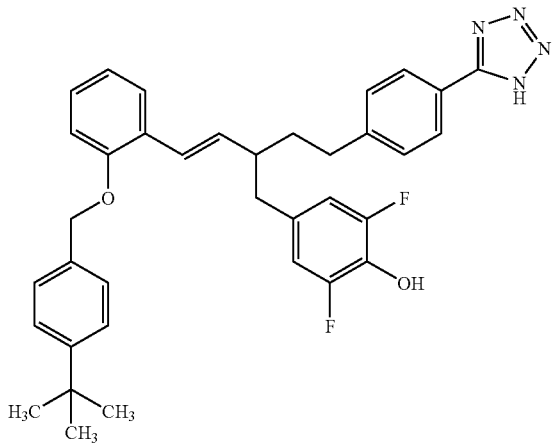

Enantiomer separation method:
Column: Daicel Chiralpak OD-H 250 mm×20 mm; eluent: isopropanol (with 1% water and 0.2% trifluoroacetic acid)/isohexane 30:70 (v/v); flow rate: 15 ml/min; UV detection: 220 nm; temperature: 30° C.
$R_t$ 5.16 min; purity>80%; >95% ee
Yield: 140 mg
LC-MS (method 3): $R_t$=3.19 min
MS (ESIpos): m/z=595 (M+H)$^+$.

Example 17

E-4-(4-[2-(4-tert-Butylbenzyloxy)phenyl]-2-{2-[4-(1H-tetrazol-5-yl)phenyl]ethyl}but-3-enyl)-2,6-difluorophenol (enantiomer 2)

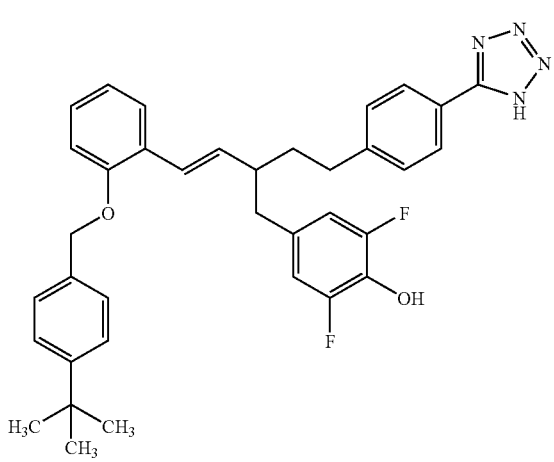

Enantiomer separation method: see Example 16.
$R_t$ 5.81 min; purity>80%; >60% ee
Yield: 52 mg

Example 18

5-{(3,5-Difluoro-4-hydroxybenzyl)-[2-(5-fluoro-2-{[4'-(trifluoromethyl)biphenyl-4-yl]methoxy}phenyl)ethyl]amino}pentanoic acid

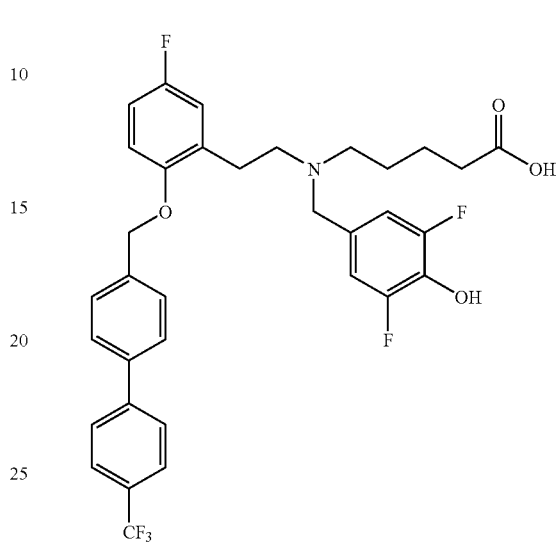

A solution of 40 mg (0.08 mmol) of 5-{[2-(5-fluoro-2-{[4'-(trifluoromethyl)biphenyl-4-yl]methoxy}phenyl)ethyl]amino}pentanoic acid in 5 ml of acetone is mixed with 54.5 mg (0.09 mmol) of [4-(bromomethyl)-2,6-difluorophenoxy]triisopropyl)silane (Example 16A), 22.6 mg (0.16 mmol) of potassium carbonate and 20.3 mg (0.12 mmol) of potassium iodide and heated under reflux for 12 h. Cooling is followed by addition of water to the mixture and extraction with ethyl acetate. The organic phase is washed with saturated sodium chloride solution, dried over magnesium sulfate and the solvent is distilled off in vacuo. The resulting residue is purified by preparative HPLC. 15.3 mg (0.024 mmol, 30% of theory) of the title compound are obtained.
$^1$H-NMR (300 MHz, DMSO-d$_6$): δ=7.89 (2H, d), 7.80 (2H, d), 7.73 (2H, d), 7.5 (2H, d), 7.05 (3H, m), 6.82 (2H, d), 5.09 (2H, s), 3.44 (2H, s), 2.77-2.70 (4H, m), 2.65-2.58 (1H, m), 2.43-2.36 (2H, m), 2.29-2.25 (1H, m), 2.12-2.05 (2H, m), 1.45-1.34 (2H, m).
MS (ESIpos): m/z=632 (M+H)$^+$.

B. ASSESSMENT OF THE PHARMACOLOGICAL ACTIVITY

The pharmacological effect of the compounds according to the invention can be shown in the following assays:
B-1. Vasorelaxant Effect In Vitro:

Rabbits are anesthetized and sacrificed by intravenous injection of thiopental sodium (about 50 mg/kg) and exsanguinated. The saphenous artery is removed and divided into rings 3 mm wide. The rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with 95% O$_2$/5% CO$_2$ and has the following composition: NaCl 119 mM; KCl 4.8 mM; CaCl$_2$×2H$_2$O 1 mM; MgSO$_4$×7 H$_2$O 1.4 mM; KH$_2$PO$_4$ 1.2 mM; NaHCO$_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the height of the contraction achieved under the influence of the test substance is compared with the height of the contraction reached in the last preceding run. The concentration necessary to reduce the contraction reached in the preceding control by 50% is calculated from this ($IC_{50}$). The standard application volume is 5 µl. The proportion of DMSO in the bath solution corresponds to 0.1%.

Representative results on the compounds according to the invention are listed in Table 1:

TABLE 1

Vasorelaxant effect in vitro

| Example No. | $IC_{50}$ [nM] |
|---|---|
| 4 | 960 |
| 5 | 300 |
| 6 | 2700 |
| 7 | 2600 |
| 8 | 647 |
| 13 | 24.5 |
| 14 | 1218 |
| 18 | 43 |

B-2. Stimulation of Recombinant Soluble Guanylate Cyclase (sGC) In Vitro:

Investigations on the stimulation of recombinant soluble guanylate cyclase (sGC) by the compounds according to the invention with and without sodium nitroprusside, and with and without the heme-dependent sGC inhibitor 1H-1,2,4-oxadiazole-(4,3a)-quinoxalin-1-one (ODQ) are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The heme-free guanylate cyclase is obtained by adding Tween 20 to the sample buffer (0.5% in the final concentration).

The activation of sGC by a test substance is reported as n-fold stimulation of the basal activity. The result for Example 13 is shown in Table 2:

TABLE 2

Stimulation (n-fold) of recombinant soluble guanylate cyclase (sGC) in vitro by Example 13

| Concentration of Example 13 [µM] | Heme-containing sGC | | | Heme-free sGC | |
|---|---|---|---|---|---|
| | Basal | +0.1 µM DEA/NO | +10 µM ODQ | Basal | +10 µM ODQ |
| 0.0 | 1.0 | 26.5 | 35.6 | 1.0 | 0.8 |
| 0.001 | 1.7 | 26.3 | 37.5 | 4.1 | 4.0 |
| 0.01 | 6.7 | 31.2 | 38.8 | 30.6 | 27.1 |
| 0.1 | 19.2 | 40.2 | 43.8 | 94.4 | 88.6 |
| 1 | 24.2 | 43.2 | 52.2 | 122.8 | 118.5 |
| 10 | 36.2 | 62.0 | 63.7 | 126.3 | 118.4 |

[DEA/NO = 2-(N,N-diethylamino)diazenolate 2-oxide; ODQ = 1H-1,2,4-oxadiazole-(4,3a)-quinoxalin-1-one].

It is evident from Table 2 that stimulation both of the heme-containing and of the heme-free enzyme is achieved. Furthermore, combination of Example 13 and 2-(N,N-diethylamino)-diazenolate 2-oxide (DEA/NO), an NO donor, shows no synergistic effect, i.e. the effect of DEA/NO is not potentiated as would be expected with an sGC activator acting via a heme-dependent mechanism. In addition, the effect of the sGC activator according to the invention is not blocked by the heme-dependent inhibitor of soluble guanylate cyclase ODQ, but is in fact increased. The results in Table 2 thus confirm the mechanism of action of the compounds according to the invention as activators of soluble guanylate cyclase.

B-3. Radiotelemetric Measurement of Blood Pressure and Heart Rate on Conscious Sh Rats A commercially available telemetry system from Data Sciences International DSI, USA, is employed for the measurements on conscious SH rats described below.

The system consists of 3 main components: (1) implantable transmitter, (2) receiver which is linked via a multiplexer to a (3) data acquisition computer. The telemetry system makes it possible to record continuously the blood pressure and heart rate on conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 in the morning and at 19.00 in the evening.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anesthetized with pentobarbital (Nembutal, Sanofi, 50 mg/kg i.p.) and shaved and disinfected over a large area on the side of the abdomen. After the abdominal cavity has been opened along the linea alba, the liquid-filled measuring catheter of the system is inserted into the descending aorta in the cranial direction above the bifurcation and fastened with tissue glue (VetBonD™, 3M). The transmitter housing is fixed intraperitoneally to the abdominal wall muscle, and layered closure of the wound is performed. An antibiotic (Tardomyocel COMP, Bayer, 1 ml/kg s.c.) is administered postoperatively for prophylaxis of the infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated from outside by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file bearing the experiment number which is open for this purpose.

In the standard procedure, the following are measured for 10-second periods in each case: (1) systolic blood pressure (SBP), (2) diastolic blood pressure (DBP), (3) mean arterial pressure (MAP) and (4) heart rate (HR).

Measurement acquisition is repeated under computer control at 5-minute intervals. The source data obtained as absolute value are corrected in the diagram with the currently measured barometric pressure and stored in individual data. Further technical details are given in the documentation of the manufacturing company (DSI).

The test substances are administered at 9.00 h on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 h on the day of the experiment to 9.00 h on the following day.

The data are smoothed over a presettable time by determination of the average (15-minute average, 30-minute average) and transferred as text file to a storage medium. The measurements presorted and compressed in this way are transferred into Excel templates and tabulated.

C. EXEMPLARY EMBODIMENTS OF PHARMACEUTICAL COMPOSITIONS

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400.20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

I.V.-Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

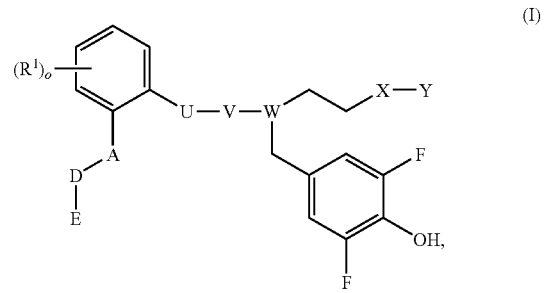

in which
U, V and W together form a group of the formula *—CH=CH—CH<, *—CH$_2$—CH$_2$—CH< or *—CH$_2$—CH$_2$—N<, in which * means the point of linkage to the phenyl ring,
A is O or CH$_2$,
D is a bond or is $(C_1-C_7)$-alkanediyl, $(C_2-C_7)$-alkenediyl or $(C_2-C_7)$-alkynediyl, each of which may be substituted one or more times by fluorine,
E is hydrogen, trifluoromethyl or a group of the formula

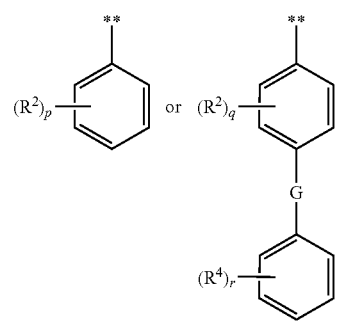

in which ** means the point of linkage to the group D and
G is a bond, CH$_2$, —CH$_2$—CH$_2$— or —CH=CH—,
X is —CH$_2$—CH$_2$— or a group of the formula

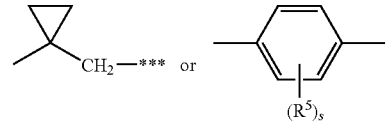

in which *** means the point of linkage to the group Y,
Y is carboxyl or a group of the formula

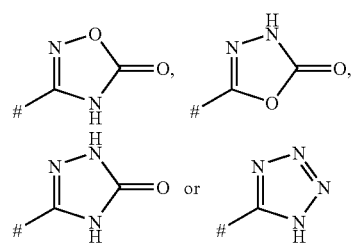

in which # means the respective point of linkage,
$R^1$, $R^2$, $R^3$, $R^4$ and $R^5$ are independently of one another substituents selected from the series halogen, $(C_1-C_6)$- alkyl, trifluoromethyl, $(C_1-C_6)$-alkoxy, trifluoromethoxy, cyano and nitro, and o, p, q, r and s are independently of one another each the number 0, 1, 2, 3 or 4, where in the case where $R^1$, $R^2$, $R^3$, $R^4$ or $R^5$ occur more than once, their meanings may in each case be identical or different, and salts thereof.

2. The compound of the formula (I) as claimed in claim 1, in which

U, V and W together form a group of the fomula *—CH=CH—CH< or *—CH$_2$—CH$_2$—N< in which * means the point of linkage to the phenyl ring, A is O, D is $(C_1-C_7)$-alkanediyl which may be substituted one or more times by fluorine, E is hydrogen, trifluoromethyl or is a group of the formula in which  means the point of linkage to the group D, X is —CH$_2$—CH$_2$— or a group of the formula in which * means the point of linkage to the group Y, Y is carboxyl or a group of the formula in which # means the respective point of linkage, and $R^1$, $R^2$, $R^3$ and $R^4$ are independently of one another a substituent selected from the series fluorine, chlorine, bromine, $(C_1-C_4)$-alkyl, trifluoromethyl, $(C_1-C_4)$-alkoxy and trifluoromethoxy, o, p, q and r are independently of one another each the number 0, 1 or 2, where in the case where $R^1$, $R^2$, $R^3$ or $R^4$ occur more than once, their meanings may in each case be identical or different, $R^5$ is fluorine, and s is the number 0 or 1, and salts thereof.

3. A compound of the formula (I-A)

(I-A)

in which

D is $(C_1-C_7)$-alkanediyl which may be substituted one or more times by fluorine, E is hydrogen, trifluoromethyl or is a group of the formula in which ** means the point of linkage to the group D, Y is carboxyl or a group of the formula in which # means the point of linkage, $R^1$, $R^2$, $R^3$ and $R^4$ are independently of one another a substituent selected from the series fluorine, chlorine, bromine, methyl, tent-butyl, trifluoromethyl and methoxy, and o, p, q and r are independently of one another each the number 0, 1 or 2, where in the case that $R^1$, $R^2$, $R^3$ or $R^4$ occur more than once, their meanings may in each case be identical or different, and salts thereof.

4. A compound of the formula (I-B)

(I-B)

in which

D is $(C_1-C_7)$-alkanediyl which may be substituted one or more times by fluorine, E is hydrogen, trifluoromethyl or is a group of the formula

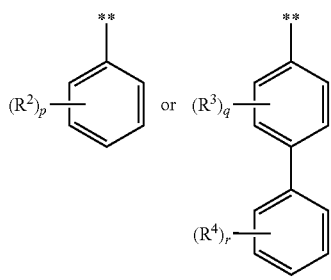

in which ** means the point of linkage to the group D, $R^1$, $R^2$, $R^3$ and $R^4$ are independently of one another a substituent selected from the series fluorine, chlorine, bromine, methyl, tert-butyl, trifluoromethyl and methoxy, and o, p, q and r are independently of one another each the number 0, 1 or 2, where in the case that $R^1$, $R^2$, $R^3$ or $R^4$ occur more than once, their meanings may in each case be identical or different, and salts thereof.

5. A pharmaceutical composition comprising a compound as defined in claim 1 in combination with an inert, non-toxic, pharmaceutically suitable excipient.

6. The pharmaceutical composition of claim 5 further comprising an active ingredient selected from the group consisting of organic nitrates, NO donors, cGMP-PDE inhibitors, stimulators of guanylate cyclase, agents having antithrombotic activity, active ingredients which lower blood pressure, and active ingredients which modify lipid metabolism.

* * * * *